United States Patent
Cho et al.

(10) Patent No.: US 10,143,749 B2
(45) Date of Patent: *Dec. 4, 2018

(54) BISPECIFIC ANTI-CMET/ANTI-HER2 ANTIBODIES

(71) Applicant: Samsung Electronics Co., Ltd., Suwon-si, Gyeonggi-do (KR)

(72) Inventors: Mi Young Cho, Seoul (KR); Powei Lin, Hwaseong-si (KR); Seung Hyun Lee, Suwon-si (KR); Kwang Ho Cheong, Seoul (KR); Young Jun Koh, Yongin-si (KR); Christina Yi, Seongnam-si (KR); Jae Woong Hwang, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 70 days.

This patent is subject to a terminal disclaimer.

(21) Appl. No.: 14/229,308

(22) Filed: Mar. 28, 2014

(65) Prior Publication Data

US 2014/0294838 A1  Oct. 2, 2014

(30) Foreign Application Priority Data

Mar. 28, 2013  (KR) ................. 10-2013-0033876

(51) Int. Cl.
| | |
|---|---|
| *C07K 16/30* | (2006.01) |
| *C07K 16/46* | (2006.01) |
| *A61K 39/395* | (2006.01) |
| *C07K 16/28* | (2006.01) |
| *C07K 16/32* | (2006.01) |

(52) U.S. Cl.
CPC .... *A61K 39/39558* (2013.01); *C07K 16/2863* (2013.01); *C07K 16/32* (2013.01); *C07K 2317/24* (2013.01); *C07K 2317/31* (2013.01); *C07K 2317/34* (2013.01); *C07K 2317/565* (2013.01); *C07K 2317/622* (2013.01); *C07K 2317/64* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,052,872 B1 | 5/2006 | Hansen et al. | |
| 7,125,541 B2 | 10/2006 | Thorpe et al. | |
| 7,691,380 B2 | 4/2010 | Thorpe et al. | |
| 7,951,918 B2 | 5/2011 | Glaser et al. | |
| 8,563,696 B2 | 10/2013 | Cheong et al. | |
| 2005/0079184 A1 | 4/2005 | Hsing-Chang et al. | |
| 2009/0226443 A1 | 9/2009 | Filvaroff et al. | |
| 2009/0226455 A1 | 9/2009 | Filvaroff | |
| 2010/0166746 A1 | 7/2010 | Chowdhury et al. | |
| 2010/0254988 A1 | 10/2010 | Bossenmaier et al. | |
| 2010/0254989 A1 | 10/2010 | Bossenmaier et al. | |
| 2010/0260668 A1 | 10/2010 | Ghayur et al. | |
| 2011/0104176 A1* | 5/2011 | Cheong ............. | C07K 16/2863 424/152.1 |
| 2012/0065380 A1 | 3/2012 | Yoo et al. | |
| 2013/0089542 A1* | 4/2013 | Lee et al. ................. | 424/133.1 |

FOREIGN PATENT DOCUMENTS

| | | |
|---|---|---|
| EP | 2 727 941 A1 | 5/2014 |
| KR | 10-20100125033 A | 11/2010 |
| KR | 10-20110047698 A | 5/2011 |
| WO | WO 96/01653 A1 | 1/1996 |
| WO | WO 2010-115553 A1 | 10/2014 |

OTHER PUBLICATIONS

Paul, Fundamental Immunology, 3rd Edition, 1993, pp. 292-295.*
Bendig M. M. (Methods: A Companion to Methods in Enzymology, 1995; 8:83-93).*
Rudikoff et al. (Proceedings of the National Academy of Sciences USA, vol. 79, p. 1979, 1982).*
Johnson and Wu (Methods in Molecular Biology, Antibody Engineering: Methods and Protocols, vol. 248, p. 11-25, 2004).*
Bonsignori (Cell, vol. 165, p. 449-463, 2016).*
Panka (Proceedings of the National Academy of Sciences, USA, vol. 85, p. 3080-3084, 1988).*
Kearns (Molecular Cancer Therapeutics, vol. 14, No. 7, p. 1625-1636, published Apr. 24, 2015) (Year: 2015).*
Extended European Search Report for 14161871.0 dated Aug. 6, 2014.
Oh et al., "A new anti-c-Met Antibody Selected by a Mechanism-Based Dual-Screening Method: Therapeutic Potential in Cancer," *Molecules and Cells*, 34: 523-529 (2012).
Bostrom et al., "Variants of the Antibody Herceptin That Interact with HER2 and VEGF at the Antigen Binding Site," *Science*, 323: 1610-1614 (2009).
Schaefer et al., "A Two-in-One Antibody against HER3 and EGFR Has Superior Inhibitory Activity Compared with Monospecific Antibodies," *Cancer Cell*, 20: 472-486 (2011).

\* cited by examiner

*Primary Examiner* — Michael Allen
(74) *Attorney, Agent, or Firm* — Leydig, Voit & Mayer, Ltd.

(57) ABSTRACT

There are provided an anti-c-Met/anti-Her2 bispecific antibody, and a method for preventing and/or treating cancer using the same.

10 Claims, 7 Drawing Sheets
(4 of 7 Drawing Sheet(s) Filed in Color)
Specification includes a Sequence Listing.

MKN45

BISPECIFIC ANTI-CMET/ANTI-HER2 ANTIBODIES

CROSS-REFERENCE TO RELATED APPLICATIONS

This application claims the benefit of Korean Patent Application No. 10-2013-0033876 filed on Mar. 28, 2013, in the Korean Intellectual Property Office, the entire disclosure of which is herein incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 142,361 Byte ASCII (Text) file named 715709_ST25-Revised3 created on Jun. 12, 2017.

BACKGROUND OF THE INVENTION

1. Field

Provided are an anti-c-Met/anti-Her2 bispecific antibody, and a method for preventing and/or treating cancer using the same.

2. Description of the Related Art c-Met and Her2 (or HER family) proteins interact with each other and are involved in various mechanisms related to tumors. These proteins are typical receptor tyrosine kinases (RTKs) present at the surface of cells, and thus, they induce the proliferation of cancer cells, the penetration of the cancer cells, angiogenesis, etc. Also, these proteins participate in each other's signal transduction system by interacting with each other, thereby inducing resistance against each other's therapeutic agents.

Meanwhile, multispecific antibodies targeting two or more antigens have been developed in various kinds and forms and are expected as a new drug antibody having excellent therapeutic effects compared to a monoclonal antibody. Most multispecific antibodies have been developed so that their therapeutic effects on cancers can be increased by recognizing an antigen of cytotoxic cells (killer cells) and another antigen of cancer cells at the same time, thereby allowing the cancer cells to be killed by the cytotoxic cells. Research results reveal that cancer cells themselves can be mutated to proliferate and penetrate by intracellular ligands or various antigens of the same cancer cells other than the targeted antigen. Therefore, there is a desire to develop a multispecific antibody capable of recognizing another antigen of the cancer cells, as well as an antigen of the killer cells, for treating cancers.

BRIEF SUMMARY OF THE INVENTION

One embodiment provides an anti-c-Met/anti-Her2 bispecific antibody including (a) an anti-c-Met antibody or an antigen-binding fragment thereof and (b) an anti-Her2 antibody or an antigen-binding fragment thereof, wherein the anti-c-Met antibody is an antibody specifically binding to an epitope consisting of consecutive 5 or more amino acids within a SEMA domain (SEQ ID NO: 79) of c-Met protein, wherein the epitope comprises at least the amino acid sequence of SEQ ID NO: 73.

Another embodiment provides a pharmaceutical composition for preventing and/or treating cancer including the anti-c-Met/anti-Her2 bispecific antibody as an active ingredient.

Another embodiment provides a method for preventing and/or treating cancer, including administering a pharmaceutically effective amount of the anti-c-Met/anti-Her2 bispecific antibody to a patient in need of the prevention and treatment of cancer.

Still another embodiment provides a use of the anti-c-Met/anti-Her2 bispecific antibody for the prevention and/or treatment of cancer.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
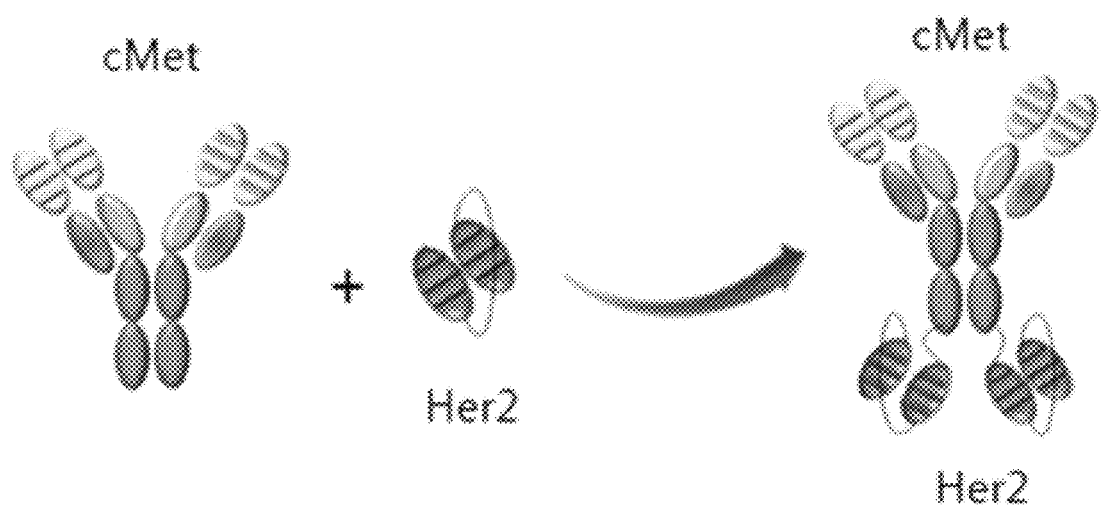
FIG. 1 is a schematic diagram showing the structure of an anti-c-Met/anti-Her2 bispecific antibody according to one example.

One embodiment of the present invention provides an anti-c-Met/anti-Her2 bispecific antibody comprising, consisting essentially of, or consisting of (a) an anti-c-Met antibody or an antigen-binding fragment thereof, and (b) an anti-Her2 antibody or an antigen-binding fragment thereof.

The antigen-binding fragment may be selected from the group consisting of scFv, (scFv)2, Fab, Fab', and F(ab')2.

The "c-Met protein" refers to a receptor tyrosine kinase binding to hepatocyte growth factor. The c-Met proteins may be derived from any species, for example, those derived from primates such as human c-Met (e.g., NP_000236) and monkey c-Met (e.g., *Macaca mulatta*, NP_001162100), or those derived from rodents such as mouse c-Met (e.g., NP_032617.2) and rat c-Met (e.g., NP_113705.1). The proteins include, for example, a polypeptide encoded by the nucleotide sequence deposited under GenBank Accession Number NM_000245, or a protein encoded by the polypeptide sequence deposited under GenBank Accession Number NM_000236, or extracellular domains thereof. The receptor tyrosine kinase c-Met is involved in several mechanisms including cancer incidence, cancer metastasis, cancer cell migration, cancer cell penetration, angiogenesis, etc.

The "Her2 (human epidermal growth factor receptor 2)" is encoded by ERBB2 gene, and is a member of the epidermal growth factor receptor (EGFR/ErbB). Her2 has been known to play an essential role in regulating cell proliferation and differentiation. Particularly, when bound to extracellular growth factors, it has a strong tendency of being assembled into homo- and/or heterodimers along with other HER receptors, which results in the activation of several forms of signal transduction pathway and induces apoptosis, survival, or cell proliferation.

For instance, the Her2 proteins may be polypeptides encoded by the nucleotide sequences (mRNA) deposited under GenBank Accession Number NM_004448.2, NM NM_001005862.1, etc.

In one embodiment, the anti-Her2 antibody may be selected from the group consisting of Trastuzumab, Pertuzumab, and Trastuzumab emtansine (T-DM1).

The antigen binding site of the anti-Her2 antibody recognizing Her2 as an antigen may be an antigen binding site, for example, scFv, (scFv)$_2$, Fab, Fab' or F(ab')2 of an anti-Her2 antibody selected from the group consisting of Trastuzumab, Pertuzumab, and Trastuzumab emtansine (T-DM1). For instance, the antigen binding site of the anti-Her2 antibody may be a scFv fragment derived from the anti-Her2 antibody and particularly it may be a form in which a heavy chain variable region comprising the amino acid sequence of SEQ ID NO: 109 and a light chain variable region comprising the amino acid sequence of SEQ ID NO: 111 are linked through a peptide linker or without it.

In one embodiment, the anti-c-Met/anti-Her2 bispecific antibody may be those including (a) an anti-c-Met antibody or an antigen-binding fragment thereof, and (b) an anti-Her2 antibody or an antigen-binding fragment thereof, which is linked to the C terminus or N terminus, for example, C terminus, of the anti-c-Met antibody or the antigen-binding fragment thereof.

In the anti-c-Met/anti-Her2 bispecific antibody, in order to fully perform the anti-c-Met antibody's activity to mediate intracellular migration and degradation of c-Met proteins, it may be advantageous that the anti-c-Met antibody has its own intact antibody structure. In addition, in case of the anti-Her2 antibody, its specific recognition and binding to Her2 is important, and, thus, just an antigen-binding fragment recognizing Her2 can be included in the bispecific antibody. Therefore, the anti-c-Met/anti-Her2 bispecific antibody may be those including a complete anti-c-Met antibody and an antigen-binding fragment of the anti-Her2 antibody linked to the C terminus of the anti-c-Met antibody.

In the anti-c-Met/anti-Her2 bispecific antibody, the anti-c-Met antibody or the antigen-binding fragment thereof, and the anti-Her2 antibody or the antigen-binding fragment thereof may be linked via a peptide linker or without it. Furthermore, a heavy chain portion and a light chain portion within the antigen-binding fragment, for example, a heavy chain variable region and a light chain variable region within the scFv fragment may be linked via a peptide linker or without it.

The peptide linker which links the anti-c-Met antibody or the antigen-binding fragment thereof, and the anti-Her2 antibody or the antigen-binding fragment thereof, and the peptide linker which links the heavy chain portion and the light chain portion within the antigen-binding fragment may be identical or different. The peptide linker may be those including any amino acids of 2 to 50, particularly 10 to 25 (e.g., 11, 12, 13, 14, 15, 16, 17, 18, 19, 20, 21, 22, 23, or 24) amino acids, and any kinds of amino acids may be included without any restrictions. In particular, the peptide linker may include one or more residues selected from the group consisting of Gly, Asn and Ser, and also include neutral amino acids such as Thr and/or Ala. Amino acid sequences suitable for the peptide linker may be those known in the pertinent art. Meanwhile, a length of the peptide linker may be variously determined within such a limit that the functions of the fusion protein will not be affected. For instance, the peptide linker may be represented as $(G_4S)_n$ (SEQ ID NO: 115) (n is a repeat number of $G_4S$ (SEQ ID NO: 117), which is an integer of 1 to 10, particularly an integer of 2 to 5 (e.g., 3 or 4).

The "antigen-binding fragment" refers to fragments of a full immunoglobulin structure including a portion capable of binding to an antigen. For example, the antigen-binding fragment may be scFv, (scFv)$_2$, Fab, Fab' or F(ab')2, but is not limited thereto.

Of the antigen-binding fragments, Fab is a structure having variable regions of a light chain and a heavy chain, a constant region of the light chain, and the first constant region ($C_{H1}$) of the heavy chain, and it includes one antigen binding site.

Fab' is different from Fab in that it includes a hinge region including one or more cysteine residues at the C-terminal of heavy chain $C_{H1}$ domain. An F(ab')$_2$ antibody is formed through disulfide bond of the cysteine residues at the hinge region of Fab'.

Fv is a minimal antibody piece including only a heavy chain variable region and light chain variable region, and a recombinant technique for producing the Fv fragment is well known in the pertinent art. Two-chain Fv may have a structure in which the heavy chain variable region is linked to the light chain variable region by a non-covalent bond, and single-chain Fv (scFv) may generally have a dimer structure as in the two-chain Fv in which the variable region of a heavy chain and the variable region of a light chain are covalently linked via a peptide linker or they are directly linked to each other at the C-terminal thereof. The peptide linker which links the heavy chain variable region and the light chain variable region may be those including any amino acids of 2 to 50, particularly 10 to 25 (e.g., 11, 12, 13, 14, 15, 16, 17, 18, 19, 20, 21, 22, 23, or 24) amino acids, and any kinds of amino acids may be included without any restrictions.

The antigen-binding fragments may be obtained using proteases (for example, a whole antibody is digested with papain to obtain Fab fragments, and is digested with pepsin to obtain F(ab')2 fragments), and may be prepared by a genetic recombinant technique.

In a particular embodiment, the anti-c-Met/anti-Her2 bispecific antibody comprises an anti-c-Met antibody, and scFv, (scFv)$_2$, Fab, Fab' or F(ab')2, for example, scFv of the anti-Her2 antibody linked to the C terminal of the anti-c-Met antibody. The scFv, (scFv)$_2$, Fab, Fab' or F(ab')2 of an anti-Her2 antibody may comprise a heavy chain variable region comprising the amino acid sequence of SEQ ID NO: 109 and a light chain variable region comprising the amino acid sequence of SEQ ID NO: 111.

In a particular embodiment, the anti-c-Met/anti-Her2 bispecific antibody comprises an anti-c-Met antibody, and scFv, (scFv)$_2$, Fab, Fab' or F(ab')2 of an anti-Her2 antibody comprising a heavy chain variable region comprising the amino acid sequence of SEQ ID NO: 109 and a light chain variable region comprising the amino acid sequence of SEQ ID NO: 111, linked to the C terminus of the anti-c-Met antibody.

The anti c-Met antibody may recognize a specific region of c-Met, e.g., a specific region in the SEMA domain, as an epitope. It may be any antibody or antigen-binding fragment that acts on c-Met to induce c-Met intracellular internalization and degradation.

c-Met, a receptor for hepatocyte growth factor (HGF), may be divided into three portions: extracellular, transmembrane, and intracellular. The extracellular portion is composed of an α-subunit and a β-subunit which are linked to each other through a disulfide bond. The extracellular portion contains a SEMA domain responsible for binding HGF, a PSI domain (plexin-semaphorins-integrin homology domain) and an IPT domain (immunoglobulin-like fold shared by plexins and transcriptional factors domain). The SEMA domain of c-Met protein may comprise the amino acid sequence of SEQ ID NO: 79, and is an extracellular domain that functions to bind HGF. A specific region of the SEMA domain, that is, a region comprising the amino acid sequence of SEQ ID NO: 71, which corresponds to a range from amino acid residues 106 to 124 of the amino acid sequence of the SEMA domain (SEQ ID NO: 79) of c-Met protein, is a loop region between the second and the third propellers within the epitopes of the SEMA domain. The region acts as an epitope for the specific anti-c-Met antibody of the present invention.

The term "epitope" as used herein, refers to an antigenic determinant, a part of an antigen recognized by an antibody. In one embodiment, the epitope may be a region including 5 or more contiguous (consecutive or non-consecutive) amino acid residues within the SEMA domain (SEQ ID NO: 79) of c-Met protein, for instance, 5 to 19 (e.g., 6, 7, 8, 9, 10, 11, 12, 13, 14, 15, 16, 17, or 18) contiguous amino acid residues within the amino acid sequence of SEQ ID NO: 71. For example, the epitope may be a polypeptide including 5 to 19 contiguous amino acids selected from among partial combinations of the amino acid sequence of SEQ ID NO: 71, wherein the polypeptide essentially includes the amino acid sequence of SEQ ID NO: 73 (EEPSQ) serving as an essential element for the epitope. For example, the epitope may be a polypeptide comprising, consisting essentially of, or consisting of the amino acid sequence of SEQ ID NO: 71, SEQ ID NO: 72, or SEQ ID NO: 73.

The epitope comprising the amino acid sequence of SEQ ID NO: 72 corresponds to the outermost part of the loop between the second and third propellers within the SEMA domain of a c-Met protein. The epitope comprising the amino acid sequence of SEQ ID NO: 73 is a site to which the antibody or antigen-binding fragment according to one embodiment most specifically binds.

Thus, the anti-c-Met antibody may specifically bind to an epitope which includes 5 to 19 contiguous amino acids selected from among partial combinations of the amino acid sequence of SEQ ID NO: 71, including SEQ ID NO: 73 as an essential element. For example, the anti-c-Met antibody may specifically bind to an epitope including the amino acid sequence of SEQ ID NO: 71, SEQ ID NO: 72, or SEQ ID NO: 73.

In one embodiment, the anti-c-Met antibody may be an antibody or an antigen-binding fragment thereof, which includes:

(i) a heavy chain variable region including at least one heavy chain complementarity determining region (CDR) selected from the group consisting of (a) a CDR-H1 comprising the amino acid sequence of SEQ ID NO: 4; (b) a CDR-H2 comprising the amino acid sequence of SEQ ID NO: 5, the amino acid sequence of SEQ ID NO: 2, or an amino acid sequence comprising 8-19 consecutive amino acids including amino acid residues from the $3^{rd}$ to $10^{th}$ positions of SEQ ID NO: 2; and (c) a CDR-H3 comprising the amino acid sequence of SEQ ID NO: 6, the amino acid sequence of SEQ ID NO: 85, or an amino acid sequence comprising 6-13 consecutive amino acids including amino acid residues from the $1^{st}$ to $6^{th}$ positions of the amino acid sequence of SEQ ID NO: 85; and (ii) a light chain variable region including at least one light chain complementarity determining region (CDR) selected from the group consisting of (a) a CDR-L1 comprising the amino acid sequence of SEQ ID NO: 7, (b) a CDR-L2 comprising the amino acid sequence of SEQ ID NO: 8, and (c) a CDR-L3 comprising the amino acid sequence of SEQ ID NO: 9, the amino acid sequence of SEQ ID NO: 86, or an amino acid sequence including 9-17 consecutive amino acids including amino acid residues from the $1^{st}$ to $9^{th}$ positions of the amino acid sequence of SEQ ID NO: 89.

Herein, the amino acid sequences of SEQ ID NOS: 4 to 9 are respectively represented by following Formulas I to VI, below:

Xaa$_1$-Xaa$_2$-Tyr-Tyr-Met-Ser (SEQ ID NO: 4), wherein Xaa$_1$ is absent or Pro or Ser, and Xaa$_2$ is Glu or Asp,    Formula I:

Arg-Asn-Xaa$_3$-Xaa$_4$-Asn-Gly-Xaa$_5$-Thr (SEQ ID NO: 5), wherein Xaa$_3$ is Asn or Lys, Xaa$_4$ is Ala or Val, and Xaa$_5$ is Asn or Thr,    Formula II:

Asp-Asn-Trp-Leu-Xaa$_6$-Tyr (SEQ ID NO: 6), wherein Xaa$_6$ is Ser or Thr,    Formula III:

Lys-Ser-Ser-Xaa$_7$-Ser-Leu-Leu-Ala-Xaa$_8$-Gly-Asn-Xaa$_9$-Xaa$_{10}$-Asn-Tyr-Leu-Ala (SEQ ID NO: 7), wherein Xaa$_7$ is His, Arg, Gln, or Lys, Xaa$_8$ is Ser or Trp, Xaa$_9$ is His or Gln, and Xaa$_{10}$ is Lys or Asn,    Formula IV:

Trp-Xaa$_{11}$-Ser-Xaa$_{12}$-Arg-Val-Xaa$_{13}$ (SEQ ID NO: 8), wherein Xaa$_{11}$ is Ala or Gly, Xaa$_{12}$ is Thr or Lys, and Xaa$_{13}$ is Ser or Pro, and    Formula V:

Xaa$_{14}$-Gln-Ser-Tyr-Ser-Xaa$_{15}$-Pro-Xaa$_{16}$-Thr (SEQ ID NO: 9), wherein Xaa$_{14}$ is Gly, Ala, or Gln, Xaa$_{15}$ is Arg, His, Ser, Ala, Gly, or Lys, and Xaa$_{16}$ is Leu, Tyr, Phe, or Met.    Formula VI:

In one embodiment, the CDR-H1 may comprise an amino acid sequence selected from the group consisting of SEQ ID NOS: 1, 22, 23, and 24. The CDR-H2 may comprise an amino acid sequence selected from the group consisting of SEQ ID NOS: 2, 25, and 26. The CDR-H3 may comprise an amino acid sequence selected from the group consisting of SEQ ID NOS: 3, 27, 28, and 85.

The CDR-L1 may comprise an amino acid sequence selected from the group consisting of SEQ ID NOS: 10, 29, 30, 31, 32, 33, and 106. The CDR-L2 may comprise an amino acid sequence selected from the group consisting of SEQ ID NOS: 11, 34, 35, and 36. The CDR-L3 may comprise an amino acid sequence selected from the group consisting of SEQ ID NOS: 12, 13, 14, 15, 16, 37, 86, and 89.

In another embodiment, the antibody or the antigen-binding fragment may comprise a heavy variable region including a polypeptide (CDR-H1) comprising an amino acid sequence selected from the group consisting of SEQ ID NOS: 1, 22, 23, and 24, a polypeptide (CDR-H2) comprising an amino acid sequence selected from the group consisting of SEQ ID NOS: 2, 25, and 26, and a polypeptide (CDR-H3) comprising an amino acid sequence selected from the group consisting of SEQ ID NOS: 3, 27, 28, and 85; and a light variable region comprising a polypeptide (CDR-L1) comprising an amino acid sequence selected from the group consisting of SEQ ID NOS: 10, 29, 30, 31, 32, 33 and 106, a polypeptide (CDR-L2) comprising an amino acid sequence selected from the group consisting of SEQ ID NOS: 11, 34, 35, and 36, and a polypeptide (CDR-L3) comprising an amino acid sequence selected from the group consisting of SEQ ID NOS 12, 13, 14, 15, 16, 37, 86, and 89.

Animal-derived antibodies produced by immunizing non-immune animals with a desired antigen generally invoke immunogenicity when injected into humans for the purpose of medical treatment, and thus chimeric antibodies have been developed to inhibit such immunogenicity. Chimeric antibodies are prepared by replacing constant regions of animal-derived antibodies that cause an anti-isotype response with constant regions of human antibodies by genetic engineering. Chimeric antibodies are considerably improved in an anti-isotype response compared to animal-derived antibodies, but animal-derived amino acids still have variable regions, so that chimeric antibodies have side effects with respect to a potential anti-idiotype response. Humanized antibodies have been developed to reduce such side effects. Humanized antibodies are produced by grafting complementarity determining regions (CDR) which serve an important role in antigen binding in variable regions of chimeric antibodies into a human antibody framework.

The most important thing in CDR grafting to produce humanized antibodies is choosing the optimized human antibodies for accepting CDRs of animal-derived antibodies. Antibody databases, analysis of a crystal structure, and technology for molecule modeling are used. However, even when the CDRs of animal-derived antibodies are grafted to the most optimized human antibody framework, amino acids positioned in a framework of the animal-derived CDRs affecting antigen binding are present. Therefore, in many cases, antigen binding affinity is not maintained, and thus application of additional antibody engineering technology for recovering the antigen binding affinity is necessary.

The anti c-Met antibodies may be mouse-derived antibodies, mouse-human chimeric antibodies, humanized antibodies, or human antibodies. The antibodies or antigen-binding fragments thereof may be isolated from (not originally present in) a living body or non-naturally occurring. The antibodies or antigen-binding fragments thereof may be recombinant or synthetic.

An intact antibody includes two full-length light chains and two full-length heavy chains, in which each light chain is linked to a heavy chain by disulfide bonds. The antibody includes a heavy chain constant region and a light chain constant region. The heavy chain constant region is of a gamma (γ), mu (μ), alpha (α), delta (δ), or epsilon (ε) type, which may be further categorized as gamma 1 (γ1), gamma 2(γ2), gamma 3(γ3), gamma 4(γ4), alpha 1(α1), or alpha 2(α2). The light chain constant region is of either a kappa (κ) or lambda (λ) type.

As used herein, the term "heavy chain" refers to full-length heavy chain, and fragments thereof, including a variable region $V_H$ that includes amino acid sequences sufficient to provide specificity to antigens, and three constant regions, $C_{H1}$, $C_{H2}$, and $C_{H3}$, and a hinge. The term "light chain" refers to a full-length light chain and fragments thereof, including a variable region $V_L$ that includes amino acid sequences sufficient to provide specificity to antigens, and a constant region $C_L$.

The term "complementarity determining region (CDR)" refers to an amino acid sequence found in a hyper variable region of a heavy chain or a light chain of immunoglobulin. The heavy and light chains may respectively include three CDRs (CDRH1, CDRH2, and CDRH3; and CDRL1, CDRL2, and CDRL3). The CDRs may provide contact residues that play an important role in the binding of antibodies to antigens or epitopes. The terms "specifically binding" and "specifically recognized" are well known to one of ordinary skill in the art, and indicate that an antibody and an antigen specifically interact with each other to lead to an immunological activity.

The term "antigen-binding fragment" used herein refers to fragments of an intact immunoglobulin including portions of a polypeptide that comprises antigen-binding regions having the ability to specifically bind to the antigen. In one embodiment, the antibody may be an antigen-binding fragment selected from the group consisting of scFv, (scFv)$_2$, Fab, Fab', and F(ab')2.

Among the antigen-binding fragments, Fab that includes light chain and heavy chain variable regions, a light chain constant region, and a first heavy chain constant region $C_{H1}$, includes one antigen-binding site.

The Fab' fragment is different from the Fab fragment, in that Fab' includes a hinge region with at least one cysteine residue at the C-terminal of $C_{H1}$.

The F(ab')2 antibody is formed through disulfide bridging of the cysteine residues in the hinge region of the Fab' fragment. Fv is the smallest antibody fragment with only a heavy chain variable region and a light chain variable region. Recombination techniques of generating the Fv fragment are widely known in the art.

Two-chain Fv includes a heavy chain variable region and a light chain region which are linked by a non-covalent bond. Single-chain Fv generally includes a heavy chain variable region and a light chain variable region which are linked by a covalent bond via a peptide linker or linked at the C-terminals to have a dimer structure like the two-chain Fv.

The antigen-binding fragments may be attainable using protease (for example, the Fab fragment may be obtained by restricted cleavage of a whole antibody with papain, and the F(ab')2 fragment may be obtained by cleavage with pepsin), or may be prepared by using a genetic recombination technique.

The term "hinge region," as used herein, refers to a region between CH1 and CH2 domains within the heavy chain of an antibody which functions to provide flexibility for the antigen-binding site.

When an animal antibody undergoes a chimerization process, the IgG1 hinge of animal origin may be replaced with a human IgG1 hinge or IgG2 hinge while the disulfide bridges between two heavy chains are reduced from three to two in number. In addition, an animal-derived IgG1 hinge is shorter than a human IgG1 hinge. Accordingly, the rigidity of the hinge is changed. Thus, a modification of the hinge region may bring about an improvement in the antigen binding efficiency of the humanized antibody. The modification of the hinge region through amino acid deletion, addition, or substitution is well-known to those skilled in the art.

In one embodiment, the anti-c-Met antibody or an antigen-binding fragment thereof may be modified by the deletion, insertion, addition, or substitution of at least one (e.g., two, three, four, five, six, seven, eight, nine, or ten) amino acid residue of the amino acid sequence of the hinge region so that it exhibits enhanced antigen-binding efficiency. For example, the antibody may include a hinge region including the amino acid sequence of SEQ ID NO: 100 (U7-HC6), 101 (U6-HC7), 102 (U3-HC9), 103 (U6-HC8), or 104 (U8-HC5), or a hinge region including the amino acid sequence of SEQ ID NO: 105 (non-modified human hinge). Preferably, the hinge region includes the amino acid sequence of SEQ ID NO: 100 or 101.

In one embodiment of the anti-c-Met antibody or antigen-binding fragment, the variable domain of the heavy chain comprises the amino acid sequence of SEQ ID NO: 17, 74, 87, 90, 91, 92, 93, or 94 and the variable domain of the light chain comprises the amino acid sequence of SEQ ID NO: 18, 19, 20, 21, 75, 88, 95, 96, 97, 98, 99, or 107.

In one embodiment, the anti-c-Met antibody may be a monoclonal antibody.

The monoclonal antibody may be produced by the hybridoma cell line deposited with the Korean Cell Line Research Foundation, an international depositary authority located at Yungun-Dong, Jongno-Gu, Seoul, Korea, on Oct. 9, 2009, under Accession No. KCLRF-BP-00220, which binds specifically to the extracellular region of c-Met protein (refer to Korean Patent Publication No. 2011-0047698, the entire disclosure of which is incorporated herein by reference). The anti-c-Met antibody may include all the antibodies defined in Korean Patent Publication No. 2011-0047698.

In the anti-c-Met antibody, the portion of the light chain and the heavy chain portion excluding the CDRs, the light chain variable region, and the heavy chain variable region refers to the light chain constant region and the heavy chain constant region. The heavy chain constant region, the light chain constant region, and/or the region other than the CDR region, the heavy chain variable region, or the light chain variable region may be originated from any subtype of immunoglobulin (e.g., IgA, IgD, IgE, IgG (IgG1, IgG2, IgG3, IgG4), IgM, etc.).

By way of further example, the anti-c-Met antibody or the antibody fragment may include:

(a) a heavy chain comprising an amino acid sequence selected from the group consisting of the amino acid sequence of SEQ ID NO: 62 (wherein the amino acid sequence from amino acid residues from the $1^{st}$ to $17^{th}$ positions is a signal peptide), the amino acid sequence from the $18^{th}$ to $462^{nd}$ positions of SEQ ID NO: 62, the amino acid sequence of SEQ ID NO: 64 (wherein the amino acid sequence from the $1^{st}$ to $17^{th}$ positions is a signal peptide), the amino acid sequence from the $18^{th}$ to $461^{st}$ positions of SEQ ID NO: 64, the amino acid sequence of SEQ ID NO: 66 (wherein the amino acid sequence from the $1^{st}$ to $17^{th}$ positions is a signal peptide), and the amino acid sequence from the $18^{th}$ to $460^{th}$ positions of SEQ ID NO: 66; and (b) a light chain comprising an amino acid sequence selected from the group consisting of the amino acid sequence of SEQ ID NO: 68 (wherein the amino acid sequence from the $1^{st}$ to $20^{th}$ positions is a signal peptide), the amino acid sequence from the $21^{st}$ to $240^{th}$ positions of SEQ ID NO: 68, the amino acid sequence of SEQ ID NO: 70 (wherein the amino acid sequence from the $1^{st}$ to $20^{th}$ positions is a signal peptide), the amino acid sequence from the $21^{st}$ to $240^{th}$ positions of SEQ ID NO: 70, and the amino acid sequence of SEQ ID NO: 108.

For example, the anti-c-Met antibody may be selected from the group consisting of:

(i) an antibody comprising (a) a heavy chain comprising the amino acid sequence of SEQ ID NO: 62 or the amino acid sequence from the $18^{th}$ to $462^{nd}$ positions of SEQ ID NO: 62 and (b) a light chain comprising the amino acid sequence of SEQ ID NO: 68 or the amino acid sequence from the $21^{st}$ to $240^{th}$ positions of SEQ ID NO: 68;

(ii) an antibody comprising (a) a heavy chain comprising the amino acid sequence of SEQ ID NO: 64 or the amino acid sequence from the $18^{th}$ to $461^{st}$ positions of SEQ ID NO: 64 and (b) a light chain including the amino acid sequence of SEQ ID NO: 68 or the amino acid sequence from the $21^{st}$ to $240^{th}$ positions of SEQ ID NO: 68;

(iii) an antibody comprising (a) a heavy chain comprising the amino acid sequence of SEQ ID NO: 66 or the amino acid sequence from the $18^{th}$ to $460^{th}$ positions of SEQ ID NO: 66 and (b) a light chain comprising the amino acid sequence of SEQ ID NO: 68 or the amino acid sequence from the $21^{st}$ to $240^{th}$ positions of SEQ ID NO: 68;

(iv) an antibody comprising (a) a heavy chain comprising the amino acid sequence of SEQ ID NO: 62 or the amino acid sequence from the $18^{th}$ to $462^{nd}$ positions of SEQ ID NO: 62 and (b) a light chain including the amino acid sequence of SEQ ID NO: 70 or the amino acid sequence from the $21^{st}$ to $240^{th}$ positions of SEQ ID NO: 70;

(v) an antibody comprising a heavy chain comprising (a) the amino acid sequence of SEQ ID NO: 64 or the amino acid sequence from the $18^{th}$ to $461^{st}$ positions of SEQ ID NO: 64 and (b) a light chain comprising the amino acid sequence of SEQ ID NO: 70 or the amino acid sequence from the $21^{st}$ to $240^{th}$ positions of SEQ ID NO: 70;

(v) an antibody comprising (a) a heavy chain comprising the amino acid sequence of SEQ ID NO: 66 or the amino acid sequence from the $18^{th}$ to $460^{th}$ positions of SEQ ID NO: 66 and (b) a light chain comprising the amino acid sequence of SEQ ID NO: 70 or the amino acid sequence from the $21^{st}$ to $240^{th}$ positions of SEQ ID NO: 70;

(vi) an antibody comprising (a) a heavy chain comprising the amino acid sequence of SEQ ID NO: 62 or the amino acid sequence from the $18^{th}$ to $462^{nd}$ positions of SEQ ID NO: 62 and (b) a light chain comprising the amino acid sequence of SEQ ID NO: 108;

(vii) an antibody comprising (a) a heavy chain comprising the amino acid sequence of SEQ ID NO: 64 or the amino acid sequence from the $18^{th}$ to $461^{st}$ positions of SEQ ID NO: 64 and (b) a light chain comprising the amino acid sequence of SEQ ID NO: 108; and (viii) an antibody comprising (a) a heavy chain comprising the amino acid sequence of SEQ ID NO: 66 or the amino acid sequence from the $18^{th}$ to $460^{th}$ positions of SEQ ID NO: 66 and (b) a light chain comprising the amino acid sequence of SEQ ID NO: 108.

The polypeptide comprising the amino acid sequence of SEQ ID NO: 70 is a light chain including human kappa (κ) constant region, and the polypeptide comprising the amino acid sequence of SEQ ID NO: 68 is a polypeptide obtained by replacing histidine at position 62 (corresponding to position 36 of SEQ ID NO: 68 according to kabat numbering) of the polypeptide comprising the amino acid sequence of SEQ ID NO: 70 with tyrosine. The production yield of the antibodies may be increased by the replacement. The polypeptide comprising the amino acid sequence of SEQ ID NO: 108 is a polypeptide obtained by replacing serine at position 32 (position 27e according to kabat numbering in the amino acid sequence from amino acid residues 21 to 240 of SEQ ID NO: 68; positioned within CDR-L1) of SEQ ID NO: 108 with tryptophan. By such replacement, antibodies and antibody fragments including such sequences exhibit increased activities, such as c-Met biding affinity, c-Met degradation activity, Akt phosphorylation inhibition, and the like.

In another embodiment, the anti c-Met antibody may include a light chain complementarity determining region comprising the amino acid sequence of SEQ ID NO: 106, a light chain variable region comprising the amino acid sequence of SEQ ID NO: 107, or a light chain comprising the amino acid sequence of SEQ ID NO: 108.

The anti-c-Met/anti-Her2 bispecific antibody can not only inhibit the activity of c-Met and Her2 by the internalization and degradation activity of anti-c-Met antibody but also fundamentally block them by reducing the total amounts of c-Met and Her2 by the degradation thereof. Accordingly, the anti-c-Met/anti-Her2 bispecific antibody can obtain efficient effects even when applied to patients who have developed resistance against pre-existing anti-Her2 antibodies.

An embodiment provides a pharmaceutical composition including an anti-c-Met/anti-Her2 bispecific antibody (e.g., in combination with a pharmaceutically acceptable carrier).

Another embodiment provides a method for preventing and/or treating cancer including administering a pharmaceutically effective amount of the anti-c-Met/anti-Her2 bispecific antibody (alone or in combination with a pharmaceutically acceptable carrier) to a patient in need of the prevention and/or treatment of cancer. The method may further include the step of identifying the patient in need of the prevention and/or treatment of cancer prior to the step of administering. Another embodiment provides a use of the anti-c-Met/anti-Her2 bispecific antibody for the prevention and/or treatment of cancer.

The cancer to be prevented and/or treated by the anti-c-Met/anti-Her2 bispecific antibody may be associated with over-expression and/or abnormal activation of c-Met and/or Her2. The cancer may include solid cancers and blood cancers. The cancer may be, but not limited to, one or more selected from the group consisting of squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastric cancer, gastrointestinal cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, head or neck cancer, and brain cancer. The cancer may include metastatic cancers as well as primary cancers. Especially, the cancer may be a cancer having resistance against pre-existing anticancer drugs, for example, antagonists against Her2.

The prevention and/or treatment of cancer may include cancer cell death, inhibition of cancer cell proliferation, improvement of symptoms associated with cancer, inhibition of metastasis of cancer, etc.

The pharmaceutical composition may be provided along with a pharmaceutically acceptable carrier, diluent, and/or excipient, in addition to a pharmaceutically effective amount of the anti-c-Met/anti-Her2 bispecific antibody.

The pharmaceutically acceptable carrier to be included in the composition may be those commonly used for the formulation of antibodies, which may be one or more selected from the group consisting of lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but are not limited thereto. The pharmaceutical composition may further include one or more selected from the group consisting of a lubricant, a wetting agent, a sweetener, a flavor enhancer, an emulsifying agent, a suspension agent, and preservative.

The pharmaceutical composition may be administered orally or parenterally. The parenteral administration may include intravenous injection, subcutaneous injection, muscular injection, intraperitoneal injection, endothelial administration, local administration, intranasal administration, intrapulmonary administration, and rectal administration. Since oral administration leads to digestion of proteins or peptides, an active ingredient in the compositions for oral administration must be coated or formulated to prevent digestion in stomach. In addition, the compositions may be administered using an optional device that enables an active substance to be delivered to target cells.

A suitable dosage of the pharmaceutical composition may be prescribed in a variety of ways, depending on factors such as formulation methods, administration methods, age of patients, body weight, gender, pathologic conditions, diets, administration time, administration route, excretion speed, and reaction sensitivity. A desirable dosage of the pharmaceutical composition may be in the range of about 0.001 to 100 mg/kg (body weight) per day for an adult. The term "the pharmaceutically effective amount" as used in this specification refers to an amount at which each active ingredient can exert pharmaceutically significant effects in preventing or treating cancer.

The pharmaceutical composition may be formulated with a pharmaceutically acceptable carrier and/or excipient into a unit or a multiple dosage form by a method easily carried out by a skilled person in the pertinent art. The dosage form may be a solution in oil or an aqueous medium, a suspension, syrup, an emulsifying solution, an extract, powder, granules, a tablet, or a capsule, and may further include a dispersing or a stabilizing agent.

In addition, the pharmaceutical composition may be administered as an individual drug, or together with other drugs, and may be administered sequentially or simultaneously with pre-existing drugs.

Since the pharmaceutical composition includes an antibody or an antigen-binding fragment thereof, it may be formulated as an immunoliposome. The liposome containing the antibody may be prepared using a well-known method in the pertinent art. The immunoliposome is a lipid composition including phosphatidylcholine, cholesterol, and polyethyleneglycol-derivatized phosphatidylethanolamine, and may be prepared by a reverse phase evaporation method. For example, Fab' fragments of an antibody may be conjugated to the liposome through a disulfide exchange reaction. A chemical drug such as doxorubicin may be additionally included in the liposome.

The subjects to which the pharmaceutical composition is administered or patients to which the preventing and/treating method is administered may be mammals, for example, primates such as humans and monkeys, or rodents such as rats and mice, but are not limited thereto, and they may be cancer patients having resistance against pre-existing anticancer drugs, for example, antagonists against the target cell membrane proteins.

Herceptin, which is a typical target drug recognizing only Her2 which is a typical target expressed abundantly in cancer cells, induces the over-expression and activation of cMet and thus causes cancer cells to acquire resistance against drugs, whereby the therapeutic effects could be reduced. In this regard, the inventors have verified that a bispecific antibody recognizing cMet and Her2 at the same time suppresses the over-expression of cMet which is a cause of resistance against drugs and thus blocks its signal transduction in advance to prevent the development of resistance and shows excellent cancer cell suppression effects even in cancer cells having resistance. The bispecific cMet/Her2 antibody which is the subject matter of the present invention exceeds the efficiency of the pre-existing single target drugs and at the same time, it is expected to exhibit effects even in cancers where the pre-existing drugs exerted no effects.

Hereafter, the present invention will be described in detail by examples.

The following examples are intended merely to illustrate the invention and are not construed to restrict the invention.

EXAMPLES

Reference Example 1: Construction of Anti-c-Met Antibody 1.1. Production of "AbF46", a Mouse Antibody to c-Met
1.1.1. Immunization of Mouse To obtain immunized mice necessary for the development of a hybridoma cell line, each of five BALB/c mice (Japan SLC, Inc.), 4 to 6 weeks old, was intraperitoneally injected with a mixture of 100 µg of human c-Met/Fc fusion protein (R&D Systems) and one volume of complete Freund's adjuvant. Two weeks after the injection, a second intraperitoneal injection was conducted on the same mice with a mixture of 50 µg of human c-Met/Fc protein and one volume of incomplete Freund's adjuvant. One week after the second immunization, the immune response was finally boosted. Three days later, blood was taken from the tails of the mice and the sera were 1/1000 diluted in PBS and used to examine a titer of antibody to c-Met by ELISA. Mice found to have a sufficient antibody titer were selected for use in the cell fusion process.

1.1.2. Cell Fusion and Production of Hybridoma

Three days before cell fusion, BALB/c mice (Japan SLC, Inc.) were immunized with an intraperitoneal injection of a mixture of 50 µg of human c-Met/Fc fusion protein and one volume of PBS. The immunized mice were anesthetized before excising the spleen from the left half of the body. The spleen was meshed to separate splenocytes which were then suspended in a culture medium (DMEM, GIBCO, Invitrogen). The cell suspension was centrifuged to recover the cell layer. The splenocytes thus obtained ($1 \times 10^8$ cells) were mixed with myeloma cells (Sp2/0) ($1 \times 10^8$ cells), followed by spinning to give a cell pellet. The cell pellet was slowly suspended, treated with 45% polyethylene glycol (PEG) (1 mL) in DMEM for 1 min at 37° C., and supplemented with 1 mL of DMEM. To the cells was added 10 mL of DMEM over 10 min, after which incubation was conducted in a water bath at 37° C. for 5 min. Then the cell volume was adjusted to 50 mL before centrifugation. The cell pellet thus formed was resuspended at a density of $1$-$2 \times 10^5$ cells/mL in a selection medium (HAT medium) and 0.1 mL of the cell suspension was allocated to each well of 96-well plates which were then incubated at 37° C. in a $CO_2$ incubator to establish a hybridoma cell population.

1.1.3. Selection of Hybridoma Cells Producing Monoclonal Antibodies to c-Met Protein From the hybridoma cell population established in Reference Example 1.1.2, hybridoma cells which showed a specific response to c-Met protein were screened by ELISA using human c-Met/Fc fusion protein and human Fc protein as antigens.

Human c-Met/Fc fusion protein was seeded in an amount of 50 µL (2 µg/mL)/well to microtiter plates and allowed to adhere to the surface of each well. The antibody that remained unbound was removed by washing. For use in selecting the antibodies that do not bind c-Met but recognize Fc, human Fc protein was attached to the plate surface in the same manner.

The hybridoma cell culture obtained in Reference Example 1.1.2 was added in an amount of 50 µL to each well of the plates and incubated for 1 hour. The cells remaining unreacted were washed out with a sufficient amount of Tris-buffered saline and TWEEN 20 (polysorbate 20) (TBST). Goat anti-mouse IgG-horseradish peroxidase (HRP) was added to the plates and incubated for 1 hour at room temperature. The plates were washed with a sufficient amount of TBST, followed by reacting the peroxidase with a substrate (OPD). Absorbance at 450 nm was measured on an ELISA reader.

Hybridoma cell lines which secrete antibodies that specifically and strongly bind to human c-Met but not human Fc were selected repeatedly. From the hybridoma cell lines obtained by repeated selection, a single clone producing a monoclonal antibody was finally separated by limiting dilution. The single clone of the hybridoma cell line producing the monoclonal antibody was deposited with the Korean Cell Line Research Foundation, an international depository authority located at Yungun-Dong, Jongno-Gu, Seoul, Korea, on Oct. 9, 2009, with Accession No. KCLRF-BP-00220 according to the Budapest Treaty (refer to Korean Patent Laid-Open Publication No. 2011-0047698).

1.1.4. Production and Purification of Monoclonal Antibody

The hybridoma cell line obtained in Reference Example 1.1.3 was cultured in a serum-free medium, and the monoclonal antibody (AbF46) was produced and purified from the cell culture.

First, the hybridoma cells cultured in 50 mL of a medium (DMEM) supplemented with 10% (v/v) fetal bovine serum (FBS) were centrifuged and the cell pellet was washed twice or more with 20 mL of PBS to remove the FBS therefrom. Then, the cells were resuspended in 50 mL of DMEM and incubated for 3 days at 37° C. in a $CO_2$ incubator.

After the cells were removed by centrifugation, the supernatant was stored at 4° C. before use or immediately used for the separation and purification of the antibody. An AKTA fast protein liquid chromatography system (GE Healthcare) equipped with an affinity column (Protein G agarose column; Pharmacia, USA) was used to purify the antibody from 50 to 300 mL of the supernatant, followed by concentration with a filter (Amicon). The antibody in phosphate buffered saline (PBS) was stored before use in the following examples.

1.2. Construction of chAbF46, a Chimeric Antibody to c-Met

A mouse antibody is apt to elicit immunogenicity in humans. To solve this problem, chAbF46, a chimeric antibody, was constructed from the mouse antibody AbF46 produced in Experimental Example 1.1.4 by replacing the constant region, but not the variable region responsible for antibody specificity, with an amino sequence of the human IgG1 antibody.

In this regard, a gene was designed to include the nucleotide sequence of "EcoRI-signal sequence-VH-NheI-CH-TGA-XhoI" (SEQ ID NO: 38) for a heavy chain and the nucleotide sequence of "EcoRI-signal sequence-VL-BsiWI- CL-TGA-XhoI" (SEQ ID NO: 39) for a light chain and synthesized. Then, a DNA fragment having the heavy chain nucleotide sequence (SEQ ID NO: 38) and a DNA fragment having the light chain nucleotide sequence (SEQ ID NO: 39) were digested with EcoRI (NEB, R0101S) and XhoI (NEB, R0146S) before cloning into a vector from the pOptiVEC™-TOPO TA Cloning Kit enclosed in an OptiCHO™ Antibody Express Kit (Cat no. 12762-019, Invitrogen), and a vector from the pcDNA™3.3-TOPO TA Cloning Kit (Cat no. 8300-01), respectively.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5 \times 10^5$ cells/mL, and after 24 hours, when the cell number reached to $1 \times 10^6$ cells/mL, the transient expression was performed. A transfection was performed by a liposomal reagent method using Freestyle™ MAX reagent (Invitrogen), wherein in a 15 mL tube, the DNA was provided in the mixture ratio of 1:1 (heavy chain DNA:light chain DNA) and mixed with 2 ml of OptiPro™ SFM (Invitrogen) (A). In another 15 ml tube, 100 µL of Freestyle™ MAX reagent and 2 mL of OptiPro™ SFM were mixed (B). This was followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

Afterwards, the cells were incubated in DMEM supplemented with 10% (v/v) FBS for 5 hours at 37° C. under a 5% $CO_2$ condition and then in FBS-free DMEM for 48 hours at 37° C. under a 5% $CO_2$ condition.

After centrifugation, the supernatant was applied to AKTA prime fast protein liquid chromatography (GE Healthcare) to purify the antibody. In this regard, 100 mL of the supernatant was loaded at a flow rate of 5 mL/min to AKTA Prime fast protein liquid chromatography equipped with a Protein A column (GE Healthcare, 17-0405-03), followed by elution with an IgG elution buffer (Thermo Scientific, 21004). The buffer was exchanged with PBS to purify a chimeric antibody AbF46 (hereinafter referred to as "chAbF46").

1.3. Construction of Humanized Antibody huAbF46 from Chimeric Antibody chAbF46

1.3.1. Heavy Chain Humanization

To design two domains H1-heavy and H3-heavy, human germline genes which share the highest identity/homology with the VH gene of the mouse antibody AbF46 purified in Reference Example 1.2 were analyzed. An Ig BLAST (IgBLAST online database tool, maintained by National Center for Biotechnology Information (NCBI), Bethesda, Md.) result revealed that VH3-71 has an identity/identity/homology of 83% at the amino acid level. CDR-H1, CDR-H2, and CDR-H3 of the mouse antibody AbF46 were defined according to Kabat numbering. A design was made to introduce the CDRs of the mouse antibody AbF46 into the framework of VH3-71. Hereupon, back mutations to the amino acid sequence of the mouse AbF46 were conducted at positions 30 (S→T), 48 (V→L), 73 (D→N), and 78 (T→L). Then, H1 was further mutated at positions 83 (R→K) and 84 (A→T) to finally establish H1-heavy (SEQ ID NO: 40) and H3-heavy (SEQ ID NO: 41).

For use in designing H4-heavy, human antibody frameworks were analyzed by a BLAST search. The result revealed that the VH3 subtype, known to be most stable, is very similar in framework and sequence to the mouse antibody AbF46. CDR-H1, CDR-H2, and CDR-H3 of the mouse antibody AbF46 were defined according to Kabat numbering and introduced into the VH3 subtype to construct H4-heavy (SEQ ID NO: 42).

1.3.2. Light Chain Humanization

To design two domains H1-light (SEQ ID NO: 43) and H2-light (SEQ ID NO: 44), human germline genes which share the highest identity/homology with the VH gene of the mouse antibody AbF46 were analyzed. An Ig BLAST search result revealed that VK4-1 has an identity/homology of 75% at the amino acid level. CDR-L1, CDR-L2, and CDR-L3 of the mouse antibody AbF46 were defined according to Kabat numbering. A design was made to introduce the CDRs of the mouse antibody AbF46 into the framework of VK4-1. Hereupon, back mutations to the amino acid sequence of the mouse AbF46 were conducted at positions 36 (Y→H), 46 (L→M), and 49 (Y→I). Only one back mutation was conducted at position 49 (Y→I) on H2-light.

To design H3-light (SEQ ID NO: 45), human germline genes which share the highest identity/homology with the VL gene of the mouse antibody AbF46 were analyzed by a search for BLAST. As a result, VK2-40 was selected. VL and VK2-40 of the mouse antibody AbF46 were found to have an identity/homology of 61% at an amino acid level. CDR-L1, CDR-L2, and CDR-L3 of the mouse antibody were defined according to Kabat numbering and introduced into the framework of VK4-1. Back mutations were conducted at positions 36 (Y→H), 46 (L→M), and 49 (Y→I) on H3-light.

For use in designing H4-light (SEQ ID NO: 46), human antibody frameworks were analyzed. A Blast search revealed that the Vk1 subtype, known to be the most stable, is very similar in framework and sequence to the mouse antibody AbF46. CDR-L1, CDR-L2, and CDR-L3 of the mouse antibody AbF46 were defined according to Kabat numbering and introduced into the Vk1 subtype. Hereupon, back mutations were conducted at positions 36 (Y→H), 46 (L→M), and 49 (Y→I) on H4-light.

Thereafter, DNA fragments having the heavy chain nucleotide sequences (H1-heavy: SEQ ID NO: 47, H3-heavy: SEQ ID NO: 48, H4-heavy: SEQ ID NO: 49) and DNA fragments having the light chain nucleotide sequences (H1-light: SEQ ID NO: 50, H2-light: SEQ ID NO: 51, H3-light: SEQ ID NO: 52, H4-light: SEQ ID NO: 53) were digested with EcoRI (NEB, R0101S) and XhoI (NEB, R0146S) before cloning into a vector from the pOptiVEC™-TOPO TA Cloning Kit enclosed in an OptiCHO™ Antibody Express Kit (Cat no. 12762-019, Invitrogen) and a vector from the pcDNA™3.3-TOPO TA Cloning Kit (Cat no. 8300-01), respectively, so as to construct recombinant vectors for expressing a humanized antibody.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5 \times 10^5$ cells/mL, and after 24 hours, when the cell number reached to $1 \times 10^6$ cells/mL, the transient expression was performed. A transfection was performed by a liposomal reagent method using Freestyle™ MAX reagent (Invitrogen), wherein in a 15 mL tube, the DNA was provided in the mixture ratio of 1:1 (heavy chain DNA:light chain DNA) and mixed with 2 mL of OptiPro™ SFM (Invitrogen) (A). In another 15 mL tube, 100 μL of Freestyle™ MAX reagent and 2 mL of OptiPro™ SFM were mixed (B). This was followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime fast protein liquid chromatography (GE Healthcare) to purify the antibody. In this regard, 100 mL of the supernatant was loaded at a flow rate of 5 mL/min to AKTA Prime fast protein liquid chromatography equipped with a Protein A column (GE Healthcare, 17-0405-03), followed by elution with an IgG elution buffer (Thermo Scientific, 21004). The buffer was exchanged with PBS to purify a humanized antibody AbF46 (hereinafter referred to as "huAbF46"). The humanized antibody huAbF46 used in the following examples included a combination of H4-heavy (SEQ ID NO: 42) and H4-light (SEQ ID NO: 46).

1.4. Construction of scFV Library of huAbF46 Antibody

For use in constructing an scFv of the huAbF46 antibody from the heavy and light chain variable regions of the huAbF46 antibody, a gene was designed to have the structure of "VH-linker-VL" for each of the heavy and the light chain variable region, with the linker including the amino acid sequence "GLGGLGGGGSGGGGSGGSSGVGS" (SEQ ID NO: 54). A polynucleotide sequence (SEQ ID NO: 55) encoding the designed scFv of huAbF46 was synthesized in BIONEER and an expression vector for the polynucleotide had the nucleotide sequence of SEQ ID NO: 56.

After expression, the product was found to exhibit specificity to c-Met.

1.5. Construction of Library Genes for Affinity Maturation
1.5.1. Selection of Target CDRs and Synthesis of Primers The affinity maturation of huAbF46 was achieved. First, six complementary determining regions (CDRs) were defined according to Kabat numbering. The CDRs are given in Table 1, below.

TABLE 1

| CDR | Amino Acid Sequence |
| --- | --- |
| CDR-H1 | DYYMS (SEQ ID NO: 1) |
| CDR-H2 | FIRNKANGYTTEYSASVKG (SEQ ID NO: 2) |
| CDR-H3 | DNWFAY (SEQ ID NO: 3) |
| CDR-L1 | KSSQSLLASGNQNNYLA (SEQ ID NO: 10) |
| CDR-L2 | WASTRVS (SEQ ID NO: 11) |
| CDR-L3 | QQSYSAPLT (SEQ ID NO: 12) |

For use in the introduction of random sequences into the CDRs of the antibody, primers were designed as follows. Conventionally, N codons were utilized to introduce bases at the same ratio (25% A, 25% G, 25% C, 25% T) into desired sites of mutation. In this experiment, the introduction of random bases into the CDRs of huAbF46 was conducted in such a manner that, of the three nucleotides per codon in the wild-type polynucleotide encoding each CDR, the first and second nucleotides conserved over 85% of the entire sequence while the other three nucleotides were introduced at the same percentage (each 5%) and that the same possibility was imparted to the third nucleotide (33% G, 33% C, 33% T).

1.5.2. Construction of a Library of huAbF46 Antibodies and Affinity for c-Met

The construction of antibody gene libraries through the introduction of random sequences was carried out using the primers synthesized in the same manner as in Reference Example 1.5.1. Two PCR products were obtained using a polynucleotide covering the scFV of huAbF46 as a template, and were subjected to overlap extension PCR to give scFv library genes for huAbF46 antibodies in which only desired CDRs were mutated. Libraries targeting each of the six CDRs prepared from the scFV library genes were constructed.

The affinity for c-Met of each library was compared to that of the wildtype. Most libraries were lower in affinity for c-Met, compared to the wild-type. The affinity for c-Met was retained in some mutants.

1.6. Selection of Antibody with Improved Affinity from Libraries

After maturation of the affinity of the constructed libraries for c-Met, the nucleotide sequence of scFv from each clone was analyzed. The nucleotide sequences thus obtained are summarized in Table 2 and were converted into IgG forms. Four antibodies which were respectively produced from clones L3-1, L3-2, L3-3, and L3-5 were used in the subsequent experiments.

TABLE 2

| Clone | Library constructed | CDR Sequence |
| --- | --- | --- |
| H11-4 | CDR-H1 | PEYYMS (SEQ ID NO: 22) |
| YC151 | CDR-H1 | PDYYMS (SEQ ID NO: 23) |
| YC193 | CDR-H1 | SDYYMS (SEQ ID NO: 24) |
| YC244 | CDR-H2 | RNNANGNT (SEQ ID NO: 25) |
| YC321 | CDR-H2 | RNKVNGYT (SEQ ID NO: 26) |
| YC354 | CDR-H3 | DNWLSY (SEQ ID NO: 27) |
| YC374 | CDR-H3 | DNWLTY (SEQ ID NO: 28) |
| L1-1 | CDR-L1 | KSSHSLLASGNQNNYLA (SEQ ID NO: 29) |
| L1-3 | CDR-L1 | KSSRSLLSSGNHKNYLA (SEQ ID NO: 30) |
| L1-4 | CDR-L1 | KSSKSLLASGNQNNYLA (SEQ ID NO: 31) |
| L1-12 | CDR-L1 | KSSRSLLASGNQNNYLA (SEQ ID NO: 32) |
| L1-22 | CDR-L1 | KSSHSLLASGNQNNYLA (SEQ ID NO: 33) |
| L2-9 | CDR-L2 | WASKRVS (SEQ ID NO: 34) |
| L2-12 | CDR-L2 | WGSTRVS (SEQ ID NO: 35) |
| L2-16 | CDR-L2 | WGSTRVP (SEQ ID NO: 36) |
| L3-1 | CDR-L3 | QQSYSRPYT (SEQ ID NO: 13) |
| L3-2 | CDR-L3 | GQSYSRPLT (SEQ ID NO: 14) |
| L3-3 | CDR-L3 | AQSYSHPFS (SEQ ID NO: 15) |

TABLE 2-continued

| Clone | Library constructed | CDR Sequence |
|---|---|---|
| L3-5 | CDR-L3 | QQSYSRPFT (SEQ ID NO: 16) |
| L3-32 | CDR-L3 | QQSYSKPFT (SEQ ID NO: 37) |

1.7. Conversion of Selected Antibodies into IgG

Respective polynucleotides encoding heavy chains of the four selected antibodies were designed to have the structure of "EcoRI-signal sequence-VH-NheI-CH-XhoI" (SEQ ID NO: 38). The heavy chains of huAbF46 antibodies were used as they were because their amino acids were not changed during affinity maturation. In the case of the hinge region, however, the U6-HC7 hinge (SEQ ID NO: 57) was employed instead of the hinge of human IgG1. Genes also were designed to have the structure of "EcoRI-signal sequence-VL-BsiWI-CL-XhoI" for the light chain. Polypeptides encoding light chain variable regions of the four antibodies which were selected after the affinity maturation were synthesized in BIONEER. Then, a DNA fragment having the heavy chain nucleotide sequence (SEQ ID NO: 38) and DNA fragments having the light chain nucleotide sequences (DNA fragment comprising L3-1-derived CDR-L3: SEQ ID NO: 58, DNA fragment comprising L3-2-derived CDR-L3: SEQ ID NO: 59, DNA fragment comprising L3-3-derived CDR-L3: SEQ ID NO: 60, and DNA fragment comprising L3-5-derived CDR-L3: SEQ ID NO: 61) were digested with EcoRI (NEB, R0101S) and XhoI (NEB, R0146S) before cloning into a vector from the pOptiVEC™-TOPO TA Cloning Kit enclosed in an OptiCHO™ Antibody Express Kit (Cat no. 12762-019, Invitrogen) and a vector from the pcDNA™3.3-TOPO TA Cloning Kit (Cat no. 8300-01), respectively, so as to construct recombinant vectors for expressing affinity-matured antibodies.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5\times10^5$ cells/mL, and after 24 hours, when the cell number reached to $1\times10^6$ cells/mL, the transient expression was performed. A transfection was performed by a liposomal reagent method using Freestyle™ MAX reagent (Invitrogen), wherein in a 15 mL tube, the DNA was provided in the mixture ratio of 1:1 (heavy chain DNA:light chain DNA) and mixed with 2 mL of OptiPro™ SFM (Invitrogen) (A). In another 15 mL tube, 100 μL of Freestyle™ MAX reagent and 2 mL of OptiPro™ SFM were mixed (B). This was followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime fast protein liquid chromatography (GE Healthcare) to purify the antibody. In this regard, 100 mL of the supernatant was loaded at a flow rate of 5 mL/min to AKTA Prime fast protein liquid chromatography equipped with a Protein A column (GE Healthcare, 17-0405-03), followed by elution with an IgG elution buffer (Thermo Scientific, 21004). The buffer was exchanged with PBS to purify four affinity-matured antibodies (hereinafter referred to as "huAbF46-H4-A1 (L3-1 origin), huAbF46-H4-A2 (L3-2 origin), huAbF46-H4-A3 (L3-3 origin), and huAbF46-H4-A5 (L3-5 origin)," respectively).

1.8. Construction of Constant Region- and/or Hinge Region-Substituted huAbF46-H4-A1

Among the four antibodies selected in Reference Example 1.7, huAbF46-H4-A1 was found to be the highest in affinity for c-Met and the lowest in Akt phosphorylation and c-Met degradation degree. In the antibody, the hinge region, or the constant region and the hinge region, were substituted.

The antibody huAbF46-H4-A1 (U6-HC7) was composed of a heavy chain comprising (a) the heavy chain variable region of huAbF46-H4-A1, U6-HC7 hinge, and the constant region of human IgG1 constant region, and (b) a light chain comprising the light chain variable region of huAbF46-H4-A1 and human kappa constant region. The antibody huAbF46-H4-A1 (IgG2 hinge) was composed of (a) a heavy chain comprising a heavy chain variable region, a human IgG2 hinge region, and a human IgG1 constant region, and (b) a light chain comprising the light chain variable region of huAbF46-H4-A1 and a human kappa constant region. The antibody huAbF46-H4-A1 (IgG2 Fc) was composed of (a) the heavy chain variable region of huAbF46-H4-A1, a human IgG2 hinge region, and a human IgG2 constant region, and (b) a light chain comprising the light variable region of huAbF46-H4-A1 and a human kappa constant region. Hereupon, the histidine residue at position 36 on the human kappa constant region of the light chain was changed to tyrosine in all of the three antibodies to increase antibody production.

For use in constructing the three antibodies, a polynucleotide (SEQ ID NO: 63) encoding a polypeptide (SEQ ID NO: 62) composed of the heavy chain variable region of huAbF46-H4-A1, a U6-HC7 hinge region, and a human IgG1 constant region, a polynucleotide (SEQ ID NO: 65) encoding a polypeptide (SEQ ID NO: 64) composed of the heavy chain variable region of huAbF46-H4-A1, a human IgG2 hinge region, and a human IgG1 region, a polynucleotide (SEQ ID NO: 67) encoding a polypeptide (SEQ ID NO: 66) composed of the heavy chain variable region of huAbF46-H4-A1, a human IgG2 region, and a human IgG2 constant region, and a polynucleotide (SEQ ID NO: 69) encoding a polypeptide (SEQ ID NO: 68) composed of the light chain variable region of huAbF46-H4-A1, with a tyrosine residue instead of histidine at position 36, and a human kappa constant region were synthesized in BIONEER. Then, the DNA fragments having heavy chain nucleotide sequences were inserted into a vector from the pOptiVEC™-TOPO TA Cloning Kit enclosed in an OptiCHO™ Antibody Express Kit (Cat no. 12762-019, Invitrogen) while DNA fragments having light chain nucleotide sequences were inserted into a vector from the pcDNA™3.3-TOPO TA Cloning Kit (Cat no. 8300-01) so as to construct vectors for expressing the antibodies.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5\times10^5$ cells/mL, and after 24 hours, when the cell number reached to $1\times10^6$ cells/mL, the transient expression was performed. A transfection was performed by a liposomal reagent method using Freestyle™ MAX reagent (Invitrogen), wherein in a 15 mL tube, the DNA was provided in the mixture ratio of 1:1 (heavy chain DNA:light chain DNA) and mixed with 2 mL of OptiPro™ SFM (Iinvitrogen) (A). In another 15 mL tube, 100 μL of Freestyle™ MAX reagent and 2 mL of OptiPro™ SFM were mixed (B). This was followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime fast protein liquid chromatography (GE Healthcare) to purify the antibody. In this regard, 100 mL of the supernatant was loaded at a flow rate of 5 mL/min to AKTA Prime fast protein liquid chromatography equipped with a Protein A column (GE Healthcare, 17-0405-03), followed by elution with IgG elution buffer (Thermo Scientific, 21004). The buffer was exchanged with PBS to finally purify three antibodies (huAbF46-H4-A1 (U6-HC7), huAbF46-H4-A1 (IgG2 hinge), and huAbF46-H4-A1 (IgG2 Fc)). Among the three antibodies, huAbF46-H4-A1 (U6-HC7) and huAbF46-H4-A1 (IgG2 Fc) were selected for the following examples, and respectively referred as anti-c-Met antibody L3-1Y U6-HC7 for huAbF46-H4-A1 (U6-HC7) and anti-c-Met antibody L3-1Y IgG2 for huAbF46-H4-A1 (IgG2 Fc).

Reference Example 2: Preparation of Anti-Her2 scFv

The sequence of a scFv antibody binding to Her2 was prepared on the basis of the sequence of Trastuzumab (HERCEPTIN) by inserting a peptide linker $(G_4S)_3$ (SEQ ID NO: 116) between the heavy chain variable region and the light chain variable region. Specifically, a $(GGGGS)_3$ (SEQ ID NO: 116) linker coding DNA sequence was added to the heavy chain variable region (SEQ ID NO: 109) coding DNA sequence (SEQ ID NO: 110) and the light chain variable region (SEQ ID NO: 111) coding DNA sequence (SEQ ID NO: 112) of the anti-Her2 antibody (HERCEPTIN) using an automatic gene synthesis (BIONEER Inc.) to synthesize a scFv coding DNA of the anti-Her2 antibody.

The thus obtained scFv of the anti-Her2 antibody (anti-Her2 scFv) was used to manufacture the following bispecific antibody.

<Amino acid sequence of anti-Her2
antibody heavy chain variable region>
(SEQ ID NO: 109)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSS

<Coding DNA sequence of anti-Her2
antibody heavy chain variable region>
(SEQ ID NO: 110)
gaagttcagctggtggagtctggcggtggcctggtgcagccagggggctc actccgtttgtcctgtgcagcttctggcttcaacattaaagacacctata tacactgggtgcgtcaggcccggtaagggcctggaatgggttgcaagg atttatcctacgaatggttatactagatatgccgatagcgtcaagggccg tttcactataagcgcagacacatccaaaaacacagcctacctgcagatga acagcctgcgtgctgaggacactgccgtctattattgttctagatgggga ggggacggcttctatgctatggactactggggtcaaggaaccctggtcac cgtctcctcg <Amino acid sequence of anti-Her2
antibody light chain variable region>
(SEQ ID NO: 111)
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIKR

<Coding DNA sequence of anti-Her2
antibody light chain variable region>
(SEQ ID NO: 112)
gatatccagatgacccagtccccgagctccctgtccgcctctgtgggcga tagggtcaccatcacctgccgtgccagtcaggatgtgaatactgctgtag cctggtatcaacagaaaccaggaaaagctccgaaactactgatttactcg gcatccttcctctactctggagtcccttctcgcttctctggttccagatc tgggacggatttcactctgaccatcagcagtctgcagccggaagacttcg caacttattactgtcagcaacattatactactcctcccacgttcggacag ggtaccaaggtggagatcaaacga Example 1: Preparation of Bispecific Anti-c-Met/Anti-Her2 Antibody The anti-Her2 scFv prepared in the Reference Example 2 was fused at the C-terminus of Fc of the anti cMet antibody L3-1Y-IgG2 (uAbF46-H4-A1(IgG2 Fc)) prepared in the Reference Example 1. The fusion procedures are as follows.

A DNA segment having a base sequence (SEQ ID NO: 66) corresponding to the heavy chain of the anti cMet antibody L3-1Y-IgG2 prepared in Reference Example 1 was inserted into a vector from the pcDNA™3.3-TOPO TA Cloning Kit (Cat no. 8300-01) which is included in OptiCHO™ Antibody Express Kit (Cat no. 12762-019) by Invitrogen Inc., and a DNA segment having a base sequence (SEQ ID NO: 68) corresponding to the light chain of the anti cMet antibody L3-1Y-IgG2 was inserted into a vector from the pOptiVEC™-TOPO TA Cloning Kit. Thereafter, the anti-Her2 scFv coding DNA prepared in Reference Example 2 was fused at the C-terminus of Fc of L3-1Y-IgG2 inserted into pcDNA™3.3 expression vector, using the coding DNA sequence of a peptide linker consisting of $(GGGGS)_2$ (SEQ ID NO: 113), to construct a vector for the expression of a bispecific antibody.

The constructed vectors were each amplified using Qiagen Maxiprep kit (Cat no. 12662 and their temporary expression proceeded using Freestyle™ MAX 293 Expression System (Invitrogen). 293 F cells, which were cultured in a suspension culture manner using FreeStyle™ 293 Expression Medium as a medium, were used. One day before the temporary expression, the cells were prepared at a concentration of $5 \times 10^5$ cells/mL and after 24 hours, their temporary expression started when the number of the cells reached $1 \times 10^6$ cells/mL. Transfection was performed by a liposomal reagent method using Freestyle™ MAX reagent (Invitrogen). DNA was prepared in a 15 mL tube in a ratio of heavy chain DNA:light chain DNA=3:2 and mixed with 2 mL of OptiPro™ SFM (Invitrogen) (A). 100 μL of Freestyle™ MAX reagent and 2 mL of OptiPro™ SFM were mixed in another 15 mL tube (B). After (A) and (B) were mixed and incubated for 15 min., the mixture solution was then slowly mixed into the cells which were prepared one day before. After the transfection was complete, the cells were cultured in a 37° C., 80% humidity, 8% $CO_2$, 130 rpm incubator for 5 days.

The cultured cells were centrifuged to obtain each 100 mL of supernatants, which were then purified using AKTA Prime fast protein liquid chromatography (GE Healthcare). The culture was added at a flow rate of 5 mL/min. to the AKTA Prime fast protein liquid chromatography installed with Protein A column (GE Healthcare, 17-0405-03) to perform elution using an IgG elution buffer (Thermo Scientific, 21004). The buffer was replaced by a PBS buffer to finally obtain a purified bispecific anti cMet/anti-Her2 antibody.

The thus prepared bispecific anti-c-Met/anti-Her2 antibody in which the anti-Her2 scFv is fused at the C-terminus of the anti-c-Met antibody L3-1Y-IgG2 was named MH2-01.

Example 2: Dual Binding of Bispecific Anti-c-Met/Anti-Her2 Antibody

Whether the anti-c-Met/anti-Her2 bispecific antibody prepared in the Example 1 is an antibody against two types of antigens (cMet/Her2) was determined using Biacore T100 (GE). An anti-6×His antibody (#MAB050, R&D Systems) was immobilized onto a CM5 chip (#BR-1005-30, GE) using an amine coupling kit (#BR-1000-50, GE) according to the manufacturer's instructions. After the immobilization, c-Met-Fc (#358-MT/CF, R&D Systems) was injected thereto at a concentration of 15 μg/mL for 1 min. and then, the bispecific antibody MH2-01 prepared in Example 1 was injected at a concentration of 20 nM for 1 min. Thereafter, Her2-Fc (1129-ER, R&D Systems) was injected at 100 nM for 1 min.

Figure 2:
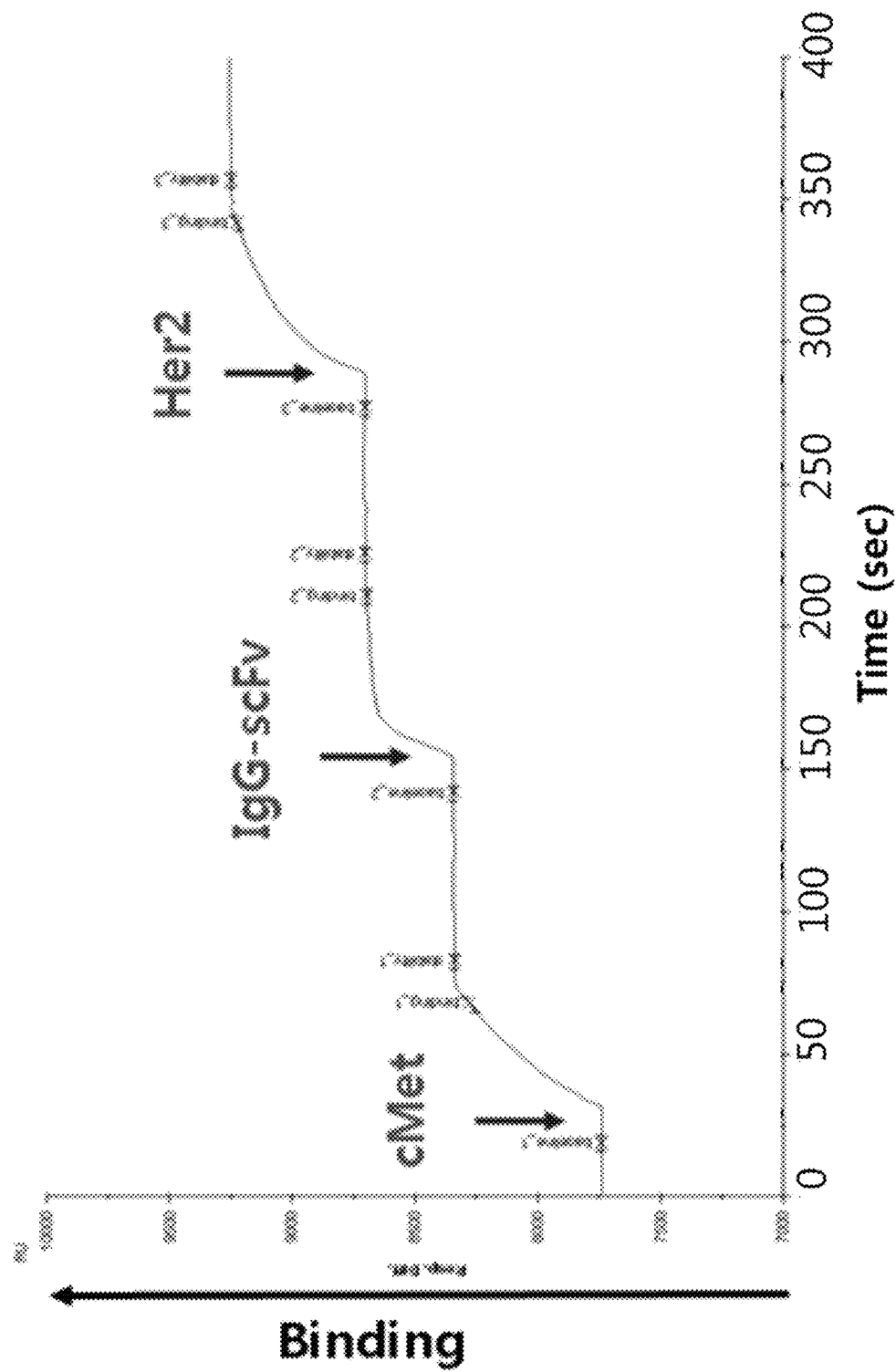
FIG. 2 is a graph showing dual binding of an anti-c-Met/anti-Her2 bispecific antibody according to one example. Binding response differential (Ru) is indicated on the y-axis, and time (seconds) is indicated on the x-axis.

The obtained results are shown in FIG. 2. The bispecific antibody MH2-01 prepared in the Example 1 bound to both c-Met and Her2 (see FIG. 2).

In addition, the affinities of the prepared bispecific anti-c-Met/anti-Her2 antibody toward two types of antigens (cMet/Her2) were each identified using BIACORE T100 (GE). A human Fab binder (GE Healthcare) was immobilized at the surface of a CM5 chip (#BR-1005-30, GE) according to the manufacturer's specifications. About 90 to 120 Ru of MH2-01 was captured, and c-Met-Fc (#358-MT/CF, R&D Systems) or Her2-Fc (1129-ER, R&D Systems) were injected at various concentrations into the captured antibody. 10 mM Glycine-HCl (pH 1.5) solution was injected thereto to regenerate the surface. In order to measure affinity, the data obtained from this experiment was fitted using BIAevaluation software (GE Healthcare, BIACORE T100 evaluation software).

The obtained results are shown in FIG. 2 and Table 3.

TABLE 3

| Antibody | Antigen | $K_D$ (nM) | $k_a$ (1/Ms) | $k_d$ (1/s) |
| --- | --- | --- | --- | --- |
| MH2-01 | cMet | 0.14 | $6.6 \times 10^5$ | $9.3 \times 10^{-5}$ |
| | Her2 | <0.01 | $1.2 \times 10^5$ | $<1.1 \times 10^{-5}$ |

As seen in FIG. 2 and Table 3, the bispecific antibody MH2-01 prepared in the Example 1 bound to both c-Met and Her2.

Reference Example 3: Preparation of Cell Lines

Cell lines to be used in the following examples to test the efficiency of the anti-c-Met/anti-Her2 bispecific antibody prepared in the Example 1 are EBC1, a lung cancer cell line, and MKN45, a stomach cancer cell line, which were purchased from ATCC.

Example 3: Suppression of Cancer Cell Proliferation by Anti-c-Met/Anti-Her2 Bispecific Antibody Suppression effects on the proliferation of cancer cells of the anti-c-Met/anti-Her2 bispecific antibody prepared in the Example 1 were identified in the MKN45 stomach cancer cell line and EBC1 cells.

All the cell lines were cultured in a RPMI1640 medium (#11875-093, Gibco) to which 10% (v/v) FBS and 1% (v/v) Penicillin-Streptomycin were added, in 5% $CO_2$ and 37° C. conditions. For a cell proliferation assay, each cell line was subcultured at a concentration of $1 \times 10^4$ cells/well in a 96-well plate, which was treated with the anti-c-Met/anti-Her2 bispecific antibody MH2-01 prepared in Example 1 in an amount of 5 μg/mL and cultured for 72 hours. A medium with no antibody added was used as a negative control, and commercially available Her2 inhibitor Herceptin (Roche) treatment group (marked as H), L3-1Y-IgG2 antibody 5 μg/mL treatment group prepared in Reference Example 1 (marked as L or L3-1Y), and co-treatment group (L+H) of L3-1Y-IgG2 antibody 5 μg/mL prepared in Reference Example 1 and Herceptin 5 μg/mL were each used as positive controls.

After cultivation, cell proliferation degrees were analyzed using Cell Counting Kit-8 assay (Dojindo Molecular Technologies, Gaithersburg, Md.) according to the manufacturer's instructions. In brief, after the cultivation for 72 hours, 10 μl of CCK8 solution was added to each well and after the additional cultivation for 2.5 hours, absorption degrees were read at 450 nm using a microplate reader.

Figure 3:
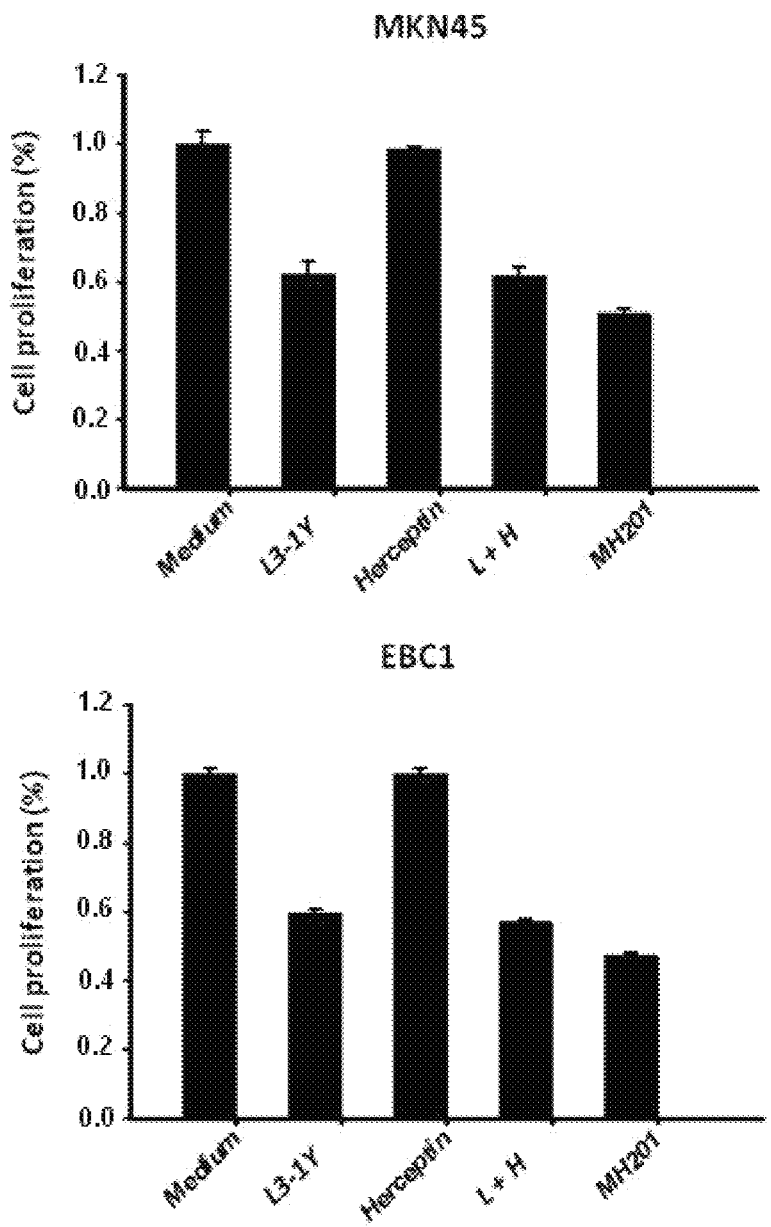
FIG. 3 contains graphs showing proliferation levels of cancer cells (MKN45 stomach cancer cell line (upper) and EBC-1 lung cancer cell line (lower)) when treated with an anti-c-Met/anti-Her2 bispecific antibody according to one example as relative values against the control group (Medium; antibody non-treatment group).

The obtained results are shown in FIG. 3. As seen in FIG. 3, the anti-c-Met/anti-Her2 bispecific antibody MH2-01 showed remarkable increases in cell proliferation inhibitory effects in both cell lines, compared to the cases treated individually with the anti-c-Met antibody L3-1Y-IgG2 (L3-1Y) and the anti-Her2 antibody Herceptin. In particular, in the EBC-1 cells, the bispecific antibody MH2-01 showed excellent cell proliferation inhibitory effects, even compared to the co-treatment case of the anti-c-Met antibody L3-1Y-IgG2 (L+H).

Example 4: Her2 Activation Inhibitory Test of Anti-c-Met/Anti-Her2 Bispecific Antibody The MKN45 cell line and EBC-1 cells were each treated with 5 μg/mL of Herceptin, 5 μg/mL of L3-1Y-IgG2 antibody (Reference Example 1), 5 μg/mL of MH2-01 (Example 1), and 5 μg/mL of L3-1Y-IgG2 and 5 μg/mL of Herceptin (co-treatment group), respectively for 24 hours.

Thereafter, the cells were lysed with COMPLETE Lysis-M lysis buffer (#04719956001, Roche) to collect cell lysates, which were then subject to SDS-PAGE electrophoresis.

After the electrophoresis, the proteins from the gels were transferred onto nitrocellulose membrane (#LC2006, Invitrogen), which was then blocked with a skim milk (5% in TBST (a mixture of Tris-Buffered Saline and TWEEN 20 (polysorbate 20))) at a room temperature for one hour. After blocking, for the first antibody reaction, the membrane was treated with a 1:2000 dilution of phospho c-Met antibody, anti phospho Her2 antibody, anti-Her2 antibody (all available from Cell Signaling Technology), and anti-c-Met antibody (Abcam) at a room temperature for two hours. After the first antibody reaction, the membrane was washed three times with PBS for 5 min. and then, it was treated with a 1:5000 dilution of the secondary antibody (Cell Signaling Technology) with horseradish peroxidase attached thereto against each first antibody at a room temperature for one hour. After the secondary antibody reaction, the membrane was washed three times with PBS for 5 min. and then sensitized with Enhanced chemiluminescence substrate (Thermo Scientific) to identify the degree of antigen-antibody reaction through IMAGEQUANT LAS system (GE Healthcare).

Figure 4:
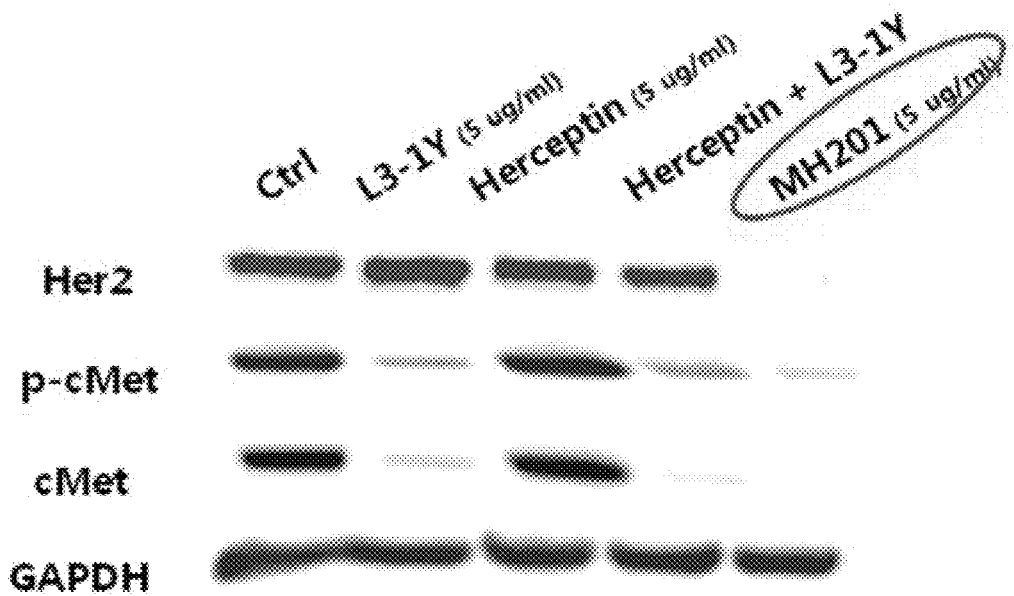
FIG. 4 contains western blotting results showing Her2 activation inhibitory degrees of an anti-c-Met/anti-Her2 bispecific antibody according to one example in a MKN45 stomach cancer cell line (upper) and EBC-1 lung cancer cell line (lower).
Figure 4:
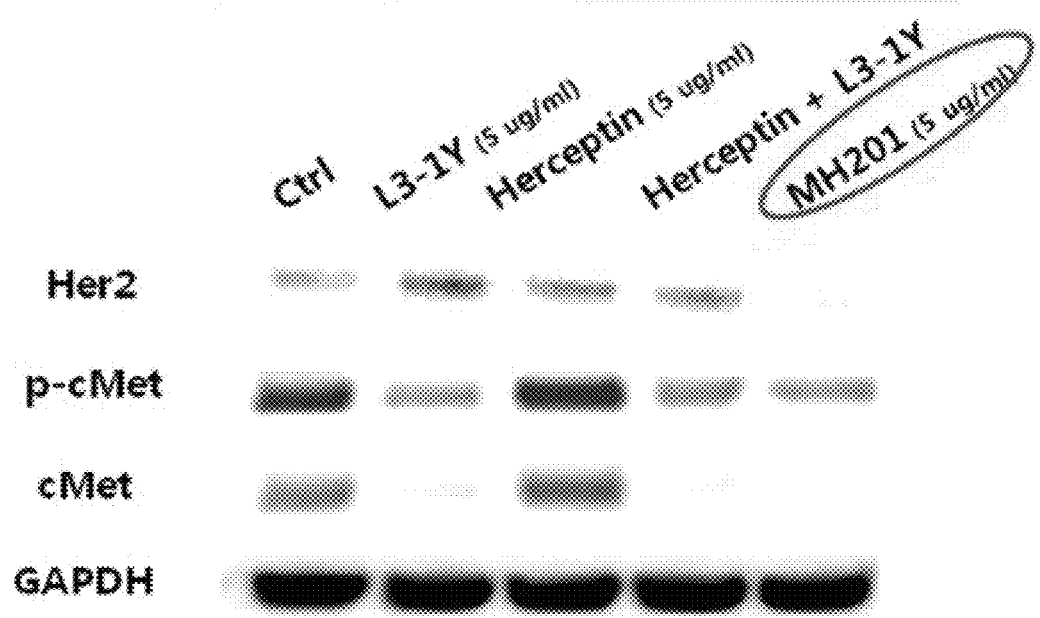

The obtained results are shown in FIG. 4. As seen in FIG. 4, when treated with the anti-c-Met/anti-Her2 bispecific antibody MH2-01, cMet was degraded and the activation of cMet was suppressed. Particularly, the degradation degree of Her2 was more excellent than the individual treatment of the anti-c-Met antibody L3-1Y-IgG2 or the anti-Her2 antibody Herceptin. This is to show that the anti-c-Met antibody and the anti-Her2 antibody have synergistic effects by forming a bispecific antibody together, compared to the sole Her2 inhibitor.

Example 5: Co-Localization of cMet and Her2 by Anti-c-Met/Anti-Her2 Bispecific Antibody The MKN45 cell line and the EBC1 cell line were prepared in amounts of $4\times10^4$ cells/well, respectively and an OE-33 cell line was prepared in an amount of $2\times10^4$ cells/well, to which L3-1Y-IgG2 prepared in Reference Example 1 and Herceptin, and the anti-c-Met/anti-Her2 bispecific antibody MH2-01 prepared in Example 1 were each added individually or in combination to become the concentration of 1 µg/mL per well (in case of combination treatment, to become 1 µg/mL each) and treated at 37° C. for 4 hours. The cells were treated with 4% (v/v) formaldehyde for 15 min. to immobilize them on a plate, and washed three times with PBS. Thereafter, the cells were treated with a blocking buffer (0.5% triton x-100 and 5% donkey serum) at a room temperature for one hour and then treated with a 1:100 dilution of the first antibodies (cMet first antibody; #37-0100, Invitrogen, Her2 first antibody; #2165, Cell Signaling) against c-Met and Her2, respectively in amounts of 100 µL at 4° C. for 15 hours. After the cells were washed three time with PBS, they were treated with a 1:1000 dilution of the secondary antibodies (cMet secondary antibody; #A11001, Life Technology, Her2 secondary antibody; #A21244, Life Technology) against c-Met and Her2, respectively in amounts of 100 µL at a room temperature for 1 hour and washed three times with PBS to prepare a plate as a mounting medium (#H-1200, Vector). The prepared cells were observed with a confocal microscope (Zeiss, LSM710).

Figure 5:
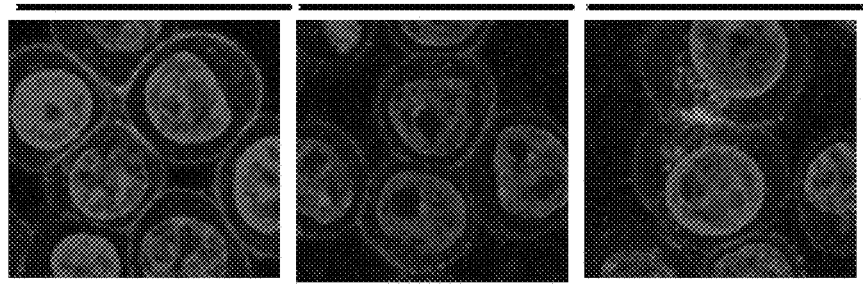
FIG. 5 contains confocal microscope photographs showing the co-localization of cMet and Her2 in a MKN45 stomach cancer cell line by an anti-c-Met/anti-Her2 bispecific antibody according to one example.
Figure 5:
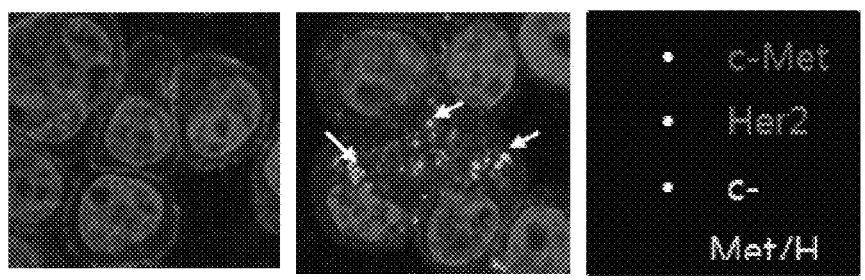
Figure 6:
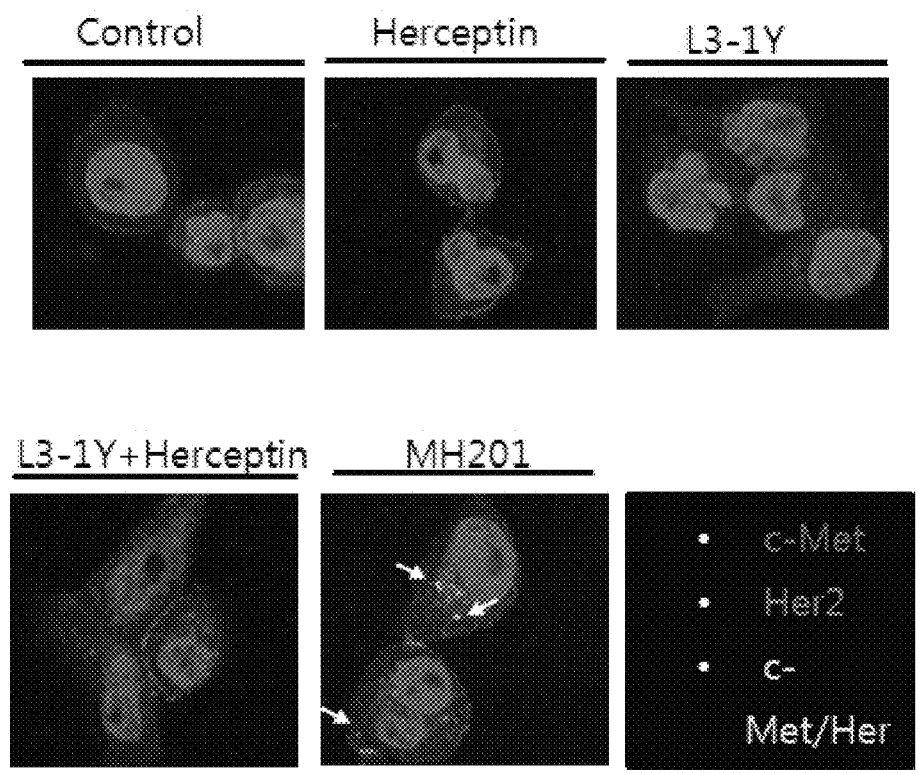
FIG. 6 contains confocal microscope photographs showing the co-localization of cMet and Her2 in an EBC-1 lung cancer cell line by an anti-c-Met/anti-Her2 bispecific antibody according to one example.
Figure 7:
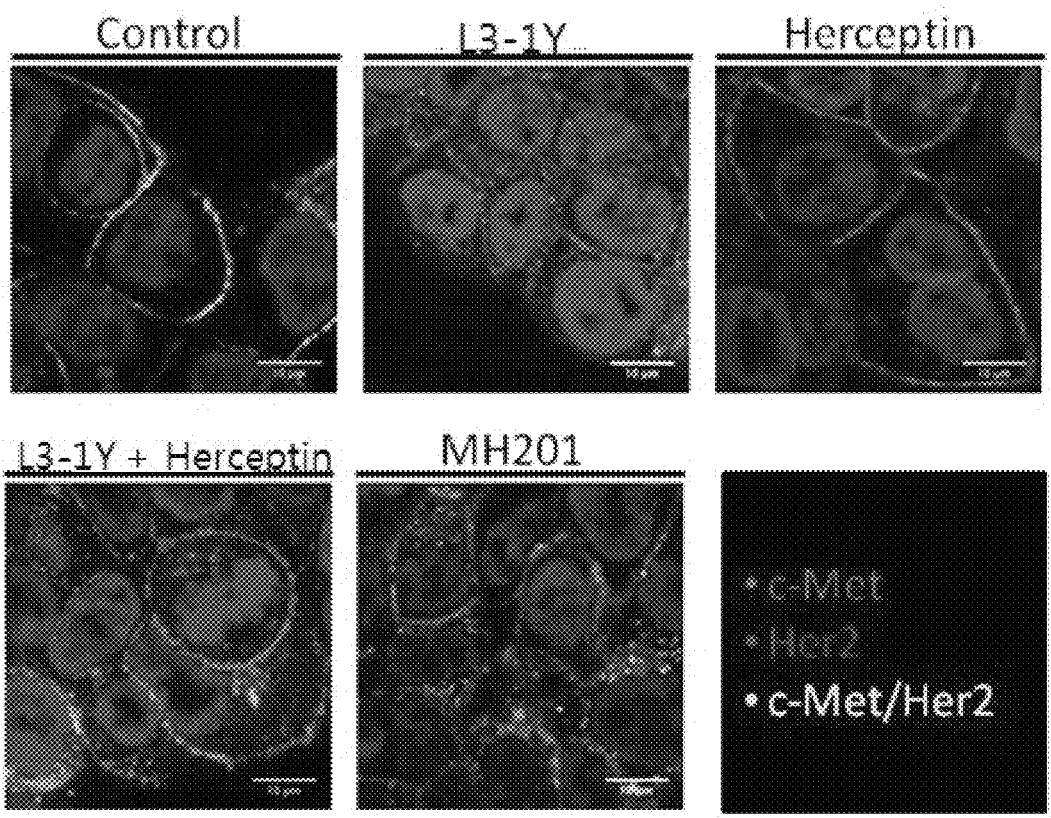
FIG. 7 contains confocal microscope photographs showing the co-localization of cMet and Her2 in an OE-33 esophagus cancer cell line by an anti-c-Met/anti-Her2 bispecific antibody according to one example.

The obtained results are shown in FIG. 5 (MKN45 stomach cancer cell line), FIG. 6 (EBC-1 lung cancer cell line), and FIG. 7 (OE-33 esophagus cancer cell line). As seen in FIG. 5, FIG. 6, and FIG. 7, in the case of the sole treatment of Herceptin, Her2 was still located at cell membranes; even in the case of the co-treatment of L3-1Y and Herceptin, only c-Met migrated inside the cells and most of Her2 was located at the cell membranes; however, in the case of the treatment of the anti-c-Met/anti-Her2 bispecific antibody MH2-01, both c-Met and Her2 migrated inside the cells. This result demonstrates that the double antibody MI-12-01 against c-Met/Her2 can increase anticancer effects by the internalization of cMet and Her2 into the cells at the same time.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An anti-c-Met/anti-Her2 bispecific antibody comprising (a) an anti-c-Met antibody in an IgG form comprising six complementarity determining regions (CDRs), linked to (b) an antigen-binding fragment of an anti-Her2 antibody comprising six complementarity determining regions,
   wherein the anti-c-Met antibody comprises:
   (i) a heavy chain variable region comprising a CDR-H1 comprising the amino acid sequence of SEQ ID NO: 1; a CDR-H2 comprising the amino acid sequence of SEQ ID NO: 2 and a CDR-H3 comprising the amino acid sequence of SEQ ID NO: 3; and
   (ii) a light chain variable region comprising a CDR-L1 comprising the amino acid sequence of SEQ ID NO: 10; a CDR-L2 comprising the amino acid sequence of SEQ ID NO: 11; and a CDR-L3 comprising the amino acid sequence of SEQ ID NO: 13, SEQ ID NO: 14, SEQ ID NO: 15, or SEQ ID NO: 16.

2. The anti-c-Met/anti-Her2 bispecific antibody according to claim 1, wherein the antigen-binding fragment is an scFv, (scFv)2, Fab, Fab' or F(ab')2.

3. The anti-c-Met/anti-Her2 bispecific antibody according to claim 1, wherein the anti-c-Met antibody comprises:
   (i) a heavy chain variable region comprising the amino acid sequence of SEQ ID NO: 17, and
   (ii) a light chain variable region comprising the amino acid sequence of SEQ ID NO: 114, SEQ ID NO: 18, SEQ ID NO: 19, SEQ ID NO: 20, or SEQ ID NO: 21.

4. The anti-c-Met/anti-Her2 bispecific antibody according to claim 1, wherein the anti-c-Met antibody comprises:
   (i) a heavy chain comprising the amino acid sequence of SEQ ID NO: 62, the amino acid sequence from positions 18 to 462 of SEQ ID NO: 62, the amino acid sequence of SEQ ID NO: 64, the amino acid sequence from positions 18 to 461 of SEQ ID NO: 64, the amino acid sequence of SEQ ID NO: 66, or the amino acid sequence from positions 18 to 460 of SEQ ID NO: 66; and
   (ii) a light chain comprising the amino acid sequence of SEQ ID NO: 68, the amino acid sequence from positions 21 to 240 of SEQ ID NO: 68, the amino acid sequence of SEQ ID NO: 70, the amino acid sequence from positions 21 to 240 of SEQ ID NO: 70.

5. The anti-c-Met/anti-Her2 bispecific antibody according to claim 1, wherein the anti-c-Met antibody comprises a heavy chain comprising the amino acid sequence of SEQ ID NO: 66 or the amino acid sequence from positions 18 to 460 of SEQ ID NO: 66, and a light chain comprising the amino acid sequence of SEQ ID NO: 68 or the amino acid sequence from positions 21 to 240 of SEQ ID NO: 68.

6. The anti-c-Met/anti-Her2 bispecific antibody according to claim 1, wherein the anti-Her2 antigen binding fragment is an antigen binding fragment from Trastuzumab or Pertuzumab.

7. The anti-c-Met/anti-Her2 bispecific antibody according to claim 1, wherein the antigen-binding fragment of the anti-Her2 antibody is covalently linked to the C-terminus of the anti-c-Met antibody.

8. The anti-c-Met/anti-Her2 bispecific antibody according to claim 7, wherein the antigen-binding fragment of the anti-Her2 antibody comprises a heavy chain variable region comprising the sequence of SEQ ID NO: 109 and a light chain variable region comprising the sequence of SEQ ID NO: 111.

9. A pharmaceutical composition comprising the anti-c-Met/anti-Her2 bispecific antibody according to claim 1 and a pharmaceutically acceptable carrier.

10. A method of treatment of a cancer, comprising administering the anti-c-Met/anti-Her2 bispecific antibody of claim 1 to a patient in need thereof.

* * * * *

SEQUENCE LISTING

<160> NUMBER OF SEQ ID NOS: 117

<210> SEQ ID NO 1
<211> LENGTH: 5
<212> TYPE: PRT

```
<213> ORGANISM: Artificial Sequence
<220> FEATURE:
<223> OTHER INFORMATION: Synthetic (heavy chain CDR1 of AbF46)

<400> SEQUENCE: 1

Asp Tyr Tyr Met Ser
1               5

<210> SEQ ID NO 2
<211> LENGTH: 19
<212> TYPE: PRT
<213> ORGANISM: Artificial Sequence
<220> FEATURE:
<223> OTHER INFORMATION: Synthetic (heavy chain CDR2 of AbF46)

<400> SEQUENCE: 2

Phe Ile Arg Asn Lys Ala Asn Gly Tyr Thr Thr Glu Tyr Ser Ala Ser
1               5                   10                  15

Val Lys Gly

<210> SEQ ID NO 3
<211> LENGTH: 6
<212> TYPE: PRT
<213> ORGANISM: Artificial Sequence
<220> FEATURE:
<223> OTHER INFORMATION: Synthetic (heavy chain CDR3 of AbF46)

<400> SEQUENCE: 3

Asp Asn Trp Phe Ala Tyr
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic (heavy chain CDR1 of c-Met antibody)
<220> FEATURE:
<221> NAME/KEY: MOD_RES
<222> LOCATION: (1)..(1)
<223> OTHER INFORMATION: Xaa is Pro or Ser or absent
<220> FEATURE:
<221> NAME/KEY: MOD_RES
<222> LOCATION: (2)..(2)
<223> OTHER INFORMATION: Xaa is Glu or Asp

<400> SEQUENCE: 4

Xaa Xaa Tyr Tyr Met Ser
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic (heavy chain CDR2 of c-Met antibody)
<220> FEATURE:
<221> NAME/KEY: MOD_RES
<222> LOCATION: (3)..(3)
<223> OTHER INFORMATION: Xaa is Asn or Lys
<220> FEATURE:
<221> NAME/KEY: MOD_RES
<222> LOCATION: (4)..(4)
<223> OTHER INFORMATION: Xaa is Ala or Val
<220> FEATURE:
<221> NAME/KEY: MOD_RES
<222> LOCATION: (7)..(7)
<223> OTHER INFORMATION: Xaa is Asn or Thr

<400> SEQUENCE: 5
```

```
Arg Asn Xaa Xaa Asn Gly Xaa Thr
1               5
```

<210> SEQ ID NO 6
<211> LENGTH: 6
<212> TYPE: PRT
<213> ORGANISM: Artificial Sequence
<220> FEATURE:
<223> OTHER INFORMATION: Synthetic (heavy chain CDR3 of c-Met antibody)
<220> FEATURE:
<221> NAME/KEY: MOD_RES
<222> LOCATION: (5)..(5)
<223> OTHER INFORMATION: Xaa is Ser or Thr

<400> SEQUENCE: 6

```
Asp Asn Trp Leu Xaa Tyr
1               5
```

<210> SEQ ID NO 7
<211> LENGTH: 17
<212> TYPE: PRT
<213> ORGANISM: Artificial Sequence
<220> FEATURE:
<223> OTHER INFORMATION: Synthetic (light chain CDR1 of c-Met antibody)
<220> FEATURE:
<221> NAME/KEY: MOD_RES
<222> LOCATION: (4)..(4)
<223> OTHER INFORMATION: Xaa is His, Arg, Gln or Lys
<220> FEATURE:
<221> NAME/KEY: MOD_RES
<222> LOCATION: (9)..(9)
<223> OTHER INFORMATION: Xaa is Ser or Trp
<220> FEATURE:
<221> NAME/KEY: MOD_RES
<222> LOCATION: (12)..(12)
<223> OTHER INFORMATION: Xaa is His or Gln
<220> FEATURE:
<221> NAME/KEY: MOD_RES
<222> LOCATION: (13)..(13)
<223> OTHER INFORMATION: Xaa is Lys or Asn

<400> SEQUENCE: 7

```
Lys Ser Ser Xaa Ser Leu Leu Ala Xaa Gly Asn Xaa Xaa Asn Tyr Leu
1               5                   10                  15

Ala
```

<210> SEQ ID NO 8
<211> LENGTH: 7
<212> TYPE: PRT
<213> ORGANISM: Artificial Sequence
<220> FEATURE:
<223> OTHER INFORMATION: Synthetic (light chain CDR2 of c-Met antibody)
<220> FEATURE:
<221> NAME/KEY: MOD_RES
<222> LOCATION: (2)..(2)
<223> OTHER INFORMATION: Xaa is Ala or Gly
<220> FEATURE:
<221> NAME/KEY: MOD_RES
<222> LOCATION: (4)..(4)
<223> OTHER INFORMATION: X is Thr or Lys
<220> FEATURE:
<221> NAME/KEY: MOD_RES
<222> LOCATION: (7)..(7)
<223> OTHER INFORMATION: Xaa is Ser or Pro

<400> SEQUENCE: 8

```
Trp Xaa Ser Xaa Arg Val Xaa
1               5
```

<210> SEQ ID NO 9

```
<211> LENGTH: 9
<212> TYPE: PRT
<213> ORGANISM: Artificial Sequence
<220> FEATURE:
<223> OTHER INFORMATION: Synthetic (light chain CDR3 of c-Met antibody)
<220> FEATURE:
<221> NAME/KEY: MOD_RES
<222> LOCATION: (1)..(1)
<223> OTHER INFORMATION: Xaa is Gly, Ala or Gln
<220> FEATURE:
<221> NAME/KEY: MOD_RES
<222> LOCATION: (6)..(6)
<223> OTHER INFORMATION: Xaa is Arg, His, Ser, Ala, Gly or Lys
<220> FEATURE:
<221> NAME/KEY: MOD_RES
<222> LOCATION: (8)..(8)
<223> OTHER INFORMATION: Xaa is Leu, Tyr, Phe or Met

<400> SEQUENCE: 9

Xaa Gln Ser Tyr Ser Xaa Pro Xaa Thr
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic (light chain CDR1 of AbF46)

<400> SEQUENCE: 10

Lys Ser Ser Gln Ser Leu Leu Ala Ser Gly Asn Gln Asn Asn Tyr Leu
1               5                   10                  15

Ala

<210> SEQ ID NO 11
<211> LENGTH: 7
<212> TYPE: PRT
<213> ORGANISM: Artificial Sequence
<220> FEATURE:
<223> OTHER INFORMATION: Synthetic (light chain CDR2 of AbF46)

<400> SEQUENCE: 11

Trp Ala Ser Thr Arg Val Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic (light chain CDR3 of AbF46)

<400> SEQUENCE: 12

Gln Gln Ser Tyr Ser Ala Pro Leu Thr
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic (CDR-L3 derived from L3-1 clone)

<400> SEQUENCE: 13

Gln Gln Ser Tyr Ser Arg Pro Tyr Thr
1               5

<210> SEQ ID NO 14
```

```
<211> LENGTH: 9
<212> TYPE: PRT
<213> ORGANISM: Artificial Sequence
<220> FEATURE:
<223> OTHER INFORMATION: Synthetic (CDR-L3 derived from L3-2 clone)

<400> SEQUENCE: 14

Gly Gln Ser Tyr Ser Arg Pro Leu Thr
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic (CDR-L3 derived from L3-3 clone)

<400> SEQUENCE: 15

Ala Gln Ser Tyr Ser His Pro Phe Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic (CDR-L3 derived from L3-5 clone)

<400> SEQUENCE: 16

Gln Gln Ser Tyr Ser Arg Pro Phe Thr
1               5

<210> SEQ ID NO 17
<211> LENGTH: 117
<212> TYPE: PRT
<213> ORGANISM: Artificial Sequence
<220> FEATURE:
<223> OTHER INFORMATION: Synthetic (heavy chain variable region of anti
      c-Met humanized antibody(huAbF46-H4))

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 18
<211> LENGTH: 114
<212> TYPE: PRT
<213> ORGANISM: Artificial Sequence
<220> FEATURE:
<223> OTHER INFORMATION: Synthetic (light chain variable region of anti
``` c-Met humanized antibody(huAbF46-H4))

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg

<210> SEQ ID NO 19
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gly Gln
                85                  90                  95

Ser Tyr Ser Arg Pro Leu Thr Phe Gly Gln Gly Thr Lys Val Glu Ile
            100                 105                 110

Lys Arg

<210> SEQ ID NO 20
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys 35                  40                  45
Ala Pro Lys Met Leu Ile Ile Trp Ala Ser Thr Arg Val Ser Gly Val
         50                  55                  60
Pro Ser Arg Phe Ser Gly Ser Gly Ser Gly Thr Asp Phe Thr Leu Thr
65                  70                  75                  80
Ile Ser Ser Leu Gln Pro Glu Asp Phe Ala Thr Tyr Tyr Cys Ala Gln
                 85                  90                  95
Ser Tyr Ser His Pro Phe Ser Phe Gly Gln Gly Thr Lys Val Glu Ile
                100                 105                 110
Lys Arg

<210> SEQ ID NO 21
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

<400> SEQUENCE: 21

Asp Ile Gln Met Thr Gln Ser Pro Ser Ser Leu Ser Ala Ser Val Gly
1               5                  10                  15
Asp Arg Val Thr Ile Thr Cys Lys Ser Ser Gln Ser Leu Leu Ala Ser
                20                  25                  30
Gly Asn Gln Asn Asn Tyr Leu Ala Trp His Gln Gln Lys Pro Gly Lys
            35                  40                  45
Ala Pro Lys Met Leu Ile Ile Trp Ala Ser Thr Arg Val Ser Gly Val
         50                  55                  60
Pro Ser Arg Phe Ser Gly Ser Gly Ser Gly Thr Asp Phe Thr Leu Thr
65                  70                  75                  80
Ile Ser Ser Leu Gln Pro Glu Asp Phe Ala Thr Tyr Tyr Cys Gln Gln
                 85                  90                  95
Ser Tyr Ser Arg Pro Phe Thr Phe Gly Gln Gly Thr Lys Val Glu Ile
                100                 105                 110
Lys Arg

<210> SEQ ID NO 22
<211> LENGTH: 6
<212> TYPE: PRT
<213> ORGANISM: Artificial Sequence
<220> FEATURE:
<223> OTHER INFORMATION: Synthetic (CDR-H1 derived from H11-4 clone)

<400> SEQUENCE: 22

Pro Glu Tyr Tyr Met Ser
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic (CDR-H1 derived from YC151 clone)

<400> SEQUENCE: 23

Pro Asp Tyr Tyr Met Ser
1               5

<210> SEQ ID NO 24
<211> LENGTH: 6

```
<212> TYPE: PRT
<213> ORGANISM: Artificial Sequence
<220> FEATURE:
<223> OTHER INFORMATION: Synthetic (CDR-H1 derived from YC193 clone)

<400> SEQUENCE: 24

Ser Asp Tyr Tyr Met Ser
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic (CDR-H2 derived from YC244 clone)

<400> SEQUENCE: 25

Arg Asn Asn Ala Asn Gly Asn Thr
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic (CDR-H2 derived from YC321 clone)

<400> SEQUENCE: 26

Arg Asn Lys Val Asn Gly Tyr Thr
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic (CDR-H3 derived from YC354 clone)

<400> SEQUENCE: 27

Asp Asn Trp Leu Ser Tyr
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic (CDR-H3 derived from YC374 clone)

<400> SEQUENCE: 28

Asp Asn Trp Leu Thr Tyr
1               5

<210> SEQ ID NO 29
<211> LENGTH: 17
<212> TYPE: PRT
<213> ORGANISM: Artificial Sequence
<220> FEATURE:
<223> OTHER INFORMATION: Synthetic (CDR-L1 derived from L1-1 clone)

<400> SEQUENCE: 29

Lys Ser Ser His Ser Leu Leu Ala Ser Gly Asn Gln Asn Asn Tyr Leu
1               5                   10                  15

Ala

<210> SEQ ID NO 30
```

<211> LENGTH: 17
<212> TYPE: PRT
<213> ORGANISM: Artificial Sequence
<220> FEATURE:
<223> OTHER INFORMATION: Synthetic (CDR-L1 derived from L1-3 clone)

<400> SEQUENCE: 30

Lys Ser Ser Arg Ser Leu Leu Ser Ser Gly Asn His Lys Asn Tyr Leu
1               5                   10                  15

Ala

<210> SEQ ID NO 31
<211> LENGTH: 17
<212> TYPE: PRT
<213> ORGANISM: Artificial Sequence
<220> FEATURE:
<223> OTHER INFORMATION: Synthetic (CDR-L1 derived from L1-4 clone)

<400> SEQUENCE: 31

Lys Ser Ser Lys Ser Leu Leu Ala Ser Gly Asn Gln Asn Asn Tyr Leu
1               5                   10                  15

Ala

<210> SEQ ID NO 32
<211> LENGTH: 17
<212> TYPE: PRT
<213> ORGANISM: Artificial Sequence
<220> FEATURE:
<223> OTHER INFORMATION: Synthetic (CDR-L1 derived from L1-12 clone)

<400> SEQUENCE: 32

Lys Ser Ser Arg Ser Leu Leu Ala Ser Gly Asn Gln Asn Asn Tyr Leu
1               5                   10                  15

Ala

<210> SEQ ID NO 33
<211> LENGTH: 17
<212> TYPE: PRT
<213> ORGANISM: Artificial Sequence
<220> FEATURE:
<223> OTHER INFORMATION: Synthetic (CDR-L1 derived from L1-22 clone)

<400> SEQUENCE: 33

Lys Ser Ser His Ser Leu Leu Ala Ser Gly Asn Gln Asn Asn Tyr Leu
1               5                   10                  15

Ala

<210> SEQ ID NO 34
<211> LENGTH: 7
<212> TYPE: PRT
<213> ORGANISM: Artificial Sequence
<220> FEATURE:
<223> OTHER INFORMATION: Synthetic (CDR-L2 derived from L2-9 clone)

<400> SEQUENCE: 34

Trp Ala Ser Lys Arg Val Ser
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic (CDR-L2 derived from L2-12 clone)

```
<400> SEQUENCE: 35

Trp Gly Ser Thr Arg Val Ser
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic (CDR-L2 derived from L2-16 clone)

<400> SEQUENCE: 36

Trp Gly Ser Thr Arg Val Pro
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic (CDR-L3 derived from L3-32 clone)

<400> SEQUENCE: 37

Gln Gln Ser Tyr Ser Lys Pro Phe Thr
1               5

<210> SEQ ID NO 38
<211> LENGTH: 1416
<212> TYPE: DNA
<213> ORGANISM: Artificial Sequence
<220> FEATURE:
<223> OTHER INFORMATION: Synthetic (nucleotide sequence of heavy chain
      of chAbF46)
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop sodon
<220> FEATURE:
<221> NAME/KEY: misc_feature
<222> LOCATION: (1411)..(1416)
<223> OTHER INFORMATION: XhoI restriction site

<400> SEQUENCE: 38
gaattcgccg ccaccatgga atggagctgg gttttctcg taacactttt aaatggtatc      60
cagtgtgagg tgaagctggt ggagtctgga ggaggcttgg tacagcctgg gggttctctg     120
agactctcct gtgcaacttc tgggttcacc ttcactgatt actacatgag ctgggtccgc     180
cagcctccag gaaaggcact tgagtggttg ggttttatta gaaacaaagc taatggttac     240
acaacagagt acagtgcatc tgtgaagggt cggttcacca tctccagaga taattcccaa     300
```

```
agcatcctct atcttcaaat ggacaccctg agagctgagg acagtgccac ttattactgt    360
gcaagagata actggtttgc ttactggggc caagggactc tggtcactgt ctctgcagct    420
agcaccaagg gcccatcggt cttccccctg gcacctcct ccaagagcac ctctgggggc     480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
tcttgtgaca aaactcacac atgcccaccg tgcccagcac ctgaactcct ggggggaccg    780
tcagtcttcc tcttccccc aaaacccaag gacaccctca tgatctcccg gacccctgag     840
gtcacatgcg tggtggtgga cgtgagccac gaagaccctg aggtcaagtt caactggtac    900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag    1020
tacaagtgca aggtctccaa caaagccctc ccagccccca tcgagaaaac catctccaaa    1080
gccaaagggc agccccgaga accacaggtg tacaccctgc ccccatcccg ggaggagatg    1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga ctcgag                              1416

<210> SEQ ID NO 39
<211> LENGTH: 759
<212> TYPE: DNA
<213> ORGANISM: Artificial Sequence
<220> FEATURE:
<223> OTHER INFORMATION: Synthetic (nucleotide sequence of light chain
      of chAbF46)
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 39
gaattcacta gtgattaatt cgccgccacc atggattcac aggcccaggt cctcatgttg    60
```

| | | |
|---|---|---|
| ctgctgctat cggtatctgg tacctgtgga gacattttga tgacccagtc tccatcctcc | 120 |
| ctgactgtgt cagcaggaga gaaggtcact atgagctgca agtccagtca gagtctttta | 180 |
| gctagtggca accaaaataa ctacttggcc tggcaccagc agaaaccagg acgatctcct | 240 |
| aaaatgctga taatttgggc atccactagg gtatctggag tccctgatcg cttcataggc | 300 |
| agtggatctg gacggatttt cactctgacc atcaacagtg tgcaggctga agatctggct | 360 |
| gtttattact gtcagcagtc ctacagcgct ccgctcacgt tcggtgctgg gaccaagctg | 420 |
| gagctgaaac gtacggtggc tgcaccatct gtcttcatct tcccgccatc tgatgagcag | 480 |
| ttgaaatctg gaactgcctc tgttgtgtgc ctgctgaata acttctatcc cagagaggcc | 540 |
| aaagtacagt ggaaggtgga taacgccctc caatcgggta actcccagga gagtgtcaca | 600 |
| gagcaggaca gcaaggacag cacctacagc ctcagcagca ccctgacgct gagcaaagca | 660 |
| gactacgaga aacacaaagt ctacgcctgc gaagtcaccc atcagggcct gagctcgccc | 720 |
| gtcacaaaga gcttcaacag gggagagtgt tgactcgag | 759 |

<210> SEQ ID NO 40
<211> LENGTH: 447
<212> TYPE: PRT
<213> ORGANISM: Artificial Sequence
<220> FEATURE:
<223> OTHER INFORMATION: Synthetic (amino acid sequence of H1-heavy)

<400> SEQUENCE: 40

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240
```

-continued

```
Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 41
<211> LENGTH: 447
<212> TYPE: PRT
<213> ORGANISM: Artificial Sequence
<220> FEATURE:
<223> OTHER INFORMATION: Synthetic (amino acid sequence of H3-heavy)

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160
```

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 42
<211> LENGTH: 447
<212> TYPE: PRT
<213> ORGANISM: Artificial Sequence
<220> FEATURE:
<223> OTHER INFORMATION: Synthetic (amino acid sequence of H4-heavy)

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
            35                  40                  45

Gly Phe Ile Arg Asn Lys Ala Asn Gly Tyr Thr Thr Glu Tyr Ser Ala
        50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                 85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 43
<211> LENGTH: 220
<212> TYPE: PRT
<213> ORGANISM: Artificial Sequence
<220> FEATURE:
<223> OTHER INFORMATION: Synthetic (amino acid sequence of H1-light)

<400> SEQUENCE: 43

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
            85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
210                 215                 220

<210> SEQ ID NO 44
<211> LENGTH: 220
<212> TYPE: PRT
<213> ORGANISM: Artificial Sequence
<220> FEATURE:
<223> OTHER INFORMATION: Synthetic (amino acid sequence of H2-light)

<400> SEQUENCE: 44

Asp Ile Val Met Thr Gln Thr Pro Leu Ser Leu Pro Val Thr Pro Gly
1               5                   10                  15

Glu Pro Ala Ser Ile Ser Cys Lys Ser Ser Gln Ser Leu Leu Ala Ser
            20                  25                  30

Gly Asn Gln Asn Asn Tyr Leu Ala Trp His Leu Gln Lys Pro Gly Gln
        35                  40                  45

Ser Pro Gln Met Leu Ile Ile Trp Ala Ser Thr Arg Val Ser Gly Val
50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
            85                  90                  95

Ser Tyr Ser Ala Pro Leu Thr Phe Gly Gln Gly Thr Lys Leu Glu Leu
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140
```

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
        180                 185                 190

Glu Lys His Lys Val Tyr Ala Cys Glu Val Thr His Gln Gly Leu Ser
    195                 200                 205

Ser Pro Val Thr Lys Ser Phe Asn Arg Gly Glu Cys
210                 215                 220

<210> SEQ ID NO 45
<211> LENGTH: 220
<212> TYPE: PRT
<213> ORGANISM: Artificial Sequence
<220> FEATURE:
<223> OTHER INFORMATION: Synthetic (amino acid sequence of H3-light)

<400> SEQUENCE: 45

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp Tyr Gln Lys Pro Gly Gln
        35                  40                  45

Pro Pro Lys Leu Leu Ile Ile Trp Ala Ser Thr Arg Val Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
        180                 185                 190

Glu Lys His Lys Val Tyr Ala Cys Glu Val Thr His Gln Gly Leu Ser
    195                 200                 205

Ser Pro Val Thr Lys Ser Phe Asn Arg Gly Glu Cys
210                 215                 220

<210> SEQ ID NO 46
<211> LENGTH: 219
<212> TYPE: PRT
<213> ORGANISM: Artificial Sequence
<220> FEATURE:
<223> OTHER INFORMATION: Synthetic (amino acid sequence of H4-light)

<400> SEQUENCE: 46

Asp Ile Gln Met Thr Gln Ser Pro Ser Ser Leu Ser Ala Ser Val Gly

```
  1               5                  10                 15
Asp Arg Val Thr Ile Thr Cys Lys Ser Ser Gln Ser Leu Leu Ala Ser
              20                 25                 30

Gly Asn Gln Asn Asn Tyr Leu Ala Trp His Gln Gln Lys Pro Gly Lys
              35                 40                 45

Ala Pro Lys Met Leu Ile Ile Trp Ala Ser Thr Arg Val Ser Gly Val
 50                 55                 60

Pro Ser Arg Phe Ser Gly Ser Gly Ser Gly Thr Asp Phe Thr Leu Thr
 65                 70                 75                 80

Ile Ser Ser Leu Gln Pro Glu Asp Phe Ala Thr Tyr Tyr Cys Gln Gln
              85                 90                 95

Ser Tyr Ser Ala Pro Leu Thr Phe Gly Gln Gly Thr Lys Val Glu Ile
              100                105                110

Lys Arg Thr Val Ala Ala Pro Ser Val Phe Ile Phe Pro Pro Ser Asp
              115                120                125

Glu Gln Leu Lys Ser Gly Thr Ala Ser Val Val Cys Leu Leu Asn Asn
              130                135                140

Phe Tyr Pro Arg Glu Ala Lys Val Gln Trp Lys Val Asp Asn Ala Leu
145                150                155                160

Gln Ser Gly Asn Ser Gln Glu Ser Val Thr Glu Gln Asp Ser Lys Asp
              165                170                175

Ser Thr Tyr Ser Leu Ser Ser Thr Leu Thr Leu Ser Lys Ala Asp Tyr
              180                185                190

Glu Lys His Lys Val Tyr Ala Cys Glu Val Thr His Gln Gly Leu Ser
              195                200                205

Ser Pro Val Thr Lys Ser Phe Asn Arg Gly Glu
              210                215
```

<210> SEQ ID NO 47
<211> LENGTH: 1350
<212> TYPE: DNA
<213> ORGANISM: Artificial Sequence
<220> FEATURE:
<223> OTHER INFORMATION: Synthetic (nucleotide sequence of H1-heavy)

<400> SEQUENCE: 47

```
gaggtgcagc tggtggagtc tgggggaggc ttggtccagc ctggagggtc cctgagactc      60
tcctgtgcag cctctggatt caccttcact gactactaca tgagctgggt ccgccaggct     120
ccagggaagg gctggagtg gttgggcttt attagaaaca agctaacgg ttacaccaca       180
gaatacagtg cgtctgtgaa aggcagattc accatctcaa gagataattc aaagaactca    240
ctgtatctgc aaatgaacag cctgaaaacc gaggacacgg ccgtgtatta ctgtgctaga    300
gataactggt tgcttactg gggtcaagga accctggtca ccgtctcctc ggctagcacc     360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagcc caaatcttgt    660
gacaaaactc acacatgccc accgtgccca gcacctgaac tcctgggggg accgtcagtc    720
ttcctcttcc cccaaaaacc caaggacacc ctcatgatct cccggacccc tgaggtcaca    780
tgcgtggtgg tggacgtgag ccacgaagac cctgaggtca agttcaactg gtacgtggac    840
```

| | |
|---|---|
| ggcgtggagg tgcataatgc caagacaaag ccgcgggagg agcagtacaa cagcacgtac | 900 |
| cgtgtggtca gcgtcctcac cgtcctgcac caggactggc tgaatggcaa ggagtacaag | 960 |
| tgcaaggtct ccaacaaagc cctcccagcc cccatcgaga aaaccatctc caaagccaaa | 1020 |
| gggcagcccc gagaaccaca ggtgtacacc ctgcccccat cccgggagga gatgaccaag | 1080 |
| aaccaggtca gcctgacctg cctggtcaaa ggcttctatc ccagcgacat cgccgtggag | 1140 |
| tgggagagca atgggcagcc ggagaacaac tacaagacca cgcctcccgt gctggactcc | 1200 |
| gacggctcct tcttcctcta cagcaagctc accgtggaca agagcaggtg gcagcagggg | 1260 |
| aacgtcttct catgctccgt gatgcatgag gctctgcaca accactacac gcagaagagc | 1320 |
| ctctccctgt ctccgggtaa atgactcgag | 1350 |

<210> SEQ ID NO 48
<211> LENGTH: 1350
<212> TYPE: DNA
<213> ORGANISM: Artificial Sequence
<220> FEATURE:
<223> OTHER INFORMATION: Synthetic (nucleotide sequence of H3-heavy)

<400> SEQUENCE: 48

| | |
|---|---|
| gaggtgcagc tggtggagtc tgggggaggc ttggtccagc ctggagggtc cctgagactc | 60 |
| tcctgtgcag cctctggatt caccttcact gactactaca tgagctgggt ccgccaggct | 120 |
| ccagggaagg ggctggagtg gttgggcttt attagaaaca agctaacgg ttacaccaca | 180 |
| gaatacagtg cgtctgtgaa aggcagattc accatctcaa gagataattc aaagaactca | 240 |
| ctgtatctgc aaatgaacag cctgcgtgct gaggacacgg ccgtgtatta ctgtgctaga | 300 |
| gataactggt ttgcttactg gggtcaagga accctggtca ccgtctcctc ggctagcacc | 360 |
| aagggcccat cggtcttccc cctggcaccc tcctccaaga gcacctctgg gggcacagcg | 420 |
| gccctgggct gcctggtcaa ggactacttc cccgaaccgg tgacggtgtc gtggaactca | 480 |
| ggcgccctga ccagcggcgt gcacaccttc ccggctgtcc tacagtcctc aggactctac | 540 |
| tccctcagca gcgtggtgac cgtgccctcc agcagcttgg gcacccagac ctacatctgc | 600 |
| aacgtgaatc acaagcccag caacaccaag gtggacaaga agttgagcc caaatcttgt | 660 |
| gacaaaactc acacatgccc accgtgccca gcacctgaac tcctgggggg accgtcagtc | 720 |
| ttcctcttcc cccaaaaacc caaggacacc ctcatgatct cccggacccc tgaggtcaca | 780 |
| tgcgtggtgg tggacgtgag ccacgaagac cctgaggtca agttcaactg gtacgtggac | 840 |
| ggcgtggagg tgcataatgc caagacaaag ccgcgggagg agcagtacaa cagcacgtac | 900 |
| cgtgtggtca gcgtcctcac cgtcctgcac caggactggc tgaatggcaa ggagtacaag | 960 |
| tgcaaggtct ccaacaaagc cctcccagcc cccatcgaga aaaccatctc caaagccaaa | 1020 |
| gggcagcccc gagaaccaca ggtgtacacc ctgcccccat cccgggagga gatgaccaag | 1080 |
| aaccaggtca gcctgacctg cctggtcaaa ggcttctatc ccagcgacat cgccgtggag | 1140 |
| tgggagagca atgggcagcc ggagaacaac tacaagacca cgcctcccgt gctggactcc | 1200 |
| gacggctcct tcttcctcta cagcaagctc accgtggaca agagcaggtg gcagcagggg | 1260 |
| aacgtcttct catgctccgt gatgcatgag gctctgcaca accactacac gcagaagagc | 1320 |
| ctctccctgt ctccgggtaa atgactcgag | 1350 |

<210> SEQ ID NO 49
<211> LENGTH: 1350
<212> TYPE: DNA
<213> ORGANISM: Artificial Sequence
<220> FEATURE:
<223> OTHER INFORMATION: Synthetic (nucleotide sequence of H4-heavy)

<400> SEQUENCE: 49

| | |
|---|---|
| gaggttcagc tggtggagtc tggcggtggc ctggtgcagc caggggggctc actccgtttg | 60 |
| tcctgtgcag cttctggctt caccttcact gattactaca tgagctgggt gcgtcaggcc | 120 |
| ccgggtaagg gcctggaatg gttgggtttt attagaaaca agctaatgg ttacacaaca | 180 |
| gagtacagtg catctgtgaa gggtcgtttc actataagca gagataattc caaaaacaca | 240 |
| ctgtacctgc agatgaacag cctgcgtgct gaggacactg ccgtctatta ttgtgctaga | 300 |
| gataactggt tgcttactg gggccaaggg actctggtca ccgtctcctc ggctagcacc | 360 |
| aagggcccat cggtcttccc cctggcaccc tcctccaaga gcacctctgg gggcacagcg | 420 |
| gccctgggct gcctggtcaa ggactacttc cccgaaccgg tgacggtgtc gtggaactca | 480 |
| ggcgccctga ccagcggcgt gcacaccttc ccggctgtcc tacagtcctc aggactctac | 540 |
| tccctcagca gcgtggtgac cgtgccctcc agcagcttgg gcacccagac ctacatctgc | 600 |
| aacgtgaatc acaagcccag caacaccaag gtggacaaga agttgagcc caaatcttgt | 660 |
| gacaaaactc acacatgccc accgtgccca gcacctgaac tcctgggggg accgtcagtc | 720 |
| ttcctcttcc ccccaaaacc caaggacacc ctcatgatct cccggacccc tgaggtcaca | 780 |
| tgcgtggtgg tggacgtgag ccacgaagac cctgaggtca agttcaactg gtacgtggac | 840 |
| ggcgtggagg tgcataatgc caagacaaag ccgcgggagg agcagtacaa cagcacgtac | 900 |
| cgtgtggtca gcgtcctcac cgtcctgcac caggactggc tgaatggcaa ggagtacaag | 960 |
| tgcaaggtct ccaacaaagc cctcccagcc cccatcgaga aaccatctc caaagccaaa | 1020 |
| gggcagcccc gagaaccaca ggtgtacacc ctgcccccat cccgggagga gatgaccaag | 1080 |
| aaccaggtca gcctgacctg cctggtcaaa ggcttctatc ccagcgacat cgccgtggag | 1140 |
| tgggagagca atgggcagcc ggagaacaac tacaagacca cgcctcccgt gctggactcc | 1200 |
| gacggctcct tcttcctcta cagcaagctc accgtggaca agagcaggtg gcagcagggg | 1260 |
| aacgtcttct catgctccgt gatgcatgag gctctgcaca accactacac gcagaagagc | 1320 |
| ctctccctgt ctccgggtaa atgactcgag | 1350 |

<210> SEQ ID NO 50
<211> LENGTH: 669
<212> TYPE: DNA
<213> ORGANISM: Artificial Sequence
<220> FEATURE:
<223> OTHER INFORMATION: Synthetic (nucleotide sequence of H1-light)

<400> SEQUENCE: 50

| | |
|---|---|
| gacatcgtga tgacccagtc tccagactcc ctggctgtgt ctctgggcga gagggccacc | 60 |
| atcaactgca gtccagcca gagtctttta gctagcggca accaaaataa ctacttagct | 120 |
| tggcaccagc agaaaccagg acagcctcct aagatgctca ttatttgggc atctacccgg | 180 |
| gtatccgggg tccctgaccg attcagtggc agcgggtctg gacagattt cactctcacc | 240 |
| atcagcagcc tgcaggctga agatgtggca gtttattact gtcagcaatc ctatagtgct | 300 |
| cctctcacgt tcggaggcgg taccaaggtg gagatcaaac gtacggtggc tgcaccatct | 360 |
| gtcttcatct tcccgccatc tgatgagcag ttgaaatctg gaactgcctc tgttgtgtgc | 420 |
| ctgctgaata acttctatcc cagagaggcc aaagtacagt ggaaggtgga taacgccctc | 480 |
| caatcgggta actcccagga gagtgtcaca gagcaggaca gcaaggacag cacctacagc | 540 |

```
ctcagcagca ccctgacgct gagcaaagca gactacgaga aacacaaagt ctacgcctgc   600
gaagtcaccc atcagggcct gagctcgccc gtcacaaaga gcttcaacag gggagagtgt   660
tgactcgag                                                          669
```

<210> SEQ ID NO 51
<211> LENGTH: 669
<212> TYPE: DNA
<213> ORGANISM: Artificial Sequence
<220> FEATURE:
<223> OTHER INFORMATION: Synthetic (nucleotide sequence of H2-light)

<400> SEQUENCE: 51

```
gatattgtga tgacccagac tccactctcc ctgcccgtca cccctggaga gccggcctcc    60
atctcctgca gtccagtca gagtctttta gctagtggca accaaaataa ctacttggcc   120
tggcacctgc agaagccagg gcagtctcca cagatgctga tcatttgggc atccactagg   180
gtatctggag tcccagacag gttcagtggc agtgggtcag gcactgattt cacactgaaa   240
atcagcaggg tggaggctga ggatgttgga gtttattact gccagcagtc ctacagcgct   300
ccgctcacgt tcggacaggg taccaagctg gagctcaaac gtacggtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca ccctgacgct gagcaaagca gactacgaga aacacaaagt ctacgcctgc   600
gaagtcaccc atcagggcct gagctcgccc gtcacaaaga gcttcaacag gggagagtgt   660
tgactcgag                                                          669
```

<210> SEQ ID NO 52
<211> LENGTH: 669
<212> TYPE: DNA
<213> ORGANISM: Artificial Sequence
<220> FEATURE:
<223> OTHER INFORMATION: Synthetic (nucleotide sequence of H3-light)

<400> SEQUENCE: 52

```
gacatcgtga tgacccagtc tccagactcc ctggctgtgt ctctgggcga gagggccacc    60
atcaactgca gtccagcca gagtctttta gctagcggca accaaaataa ctacttagct   120
tggtaccagc agaaaccagg acagcctcct aagctgctca ttatttgggc atctacccgg   180
gtatccgggg tccctgaccg attcagtggc agcgggtctg ggacagattt cactctcacc   240
atcagcagcc tgcaggctga agatgtggca gtttattact gtcagcaatc ctatagtgct   300
cctctcacgt tcggaggcgg taccaaggtg gagatcaaac gtacggtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca ccctgacgct gagcaaagca gactacgaga aacacaaagt ctacgcctgc   600
gaagtcaccc atcagggcct gagctcgccc gtcacaaaga gcttcaacag gggagagtgt   660
tgactcgag                                                          669
```

<210> SEQ ID NO 53
<211> LENGTH: 669
<212> TYPE: DNA
<213> ORGANISM: Artificial Sequence
<220> FEATURE:
<223> OTHER INFORMATION: Synthetic (nucleotide sequence of H4-light)

<400> SEQUENCE: 53

| | | |
|---|---|---|
| gatatccaga tgacccagtc cccgagctcc ctgtccgcct ctgtgggcga tagggtcacc | 60 |
| atcacctgca agtccagtca gagtctttta gctagtggca accaaaataa ctacttggcc | 120 |
| tggcaccaac agaaaccagg aaaagctccg aaaatgctga ttatttgggc atccactagg | 180 |
| gtatctggag tcccttctcg cttctctgga tccgggtctg ggacggattt cactctgacc | 240 |
| atcagcagtc tgcagccgga agacttcgca acttattact gtcagcagtc ctacagcgct | 300 |
| ccgctcacgt tcggacaggg taccaaggtg gagatcaaac gtacggtggc tgcaccatct | 360 |
| gtcttcatct tcccgccatc tgatgagcag ttgaaatctg gaactgcctc tgttgtgtgc | 420 |
| ctgctgaata acttctatcc cagagaggcc aaagtacagt ggaaggtgga taacgccctc | 480 |
| caatcgggta actcccagga gagtgtcaca gagcaggaca gcaaggacag cacctacagc | 540 |
| ctcagcagca ccctgacgct gagcaaagca gactacgaga aacacaaagt ctacgcctgc | 600 |
| gaagtcaccc atcagggcct gagctcgccc gtcacaaaga gcttcaacag gggagagtgt | 660 |
| tgactcgag | 669 |

<210> SEQ ID NO 54
<211> LENGTH: 23
<212> TYPE: PRT
<213> ORGANISM: Artificial Sequence
<220> FEATURE:
<223> OTHER INFORMATION: Synthetic (linker between VH and VL)

<400> SEQUENCE: 54

Gly Leu Gly Gly Leu Gly Gly Gly Gly Ser Gly Gly Gly Gly Ser Gly
1               5                   10                  15

Gly Ser Ser Gly Val Gly Ser
            20

<210> SEQ ID NO 55
<211> LENGTH: 1088
<212> TYPE: DNA
<213> ORGANISM: Artificial Sequence
<220> FEATURE:
<223> OTHER INFORMATION: Synthetic (polynucleotide encoding scFv of huAbF46 antibody)

<400> SEQUENCE: 55

| | | |
|---|---|---|
| gctagcgttt tagcagaagt tcaattggtt gaatctggtg gtggtttggt tcaaccaggt | 60 |
| ggttctttga gattgtcttg tgctgcttct ggttttactt tcaccgatta ttacatgtcc | 120 |
| tgggttagac aagctccagg taaaggtttg gaatggttgg gtttcattag aaacaaggct | 180 |
| aacggttaca ctaccgaata ttctgcttct gttaagggta gattcaccat ttctagagac | 240 |
| aactctaaga cacccttgta cttgcaaatg aactccttga gagctgaaga tactgctgtt | 300 |
| tattactgcg ctagagataa ttggtttgct tattgggtc aaggtactt ggttactgtt | 360 |
| tcttctggcc tcgggggcct cggaggagga ggtagtggcg gaggaggctc cggtggatcc | 420 |
| agcggtgtgg gttccgatat tcaaatgacc caatctccat cttctttgtc tgcttcagtt | 480 |
| ggtgatagag ttaccattac ttgtaagtcc tcccaatctt gttggcttc tggtaatcag | 540 |
| aacaattact ggcttggca tcaacaaaaa ccaggtaaag ctccaaagat gttgattatt | 600 |
| tgggcttcta ccagagtttc tggtgttcca tctagatttt ctggtctgg ttccggtact | 660 |
| gattttactt tgaccatttc atccttgcaa ccagaagatt cgctactta ctactgtcaa | 720 |

```
caatcttact ctgctccatt gacttttggt caaggtacaa aggtcgaaat caagagagaa    780
ttcggtaagc ctatccctaa ccctctcctc ggtctcgatt ctacgggtgg tggtggatct    840
ggtggtggtg gttctggtgg tggtggttct caggaactga caactatatg cgagcaaatc    900
ccctcaccaa ctttagaatc gacgccgtac tctttgtcaa cgactactat tttggccaac    960
gggaaggcaa tgcaaggagt ttttgaatat acaaatcag taacgtttgt cagtaattgc    1020
ggttctcacc cctcaacaac tagcaaaggc agccccataa acacacagta tgttttttga    1080
gtttaaac                                                            1088
```

<210> SEQ ID NO 56
<211> LENGTH: 5597
<212> TYPE: DNA
<213> ORGANISM: Artificial Sequence
<220> FEATURE:
<223> OTHER INFORMATION: Synthetic (expression vector including polynucleotide encoding scFv of huAbF46 antibody)
<220> FEATURE:
<221> NAME/KEY: misc_difference
<222> LOCATION: (573)..(578)
<223> OTHER INFORMATION: NheI restriction site
<220> FEATURE:
<221> NAME/KEY: misc_difference
<222> LOCATION: (588)..(938)
<223> OTHER INFORMATION: huAbF46 VH
<220> FEATURE:
<221> NAME/KEY: misc_difference
<222> LOCATION: (939)..(1007)
<223> OTHER INFORMATION: linker
<220> FEATURE:
<221> NAME/KEY: misc_difference
<222> LOCATION: (1008)..(1349)
<223> OTHER INFORMATION: huAbF46 VL
<220> FEATURE:
<221> NAME/KEY: misc_difference
<222> LOCATION: (1350)..(1355)
<223> OTHER INFORMATION: EcoRI restriction site
<220> FEATURE:
<221> NAME/KEY: misc_difference
<222> LOCATION: (1356)..(1397)
<223> OTHER INFORMATION: V5 epitope
<220> FEATURE:
<221> NAME/KEY: misc_difference
<222> LOCATION: (1398)..(1442)
<223> OTHER INFORMATION: (G4S)3 linker
<220> FEATURE:
<221> NAME/KEY: misc_difference
<222> LOCATION: (1443)..(1649)
<223> OTHER INFORMATION: Aga2
<220> FEATURE:
<221> NAME/KEY: misc_difference
<222> LOCATION: (1650)..(1652)
<223> OTHER INFORMATION: TGA(stop codon)
<220> FEATURE:
<221> NAME/KEY: misc_difference
<222> LOCATION: (1653)..(1660)
<223> OTHER INFORMATION: PmeI restriction site

<400> SEQUENCE: 56

```
acggattaga agccgccgag cgggtgacag ccctccgaag gaagactctc ctccgtgcgt     60
cctcgtcttc accggtcgcg ttcctgaaac gcagatgtgc ctcgcgccgc actgctccga    120
acaataaaga ttctacaata ctagctttta tggttatgaa gaggaaaaat tggcagtaac    180
ctggccccac aaaccttcaa atgaacgaat caaattaaca accataggat gataatgcga    240
ttagtttttt agccttattt ctgggggtaat taatcagcga agcgatgatt tttgatctat    300
taacagatat ataaatgcaa aaactgcata accactttaa ctaatacttt caacattttc    360
ggtttgtatt acttcttatt caaatgtaat aaaagtatca acaaaaaatt gttaatatac    420
```

```
ctctatactt taacgtcaag gagaaaaaac cccggatcgg actactagca gctgtaatac    480
gactcactat agggaatatt aagctaattc tacttcatac attttcaatt aagatgcagt    540
tacttcgctg tttttcaata ttttctgtta ttgctagcgt tttagcagaa gttcaattgg    600
ttgaatctgg tggtggtttg gttcaaccag gtggttcttt gagattgtct tgtgctgctt    660
ctggttttac tttcaccgat tattacatgt cctgggttag acaagctcca ggtaaaggtt    720
tggaatggtt gggtttcatt agaaacaagg ctaacggtta cactaccgaa tattctgctt    780
ctgttaaggg tagattcacc atttctagag acaactctaa gaacaccttg tacttgcaaa    840
tgaactcctt gagagctgaa gatactgctg tttattactg cgctagagat aattggtttg    900
cttattgggg tcaaggtact ttggttactg tttcttctgg cctcggggc ctcggaggag    960 gaggtagtgg cggaggaggc tccggtggat ccagcggtgt gggttccgat attcaaatga   1020
cccaatctcc atcttctttg tctgcttcag ttggtgatag agttaccatt acttgtaagt   1080
cctcccaatc tttgttggct tctggtaatc agaacaatta cttggcttgg catcaacaaa   1140
aaccaggtaa agctccaaag atgttgatta tttgggcttc taccagagtt tctggtgttc   1200
catctagatt ttctggttct ggttccggta ctgattttac tttgaccatt tcatccttgc   1260
aaccagaaga tttcgctact tactactgtc aacaatctta ctctgctcca ttgacttttg   1320
gtcaaggtac aaaggtcgaa atcaagagag aattcggtaa gcctatccct aaccctctcc   1380
tcggtctcga ttctacgggt ggtggtggat ctggtggtgg tggttctggt ggtggtggtt   1440
ctcaggaact gacaactata tgcgagcaaa tcccctcacc aactttagaa tcgacgccgt   1500
actctttgtc aacgactact attttggcca acgggaaggc aatgcaagga ttttttgaat   1560
attacaaatc agtaacgttt gtcagtaatt gcggttctca cccctcaaca actagcaaag   1620
gcagccccat aaacacacag tatgttttt gagtttaaac ccgctgatct gataacaaca   1680
gtgtagatgt aacaaaatcg actttgttcc cactgtactt ttagctcgta caaaatacaa   1740 tatactttc atttctccgt aaacaacatg ttttcccatg taatatcctt ttctattttt    1800
cgttccgtta ccaactttac acatacttta tatagctatt cacttctata cactaaaaaa   1860
ctaagacaat tttaattttg ctgcctgcca tatttcaatt tgttataaat tcctataatt   1920
tatcctatta gtagctaaaa aaagatgaat gtgaatcgaa tcctaagaga attgggcaag   1980
tgcacaaaca atacttaaat aaatactact cagtaataac ctatttctta gcattttga    2040 cgaaatttgc tattttgtta gagtctttta caccatttgt ctccacacct ccgcttacat   2100
caacaccaat aacgccattt aatctaagcg catcaccaac attttctggc gtcagtccac   2160
cagctaacat aaaatgtaag ctctcggggc tctcttgcct tccaacccag tcagaaatcg   2220
agttccaatc caaagttcca cctgtcccac ctgcttctga atcaaacaag ggaataaacg   2280
aatgaggttt ctgtgaagct gcactgagta gtatgttgca gtcttttgga aatacgagtc   2340
ttttaataac tggcaaaccg aggaactctt ggtattcttg ccacgactca tctccgtgca   2400
gttggacgat atcaatgccg taatcattga ccagagccaa acatcctcc ttaggttgat    2460 tacgaaacac gccaaccaag tatttcggag tgcctgaact atttttatat gcttttacaa   2520
gacttgaaat tttccttgca ataaccgggt caattgttct ctttctattg ggcacacata   2580
taatacccag caagtcagca tcggaatcta gagcacattc tgcggcctct gtgctctgca   2640
agccgcaaac tttcaccaat ggaccagaac tacctgtgaa attaataaca gacatactcc   2700
aagctgcctt tgtgtgctta atcacgtata ctcacgtgct caatagtcac caatgccctc   2760
```

```
cctcttggcc ctctcctttt cttttttcga ccgaatttct tgaagacgaa agggcctcgt    2820
gatacgccta tttttatagg ttaatgtcat gataataatg gtttcttagg acggatcgct    2880
tgcctgtaac ttacacgcgc ctcgtatctt ttaatgatgg ataaatttgg gaatttactc    2940
tgtgtttatt tattttatg ttttgtattt ggatttaga aagtaaataa agaaggtaga      3000
agagttacgg aatgaagaaa aaaaaataaa caaaggttta aaaaatttca acaaaaagcg    3060
tactttacat atatatttat tagacaagaa aagcagatta aatagatata cattcgatta    3120
acgataagta aaatgtaaaa tcacaggatt ttcgtgtgtg gtcttctaca cagacaagat    3180
gaaacaattc ggcattaata cctgagagca ggaagagcaa gataaaaggt agtatttgtt    3240
ggcgatcccc ctagagtctt ttacatcttc ggaaaacaaa aactatttt tctttaattt     3300 cttttttac tttctatttt taatttatat atttatatta aaaatttaa attataatta     3360 ttttatagc acgtgatgaa aaggacccag gtggcacttt tcggggaaat gtgcgcggaa    3420 ccccctatttg tttattttc taaatacatt caaatatgta tccgctcatg agacaataac    3480
cctgataaat gcttcaataa tattgaaaaa ggaagagtat gagtattcaa catttccgtg    3540
tcgcccttat tcccttttt gcggcatttt gccttcctgt ttttgctcac ccagaaacgc    3600
tggtgaaagt aaaagatgct gaagatcagt tgggtgcacg agtgggttac atcgaactgg    3660
atctcaacag cggtaagatc cttgagagtt ttcgccccga agaacgtttt ccaatgatga    3720 gcactttttaa agttctgcta tgtggcgcgg tattatcccg tgttgacgcc gggcaagagc    3780
aactcggtcg ccgcatacac tattctcaga atgacttggt tgagtactca ccagtcacag    3840
aaaagcatct tacggatggc atgacagtaa gagaattatg cagtgctgcc ataaccatga    3900
gtgataacac tgcggccaac ttacttctga caacgatcgg aggaccgaag gagctaaccg    3960
cttttttgca acatggggg gatcatgtaa ctcgccttga tcgttgggaa ccggagctga    4020
atgaagccat accaaacgac gagcgtgaca ccacgatgcc tgtagcaatg gcaacaacgt    4080
tgcgcaaact attaactggc gaactactta ctctagcttc ccggcaacaa ttaatagact    4140
ggatggaggc ggataaagtt gcaggaccac ttctgcgctc ggcccttccg gctggctggt    4200
ttattgctga taaatctgga gccggtgagc gtgggtctcg cggtatcatt gcagcactgg    4260
ggccagatgg taagccctcc cgtatcgtag ttatctacac gacgggcagt caggcaacta    4320
tggatgaacg aaatagacag atcgctgaga taggtgcctc actgattaag cattggtaac    4380
tgtcagacca gtttactca tatatacttt agattgattt aaaacttcat ttttaattta    4440
aaaggatcta ggtgaagatc ctttttgata atctcatgac caaaatccct taacgtgagt    4500
tttcgttcca ctgagcgtca gaccccgtag aaaagatcaa aggatcttct tgagatcctt    4560 ttttctgcg cgtaatctgc tgcttgcaaa caaaaaaacc accgctacca gcggtggttt    4620
gtttgccgga tcaagagcta ccaactcttt ttccgaaggt aactggcttc agcagagcgc    4680
agataccaaa tactgtcctt ctagtgtagc cgtagttagg ccaccacttc aagaactctg    4740
tagcaccgcc tacatacctc gctctgctaa tcctgttacc agtggctgct gccagtggcg    4800
ataagtcgtg tcttaccggg ttggactcaa gacgatagtt accggataag gcgcagcggt    4860
cgggctgaac ggggggttcg tgcacacagc ccagcttgga gcgaacgacc tacaccgaac    4920
tgagatacct acagcgtgag cattgagaaa gcgccacgct tcccgaaggg agaaaggcgg    4980
acaggtatcc ggtaagcggc agggtcggaa caggagagcg cacgagggag cttccagggg    5040
ggaacgcctg gtatctttat agtcctgtcg ggtttcgcca cctctgactt gagcgtcgat    5100 tttgtgatg ctcgtcaggg gggccgagcc tatggaaaaa cgccagcaac gcggcctttt    5160
```

| | |
|---|---|
| tacggttcct ggccttttgc tggccttttg ctcacatgtt ctttcctgcg ttatcccctg | 5220 |
| attctgtgga taaccgtatt accgcctttg agtgagctga taccgctcgc cgcagccgaa | 5280 |
| cgaccgagcg cagcgagtca gtgagcgagg aagcggaaga gcgcccaata cgcaaaccgc | 5340 |
| ctctccccgc gcgttggccg attcattaat gcagctggca cgacaggttt cccgactgga | 5400 |
| aagcgggcag tgagcgcaac gcaattaatg tgagttacct cactcattag gcacccagg | 5460 |
| ctttacactt tatgcttccg gctcctatgt tgtgtggaat tgtgagcgga taacaatttc | 5520 |
| acacaggaaa cagctatgac catgattacg ccaagctcgg aattaaccct cactaaaggg | 5580 |
| aacaaaagct ggctagt | 5597 |

<210> SEQ ID NO 57
<211> LENGTH: 13
<212> TYPE: PRT
<213> ORGANISM: Artificial Sequence
<220> FEATURE:
<223> OTHER INFORMATION: Synthetic (U6-HC7 hinge)

<400> SEQUENCE: 57

Glu Pro Lys Ser Cys Asp Cys His Cys Pro Pro Cys Pro
1               5                   10

<210> SEQ ID NO 58
<211> LENGTH: 435
<212> TYPE: DNA
<213> ORGANISM: Artificial Sequence
<220> FEATURE:
<223> OTHER INFORMATION: Synthetic (polynucleotide encoding CDR-L3
      derived from L3-1 clone)

<400> SEQUENCE: 58

| | |
|---|---|
| gaattcacta gtgattaatt cgccgccacc atggattcac aggcccaggt cctcatgttg | 60 |
| ctgctgctat cggtatctgg tacctgtgga gatatccaga tgacccagtc cccgagctcc | 120 |
| ctgtccgcct ctgtgggcga tagggtcacc atcacctgca agtccagtca gagtctttta | 180 |
| gctagtggca accaaaataa ctacttggcc tggcaccaac agaaaccagg aaaagctccg | 240 |
| aaaatgctga ttatttgggc atccactagg gtatctggag tcccttctcg cttctctgga | 300 |
| tccgggtctg gacggattt cactctgacc atcagcagtc tgcagccgga agacttcgca | 360 |
| acttattact gtcagcagtc ctacagccgc ccgtacacgt tcggcaggg taccaaggtg | 420 |
| gagatcaaac gtacg | 435 |

<210> SEQ ID NO 59
<211> LENGTH: 435
<212> TYPE: DNA
<213> ORGANISM: Artificial Sequence
<220> FEATURE:
<223> OTHER INFORMATION: Synthetic (polynucleotide encoding CDR-L3
      derived from L3-2 clone)

<400> SEQUENCE: 59

| | |
|---|---|
| gaattcacta gtgattaatt cgccgccacc atggattcac aggcccaggt cctcatgttg | 60 |
| ctgctgctat cggtatctgg tacctgtgga gatatccaga tgacccagtc cccgagctcc | 120 |
| ctgtccgcct ctgtgggcga tagggtcacc atcacctgca agtccagtca gagtctttta | 180 |
| gctagtggca accaaaataa ctacttggcc tggcaccaac agaaaccagg aaaagctccg | 240 |
| aaaatgctga ttatttgggc atccactagg gtatctggag tcccttctcg cttctctgga | 300 |
| tccgggtctg gacggattt cactctgacc atcagcagtc tgcagccgga agacttcgca | 360 |

```
acttattact gtgggcagtc ctacagccgt ccgctcacgt tcggacaggg taccaaggtg      420
gagatcaaac gtacg                                                      435
```

<210> SEQ ID NO 60
<211> LENGTH: 435
<212> TYPE: DNA
<213> ORGANISM: Artificial Sequence
<220> FEATURE:
<223> OTHER INFORMATION: Synthetic (polynucleotide encoding CDR-L3
      derived from L3-3 clone)

<400> SEQUENCE: 60

```
gaattcacta gtgattaatt cgccgccacc atggattcac aggcccaggt cctcatgttg       60
ctgctgctat cggtatctgg tacctgtgga gatatccaga tgacccagtc cccgagctcc      120
ctgtccgcct ctgtgggcga tagggtcacc atcacctgca agtccagtca gagtctttta      180
gctagtggca accaaaataa ctacttggcc tggcaccaac agaaaccagg aaaagctccg      240
aaaatgctga ttatttgggc atccactagg gtatctggag tcccttctcg cttctctgga      300
tccgggtctg ggacggattt cactctgacc atcagcagtc tgcagccgga agacttcgca      360
acttattact gtgcacagtc ctacagccat ccgttctctt tcggacaggg taccaaggtg      420
gagatcaaac gtacg                                                      435
```

<210> SEQ ID NO 61
<211> LENGTH: 435
<212> TYPE: DNA
<213> ORGANISM: Artificial Sequence
<220> FEATURE:
<223> OTHER INFORMATION: Synthetic (polynucleotide encoding CDR-L3
      derived from L3-5 clone)

<400> SEQUENCE: 61

```
gaattcacta gtgattaatt cgccgccacc atggattcac aggcccaggt cctcatgttg       60
ctgctgctat cggtatctgg tacctgtgga gatatccaga tgacccagtc cccgagctcc      120
ctgtccgcct ctgtgggcga tagggtcacc atcacctgca agtccagtca gagtctttta      180
gctagtggca accaaaataa ctacttggcc tggcaccaac agaaaccagg aaaagctccg      240
aaaatgctga ttatttgggc atccactagg gtatctggag tcccttctcg cttctctgga      300
tccgggtctg ggacggattt cactctgacc atcagcagtc tgcagccgga agacttcgca      360
acttattact gtcagcagtc ctacagccgc ccgtttacgt tcggacaggg taccaaggtg      420
gagatcaaac gtacg                                                      435
```

<210> SEQ ID NO 62
<211> LENGTH: 462
<212> TYPE: PRT
<213> ORGANISM: Artificial Sequence
<220> FEATURE:
<223> OTHER INFORMATION: Synthetic (polypeptide consisting of heavy
      chain of huAbF46-H4-A1, U6-HC7 hinge and constant region of
      human IgG1)

<400> SEQUENCE: 62

Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
            20                  25                  30

Gly Ser Leu Arg Leu Ser Cys Ala Ala Ser Gly Phe Thr Phe Thr Asp
        35                  40                  45

-continued

Tyr Tyr Met Ser Trp Val Arg Gln Ala Pro Gly Lys Gly Leu Glu Trp
         50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
                100                 105                 110

Tyr Tyr Cys Ala Arg Asp Asn Trp Phe Ala Tyr Trp Gly Gln Gly Thr
             115                 120                 125

Leu Val Thr Val Ser Ser Ala Ser Thr Lys Gly Pro Ser Val Phe Pro
         130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                 165                 170                 175

Ser Gly Ala Leu Thr Ser Gly Val His Thr Phe Pro Ala Val Leu Gln
                 180                 185                 190

Ser Ser Gly Leu Tyr Ser Leu Ser Ser Val Val Thr Val Pro Ser Ser
             195                 200                 205

Ser Leu Gly Thr Gln Thr Tyr Ile Cys Asn Val Asn His Lys Pro Ser
         210                 215                 220

Asn Thr Lys Val Asp Lys Lys Val Glu Pro Lys Ser Cys Asp Cys His
225                 230                 235                 240

Cys Pro Pro Cys Pro Ala Pro Glu Leu Leu Gly Gly Pro Ser Val Phe
                 245                 250                 255

Leu Phe Pro Pro Lys Pro Lys Asp Thr Leu Met Ile Ser Arg Thr Pro
                 260                 265                 270

Glu Val Thr Cys Val Val Val Asp Val Ser His Glu Asp Pro Glu Val
             275                 280                 285

Lys Phe Asn Trp Tyr Val Asp Gly Val Glu Val His Asn Ala Lys Thr
         290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                 325                 330                 335

Lys Val Ser Asn Lys Ala Leu Pro Ala Pro Ile Glu Lys Thr Ile Ser
                 340                 345                 350

Lys Ala Lys Gly Gln Pro Arg Glu Pro Gln Val Tyr Thr Leu Pro Pro
             355                 360                 365

Ser Arg Glu Glu Met Thr Lys Asn Gln Val Ser Leu Thr Cys Leu Val
         370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                 405                 410                 415

Gly Ser Phe Phe Leu Tyr Ser Lys Leu Thr Val Asp Lys Ser Arg Trp
                 420                 425                 430

Gln Gln Gly Asn Val Phe Ser Cys Ser Val Met His Glu Ala Leu His
             435                 440                 445

Asn His Tyr Thr Gln Lys Ser Leu Ser Leu Ser Pro Gly Lys
         450                 455                 460

<210> SEQ ID NO 63
<211> LENGTH: 1410
<212> TYPE: DNA
<213> ORGANISM: Artificial Sequence
<220> FEATURE:
<223> OTHER INFORMATION: Synthetic (polynucleotide encoding polypeptide consisting of heavy chain of huAbF46-H4-A1, U6-HC7 hinge and constant region of human IgG1)

<400> SEQUENCE: 63

```
gaattcgccg ccaccatgga atggagctgg gttttcctcg taacactttt aaatggtatc      60
cagtgtgagg ttcagctggt ggagtctggc ggtggcctgg tgcagccagg gggctcactc     120
cgtttgtcct gtgcagcttc tggcttcacc ttcactgatt actacatgag ctgggtgcgt     180
caggccccgg gtaagggcct ggaatggttg ggttttatta gaaacaaagc taatggttac     240
acaacagagt acagtgcatc tgtgaagggt cgtttcacta agcagaga taattccaaa      300
aacacactgt acctgcagat gaacagcctg cgtgctgagg acactgccgt ctattattgt     360
gctagagata actggtttgc ttactggggc aagggactc tggtcaccgt ctcctcggct      420
agcaccaagg gcccatcggt cttccccctg gcaccctcct ccaagagcac ctctggggc      480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa     720
agctgcgatt gccactgtcc tccatgtcca gcacctgaac tcctgggggg accgtcagtc     780
ttcctcttcc ccccaaaacc caaggacacc ctcatgatct cccggacccc tgaggtcaca     840
tgcgtggtgg tggacgtgag ccacgaagac cctgaggtca agttcaactg gtacgtggac     900
ggcgtggagg tgcataatgc caagacaaag ccgcgggagg agcagtacaa cagcacgtac     960
cgtgtggtca gcgtcctcac cgtcctgcac caggactggc tgaatggcaa ggagtacaag    1020
tgcaaggtct ccaacaaagc cctcccagcc cccatcgaga aaaccatctc caaagccaaa    1080
gggcagcccc gagaaccaca ggtgtacacc ctgcccccat cccgggagga gatgaccaag    1140
aaccaggtca gcctgacctg cctggtcaaa ggcttctatc ccagcgacat cgccgtggag    1200
tgggagagca atgggcagcc ggagaacaac tacaagacca cgcctcccgt gctggactcc    1260
gacggctcct tcttcctcta cagcaagctc accgtggaca agagcaggtg gcagcagggg    1320
aacgtcttct catgctccgt gatgcatgag gctctgcaca accactacac gcagaagagc    1380
ctctccctgt ctccgggtaa atgactcgag                                      1410
```

<210> SEQ ID NO 64
<211> LENGTH: 461
<212> TYPE: PRT
<213> ORGANISM: Artificial Sequence
<220> FEATURE:
<223> OTHER INFORMATION: Synthetic (polypeptide consisting of heavy chain of huAbF46-H4-A1, human IgG2 hinge and constant region of human IgG1)

<400> SEQUENCE: 64

```
Met Glu Trp Ser Trp Val Phe Leu Val Thr Leu Leu Asn Gly Ile Gln
 1               5                  10                  15

Cys Glu Val Gln Leu Val Glu Ser Gly Gly Gly Leu Val Gln Pro Gly
            20                  25                  30

Gly Ser Leu Arg Leu Ser Cys Ala Ala Ser Gly Phe Thr Phe Thr Asp
```

```
                35                  40                  45
Tyr Tyr Met Ser Trp Val Arg Gln Ala Pro Gly Lys Gly Leu Glu Trp
 50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
                100                 105                 110

Tyr Tyr Cys Ala Arg Asp Asn Trp Phe Ala Tyr Trp Gly Gln Gly Thr
                115                 120                 125

Leu Val Thr Val Ser Ser Ala Ser Thr Lys Gly Pro Ser Val Phe Pro
130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
                180                 185                 190

Ser Ser Gly Leu Tyr Ser Leu Ser Ser Val Val Thr Val Pro Ser Ser
                195                 200                 205

Ser Leu Gly Thr Gln Thr Tyr Ile Cys Asn Val Asn His Lys Pro Ser
210                 215                 220

Asn Thr Lys Val Asp Lys Lys Val Glu Arg Lys Cys Cys Val Glu Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
                260                 265                 270

Val Thr Cys Val Val Val Asp Val Ser His Glu Asp Pro Glu Val Lys
                275                 280                 285

Phe Asn Trp Tyr Val Asp Gly Val Glu Val His Asn Ala Lys Thr Lys
290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
                340                 345                 350

Ala Lys Gly Gln Pro Arg Glu Pro Gln Val Tyr Thr Leu Pro Pro Ser
                355                 360                 365

Arg Glu Glu Met Thr Lys Asn Gln Val Ser Leu Thr Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
                420                 425                 430

Gln Gly Asn Val Phe Ser Cys Ser Val Met His Glu Ala Leu His Asn
                435                 440                 445

His Tyr Thr Gln Lys Ser Leu Ser Leu Ser Pro Gly Lys
                450                 455                 460
```

<210> SEQ ID NO 65
<211> LENGTH: 1407
<212> TYPE: DNA
<213> ORGANISM: Artificial Sequence
<220> FEATURE:
<223> OTHER INFORMATION: Synthetic (polynucleotide encoding polypeptide
    consisting of heavy chain of huAbF46-H4-A1, human IgG2 hinge and
    constant region of human IgG1)

<400> SEQUENCE: 65

```
gaattcgccg ccaccatgga atggagctgg gttttctcg taacactttt aaatggtatc      60
cagtgtgagg ttcagctggt ggagtctggc ggtggcctgg tgcagccagg gggctcactc    120
cgtttgtcct gtgcagcttc tggcttcacc ttcactgatt actacatgag ctgggtgcgt    180
caggccccgg gtaagggcct ggaatggttg ggttttatta gaaacaaagc taatggttac    240
acaacagagt acagtgcatc tgtgaagggt cgtttcacta agcagaga taattccaaa     300
aacacactgt acctgcagat gaacagcctg cgtgctgagg acactgccgt ctattattgt    360
gctagagata actggtttgc ttactggggc caagggactc tggtcaccgt ctcctcggct    420
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagaggaag    720
tgctgtgtgg agtgcccccc ctgcccagca cctgaactcc tggggggacc gtcagtcttc    780
ctcttccccc caaaacccaa ggacaccctc atgatctccc ggacccctga ggtcacatgc    840
gtggtggtgg acgtgagcca cgaagaccct gaggtcaagt tcaactggta cgtggacggc    900
gtggaggtgc ataatgccaa gacaaagccg cgggaggagc agtacaacag cacgtaccgt    960
gtggtcagcg tcctcaccgt cctgcaccag gactggctga atggcaagga gtacaagtgc   1020
aaggtctcca acaaagccct cccagccccc atcgagaaaa ccatctccaa agccaaaggg   1080
cagccccgag aaccacaggt gtacaccctg cccccatccc gggaggagat gaccaagaac   1140
caggtcagcc tgacctgcct ggtcaaaggc ttctatccca gcgacatcgc cgtggagtgg   1200
gagagcaatg ggcagccgga gaacaactac aagaccacgc ctcccgtgct ggactccgac   1260
ggctccttct tcctctacag caagctcacc gtggacaaga gcaggtggca gcagggaac    1320
gtcttctcat gctccgtgat gcatgaggct ctgcacaacc actacacgca gaagagcctc   1380
tccctgtctc cgggtaaatg actcgag                                       1407
```

<210> SEQ ID NO 66
<211> LENGTH: 460
<212> TYPE: PRT
<213> ORGANISM: Artificial Sequence
<220> FEATURE:
<223> OTHER INFORMATION: Synthetic (polypeptide consisting of heavy
    chain of huAbF46-H4-A1, human IgG2 hinge and constant region of
    human IgG2)

<400> SEQUENCE: 66

Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
            20                  25                  30

```
Gly Ser Leu Arg Leu Ser Cys Ala Ala Ser Gly Phe Thr Phe Thr Asp
             35                  40                  45

Tyr Tyr Met Ser Trp Val Arg Gln Ala Pro Gly Lys Gly Leu Glu Trp
 50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
                100                 105                 110

Tyr Tyr Cys Ala Arg Asp Asn Trp Phe Ala Tyr Trp Gly Gln Gly Thr
            115                 120                 125

Leu Val Thr Val Ser Ser Ala Ser Thr Lys Gly Pro Ser Val Phe Pro
130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
                180                 185                 190

Ser Ser Gly Leu Tyr Ser Leu Ser Ser Val Val Thr Val Pro Ser Ser
            195                 200                 205

Asn Phe Gly Thr Gln Thr Tyr Thr Cys Asn Val Asp His Lys Pro Ser
        210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
                245                 250                 255

Pro Pro Lys Pro Lys Asp Thr Leu Met Ile Ser Arg Thr Pro Glu Val
                260                 265                 270

Thr Cys Val Val Val Asp Val Ser His Glu Asp Pro Glu Val Gln Phe
            275                 280                 285

Asn Trp Tyr Val Asp Gly Val Glu Val His Asn Ala Lys Thr Lys Pro
        290                 295                 300

Arg Glu Glu Gln Phe Asn Ser Thr Phe Arg Val Val Ser Val Leu Thr
305                 310                 315                 320

Val Val His Gln Asp Trp Leu Asn Gly Lys Glu Tyr Lys Cys Lys Val
                325                 330                 335

Ser Asn Lys Gly Leu Pro Ala Pro Ile Glu Lys Thr Ile Ser Lys Thr
                340                 345                 350

Lys Gly Gln Pro Arg Glu Pro Gln Val Tyr Thr Leu Pro Pro Ser Arg
            355                 360                 365

Glu Glu Met Thr Lys Asn Gln Val Ser Leu Thr Cys Leu Val Lys Gly
        370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Met Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
```

<210> SEQ ID NO 67
<211> LENGTH: 1404
<212> TYPE: DNA
<213> ORGANISM: Artificial Sequence
<220> FEATURE:
<223> OTHER INFORMATION: Synthetic (polynucleotide encoding polypeptide consisting of heavy chain of huAbF46-H4-A1, human IgG2 hinge and constant region of human IgG2)

<400> SEQUENCE: 67

```
gaattcgccg ccaccatgga atggagctgg gttttctcg taacactttt aaatggtatc      60
cagtgtgagg ttcagctggt ggagtctggc ggtggcctgg tgcagccagg gggctcactc     120
cgtttgtcct gtgcagcttc tggcttcacc ttcactgatt actacatgag ctgggtgcgt     180
caggccccgg gtaagggcct ggaatggttg ggttttatta gaaacaaagc taatggttac     240
acaacagagt acagtgcatc tgtgaagggt cgtttcacta agcagaga taattccaaa      300
aacacactgt acctgcagat gaacagcctg cgtgctgagg acactgccgt ctattattgt     360
gctagagata actggtttgc ttactggggc caagggactc tggtcaccgt ctcctcggct     420
agcaccaagg gcccatcggt cttccccctg gcgccctgct ccaggagcac ctccgagagc     480
acagcggccc tgggctgcct ggtcaaggac tacttccccg aaccggtgac ggtgtcgtgg     540
aactcaggcg ctctgaccag cggcgtgcac accttcccag ctgtcctaca gtcctcagga     600
ctctactccc tcagcagcgt ggtgaccgtg ccctccagca acttcggcac ccagacctac     660
acctgcaacg tagatcacaa gcccagcaac accaaggtgg acaagacagt tgagcgcaaa     720
tgttgtgtcg agtgcccacc gtgcccagca ccacctgtgg caggaccgtc agtcttcctc     780
ttccccccaa aacccaagga caccctcatg atctcccgga cccctgaggt cacgtgcgtg     840
gtggtggacg tgagccacga agaccccgag gtccagttca actggtacgt ggacggcgtg     900
gaggtgcata atgccaagac aaagccacgg gaggagcagt tcaacagcac gttccgtgtg     960
gtcagcgtcc tcaccgttgt gcaccaggac tggctgaacg gcaaggagta caagtgcaag    1020
gtctccaaca aaggcctccc agcccccatc gagaaaacca tctccaaaac caaagggcag    1080
ccccgagaac acaggtgta ccctgccc ccatcccggg aggagatgac caagaaccag       1140
gtcagcctga cctgcctggt caaaggcttc taccccagcg acatcgccgt ggagtgggag    1200
agcaatgggc agccggagaa caactacaag accacgcctc ccatgctgga ctccgacggc    1260
tccttcttcc tctacagcaa gctcaccgtg gacaagagca ggtggcagca ggggaacgtc    1320
ttctcatgct ccgtgatgca tgaggctctg cacaaccact acacgcagaa gagcctctcc    1380
ctgtctccgg gtaaatgact cgag                                           1404
```

<210> SEQ ID NO 68
<211> LENGTH: 240
<212> TYPE: PRT
<213> ORGANISM: Artificial Sequence
<220> FEATURE:
<223> OTHER INFORMATION: Synthetic (polypeptide consisting of light chain of huAbF46-H4-A1(H36Y) and human kappa constant region)

<400> SEQUENCE: 68

```
Met Asp Ser Gln Ala Gln Val Leu Met Leu Leu Leu Leu Ser Val Ser
  1               5                  10                  15

Gly Thr Cys Gly Asp Ile Gln Met Thr Gln Ser Pro Ser Ser Leu Ser
             20                  25                  30
```

Ala Ser Val Gly Asp Arg Val Thr Ile Thr Cys Lys Ser Gln Ser
         35                  40                  45

Leu Leu Ala Ser Gly Asn Gln Asn Asn Tyr Leu Ala Trp Tyr Gln Gln
 50                  55                  60

Lys Pro Gly Lys Ala Pro Lys Met Leu Ile Ile Trp Ala Ser Thr Arg
 65                  70                  75                  80

Val Ser Gly Val Pro Ser Arg Phe Ser Gly Ser Gly Ser Gly Thr Asp
                 85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
210                 215                 220

Gln Gly Leu Ser Ser Pro Val Thr Lys Ser Phe Asn Arg Gly Glu Cys
225                 230                 235                 240

<210> SEQ ID NO 69
<211> LENGTH: 758
<212> TYPE: DNA
<213> ORGANISM: Artificial Sequence
<220> FEATURE:
<223> OTHER INFORMATION: Synthetic (polynucleotide encoding polypeptide
      consisting of light chain of huAbF46-H4-A1(H36Y) and human kappa
      constant region)

<400> SEQUENCE: 69
aattcactag tgattaattc gccgccacca tggattcaca ggcccaggtc ctcatgttgc      60
tgctgctatc ggtatctggt acctgtggag atatccagat gacccagtcc ccgagctccc     120
tgtccgcctc tgtgggcgat agggtcacca tcacctgcaa gtccagtcag agtcttttag     180
ctagtggcaa ccaaaataac tacttggcct ggtaccaaca gaaaccagga aaagctccga     240
aaatgctgat tatttgggca tccactaggg tatctggagt cccttctcgc ttctctggat     300
ccgggtctgg gacggatttc actctgacca tcagcagtct gcagccggaa gacttcgcaa     360
cttattactg tcagcagtcc tacagccgcc cgtacacgtt cggacagggt accaaggtgg     420
agatcaaacg tacggtggct gcaccatctg tcttcatctt cccgccatct gatgagcagt     480
tgaaatctgg aactgcctct gttgtgtgcc tgctgaataa cttctatccc agagaggcca     540
aagtacagtg gaaggtggat aacgccctcc aatcgggtaa ctcccaggag agtgtcacag     600
agcaggacag caaggacagc acctacagcc tcagcagcac cctgacgctg agcaaagcag     660
actacgagaa acacaaagtc tacgcctgcg aagtcaccca tcagggcctg agctcgcccg     720
tcacaaagag cttcaacagg ggagagtgtt gactcgag                            758

<210> SEQ ID NO 70

```
<211> LENGTH: 240
<212> TYPE: PRT
<213> ORGANISM: Artificial Sequence
<220> FEATURE:
<223> OTHER INFORMATION: Synthetic (polypeptide consisting of light
      chain of huAbF46-H4-A1 and human kappa constant region)

<400> SEQUENCE: 70

Met Asp Ser Gln Ala Gln Val Leu Met Leu Leu Leu Ser Val Ser
1               5                   10                  15

Gly Thr Cys Gly Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
        35                  40                  45

Leu Leu Ala Ser Gly Asn Gln Asn Asn Tyr Leu Ala Trp His Gln Gln
    50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 71
<211> LENGTH: 19
<212> TYPE: PRT
<213> ORGANISM: Artificial Sequence
<220> FEATURE:
<223> OTHER INFORMATION: Synthetic (epitope in SEMA domain of c-Met)

<400> SEQUENCE: 71

Phe Ser Pro Gln Ile Glu Glu Pro Ser Gln Cys Pro Asp Cys Val Val
1               5                   10                  15

Ser Ala Leu

<210> SEQ ID NO 72
<211> LENGTH: 10
<212> TYPE: PRT
<213> ORGANISM: Artificial Sequence
<220> FEATURE:
<223> OTHER INFORMATION: Synthetic (epitope in SEMA domain of c-Met)

<400> SEQUENCE: 72
```

Pro Gln Ile Glu Glu Pro Ser Gln Cys Pro
1               5                   10

<210> SEQ ID NO 73
<211> LENGTH: 5
<212> TYPE: PRT
<213> ORGANISM: Artificial Sequence
<220> FEATURE:
<223> OTHER INFORMATION: Synthetic (epitope in SEMA domain of c-Met)

<400> SEQUENCE: 73

Glu Glu Pro Ser Gln
1               5

<210> SEQ ID NO 74
<211> LENGTH: 117
<212> TYPE: PRT
<213> ORGANISM: Artificial Sequence
<220> FEATURE:
<223> OTHER INFORMATION: Synthetic (heavy chain variable region of
      anti-c-Met antibody (AbF46 or huAbF46-H1))

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 75
<211> LENGTH: 114
<212> TYPE: PRT
<213> ORGANISM: Artificial Sequence
<220> FEATURE:
<223> OTHER INFORMATION: Synthetic (light chain variable region of
      anti-c-Met antibody (AbF46 or huAbF46-H1))

<400> SEQUENCE: 75

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

```
Ser Tyr Ser Ala Pro Leu Thr Phe Gly Gly Gly Thr Lys Val Glu Ile
            100                 105                 110

Lys Arg

<210> SEQ ID NO 76
<211> LENGTH: 1416
<212> TYPE: DNA
<213> ORGANISM: Artificial Sequence
<220> FEATURE:
<223> OTHER INFORMATION: Synthetic (nucleotide sequence of heavy chain
      of anti-c-Met antibody (AbF46 or huAbF46-H1))
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop sodon
<220> FEATURE:
<221> NAME/KEY: misc_feature
<222> LOCATION: (1411)..(1416)
<223> OTHER INFORMATION: XhoI restriction site

<400> SEQUENCE: 76
gaattcgccg ccaccatgga atggagctgg gttttctcg taacactttt aaatggtatc      60
cagtgtgagg tgaagctggt ggagtctgga ggaggcttgg tacagcctgg gggttctctg     120
agactctcct gtgcaacttc tgggttcacc ttcactgatt actacatgag ctgggtccgc     180
cagcctccag gaaaggcact tgagtggttg gtttttatta gaaacaaagc taatggttac     240
acaacagagt acagtgcatc tgtgaagggt cggttcacca tctccagaga taattcccaa     300
agcatcctct atcttcaaat ggacaccctg agagctgagg acagtgccac ttattactgt     360
gcaagagata ctggtttgc ttactggggc caagggactc tggtcactgt ctctgcagct     420
agcaccaagg gcccatcggt cttcccctg gcaccctcct ccaagagcac ctctgggggc      480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa     720
tcttgtgaca aaactcacac atgcccaccg tgcccagcac ctgaactcct ggggggaccg     780
tcagtcttcc tcttccccc aaaacccaag gacaccctca tgatctcccg gacccctgag     840
gtcacatgcg tggtggtgga cgtgagccac gaagaccctg aggtcaagtt caactggtac     900
gtggacggcg tggaggtgca taatgccaag acaaagccgc gggaggagca gtacaacagc     960
acgtaccgtg tggtcagcgt cctcaccgtc ctgcaccagg actggctgaa tggcaaggag    1020
```

-continued

```
tacaagtgca aggtctccaa caaagccctc ccagccccca tcgagaaaac catctccaaa    1080
gccaaagggc agccccgaga accacaggtg tacaccctgc ccccatcccg ggaggagatg    1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga ctcgag                              1416
```

<210> SEQ ID NO 77  
<211> LENGTH: 759  
<212> TYPE: DNA  
<213> ORGANISM: Artificial Sequence  
<220> FEATURE:  
<223> OTHER INFORMATION: Synthetic (nucleotide sequence of light chain of anti-c-Met antibody (AbF46 or huAbF46-H1))  
<220> FEATURE:  
<221> NAME/KEY: misc_difference  
<222> LOCATION: (1)..(6)  
<223> OTHER INFORMATION: EcoRI restriction site  
<220> FEATURE:  
<221> NAME/KEY: misc_difference  
<222> LOCATION: (7)..(90)  
<223> OTHER INFORMATION: signal sequence  
<220> FEATURE:  
<221> NAME/KEY: misc_difference  
<222> LOCATION: (91)..(432)  
<223> OTHER INFORMATION: VL - light chain variable region  
<220> FEATURE:  
<221> NAME/KEY: misc_difference  
<222> LOCATION: (430)..(435)  
<223> OTHER INFORMATION: BsiWI restriction site  
<220> FEATURE:  
<221> NAME/KEY: misc_difference  
<222> LOCATION: (433)..(750)  
<223> OTHER INFORMATION: CL - light chain constant region  
<220> FEATURE:  
<221> NAME/KEY: misc_difference  
<222> LOCATION: (751)..(753)  
<223> OTHER INFORMATION: stop codon  
<220> FEATURE:  
<221> NAME/KEY: misc_difference  
<222> LOCATION: (754)..(759)  
<223> OTHER INFORMATION: XhoI restriction site

<400> SEQUENCE: 77

```
gaattcacta gtgattaatt cgccgccacc atgattcac aggcccaggt cctcatgttg      60
ctgctgctat cggtatctgg tacctgtgga gacattttga tgacccagtc tccatcctcc    120
ctgactgtgt cagcaggaga gaaggtcact atgagctgca gtccagtca gagtctttta     180 gctagtggca accaaaataa ctacttggcc tggcaccagc agaaaccagg acgatctcct    240
aaaatgctga taatttgggc atccactagg gtatctggag tccctgatcg cttcataggc    300
agtggatctg ggacggattt cactctgacc atcaacagtg tgcaggctga agatctggct    360
gtttattact gtcagcagtc ctacagcgct ccgctcacgt tcggtgctgg gaccaagctg    420
gagctgaaac gtacggtggc tgcaccatct gtcttcatct tcccgccatc tgatgagcag    480
ttgaaatctg gaactgcctc tgttgtgtgc ctgctgaata acttctatcc cagagaggcc    540
aaagtacagt ggaaggtgga taacgccctc caatcgggta actcccagga gagtgtcaca    600
gagcaggaca gcaaggacag cacctacagc ctcagcagca cctgacgct gagcaaagca    660 gactacgaga aacacaaagt ctacgcctgc gaagtcaccc atcagggcct gagctcgccc    720
gtcacaaaga gcttcaacag gggagagtgt tgactcgag                           759
```

<210> SEQ ID NO 78
<211> LENGTH: 4170
<212> TYPE: DNA
<213> ORGANISM: Artificial Sequence
<220> FEATURE:
<223> OTHER INFORMATION: Synthetic (polynucleotide encoding c-Met protein)

<400> SEQUENCE: 78

| | | | | | |
|---|---|---|---|---|---|
| atgaaggccc | ccgctgtgct | tgcacctggc | atcctcgtgc | tcctgtttac | cttggtgcag    60 |
| aggagcaatg | gggagtgtaa | agaggcacta | gcaaagtccg | agatgaatgt | gaatatgaag   120 |
| tatcagcttc | ccaacttcac | cgcggaaaca | cccatccaga | atgtcattct | acatgagcat   180 |
| cacattttcc | ttggtgccac | taactacatt | tatgttttaa | atgaggaaga | ccttcagaag   240 |
| gttgctgagt | acaagactgg | gcctgtgctg | aacacccag | attgtttccc | atgtcaggac   300 |
| tgcagcagca | aagccaattt | atcaggaggt | gtttggaaag | ataacatcaa | catggctcta   360 |
| gttgtcgaca | cctactatga | tgatcaactc | attagctgtg | gcagcgtcaa | cagagggacc   420 |
| tgccagcgac | atgtctttcc | ccacaatcat | actgctgaca | tacagtcgga | ggttcactgc   480 |
| atattctccc | cacagataga | agagcccagc | cagtgtcctg | actgtgtggt | gagcgccctg   540 |
| ggagccaaag | tcctttcatc | tgtaaaggac | cggttcatca | acttctttgt | aggcaatacc   600 |
| ataaattctt | cttatttccc | agatcatcca | ttgcattcga | tatcagtgag | aaggctaaag   660 |
| gaaacgaaag | atggttttat | gttttgacg | gaccagtcct | acattgatgt | tttacctgag   720 |
| ttcagagatt | cttaccccat | taagtatgtc | catgcctttg | aaagcaacaa | ttttatttac   780 |
| ttcttgacgg | tccaaaggga | aactctagat | gctcagactt | tcacacaag | aataatcagg   840 |
| ttctgttcca | taaactctgg | attgcattcc | tacatggaaa | tgcctctgga | gtgtattctc   900 |
| acagaaaaga | gaaaaagag | atccacaaag | aaggaagtgt | ttaatatact | tcaggctgcg   960 |
| tatgtcagca | agcctggggc | ccagcttgct | agacaaatag | gagccagcct | gaatgatgac  1020 |
| attcttttcg | gggtgttcgc | acaaagcaag | ccagattctg | ccgaaccaat | ggatcgatct  1080 |
| gccatgtgtg | cattccctat | caaatatgtc | aacgacttct | tcaacaagat | cgtcaacaaa  1140 |
| aacaatgtga | gatgtctcca | gcatttttac | ggacccaatc | atgagcactg | ctttaatagg  1200 |
| acacttctga | gaaattcatc | aggctgtgaa | gcgcgccgtg | atgaatatcg | aacagagttt  1260 |
| accacagctt | tgcagcgcgt | tgacttattc | atgggtcaat | tcagcgaagt | cctcttaaca  1320 |
| tctatatcca | ccttcattaa | aggagacctc | accatagcta | tcttgggac | atcagagggt  1380 |
| cgcttcatgc | aggttgtggt | ttctcgatca | ggaccatcaa | cccctcatgt | gaattttctc  1440 |
| ctggactccc | atccagtgtc | tccagaagtg | attgtggagc | atacattaaa | ccaaaatggc  1500 |
| tacacactgg | ttatcactgg | gaagaagatc | acgaagatcc | cattgaatgg | cttgggctgc  1560 |
| agacatttcc | agtcctgcag | tcaatgcctc | tctgccccac | cctttgttca | gtgtggctgg  1620 |
| tgccacgaca | aatgtgtgcg | atcggaggaa | tgcctgagcg | ggacatggac | tcaacgatc  1680 |
| tgtctgcctg | caatctacaa | ggttttccca | aatagtgcac | cccttgaagg | agggacaagg  1740 |
| ctgaccatat | gtggctggga | ctttggattt | cggaggaata | taaatttga | tttaaagaaa  1800 |
| actagagttc | tccttggaaa | tgagagctgc | accttgactt | taagtgagag | cacgatgaat  1860 |
| acattgaaat | gcacagttgg | tcctgccatg | aataagcatt | tcaatatgtc | cataattatt  1920 |
| tcaaatggcc | acgggacaac | acaatacagt | acattctcct | atgtggatcc | tgtaataaca  1980 |
| agtatttcgc | cgaaatacgg | tcctatggct | ggtggcactt | tacttacttt | aactggaaat  2040 |

```
tacctaaaca gtgggaattc tagacacatt tcaattggtg gaaaaacatg tactttaaaa    2100
agtgtgtcaa acagtattct tgaatgttat accccagccc aaaccatttc aactgagttt    2160
gctgttaaat tgaaaattga cttagccaac cgagagacaa gcatcttcag ttaccgtgaa    2220
gatcccattg tctatgaaat tcatccaacc aaatctttta ttagtggtgg agcacaata     2280 acaggtgttg ggaaaaacct gaattcagtt agtgtcccga gaatggtcat aaatgtgcat    2340
gaagcaggaa ggaactttac agtggcatgt caacatcgct ctaattcaga gataatctgt    2400
tgtaccactc cttccctgca acagctgaat ctgcaactcc ccctgaaaac caaagccttt    2460
ttcatgttag atgggatcct ttccaaatac tttgatctca tttatgtaca taatcctgtg    2520
tttaagcctt ttgaaaagcc agtgatgatc tcaatgggca atgaaaatgt actggaaatt    2580
aagggaaatg atattgaccc tgaagcagtt aaaggtgaag tgttaaaagt tggaaataag    2640
agctgtgaga atatacactt acattctgaa gccgttttat gcacggtccc caatgacctg    2700
ctgaaattga acagcgagct aaatatagag tggaagcaag caatttcttc aaccgtcctt    2760
ggaaaagtaa tagttcaacc agatcagaat ttcacaggat tgattgctgg tgttgtctca    2820
atatcaacag cactgttatt actacttggg ttttcctgt ggctgaaaaa gagaaagcaa     2880
attaaagatc tgggcagtga attagttcgc tacgatgcaa gagtacacac tcctcatttg    2940
gataggcttg taagtgcccg aagtgtaagc ccaactacag aaatggtttc aaatgaatct    3000
gtagactacc gagctacttt tccagaagat cagtttccta attcatctca gaacggttca    3060
tgccgacaag tgcagtatcc tctgacagac atgtccccca tcctaactag tggggactct    3120
gatatatcca gtccattact gcaaaatact gtccacattg acctcagtgc tctaaatcca    3180
gagctggtcc aggcagtgca gcatgtagtg attgggccca gtagcctgat tgtgcatttc    3240
aatgaagtca taggaagagg gcattttggt tgtgtatatc atgggacttt gttggacaat    3300
gatggcaaga aaattcactg tgctgtgaaa tccttgaaca gaatcactga cataggagaa    3360
gtttcccaat ttctgaccga gggaatcatc atgaaagatt ttagtcatcc caatgtcctc    3420
tcgctcctgg gaatctgcct gcgaagtgaa gggtctccgc tggtggtcct accatacatg    3480
aaacatggag atcttcgaaa tttcattcga aatgagactc ataatccaac tgtaaaagat    3540
cttattggct ttggtcttca gtagccaaa ggcatgaaat atcttgcaag caaaaagttt     3600
gtccacagag acttggctgc aagaaactgt atgctggatg aaaaattcac agtcaaggtt    3660
gctgattttg gtcttgccag agacatgtat gataaagaat actatagtgt acacaacaaa    3720
acaggtgcaa agctgccagt gaagtggatg gctttggaaa gtctgcaaac tcaaaagttt    3780
accaccaagt cagatgtgtg gtcctttggc gtgctcctct gggagctgat gacaagagga    3840
gccccacctt atcctgacgt aaacaccttt gatataactg tttacttgtt gcaagggaga    3900
agactcctac aacccgaata ctgcccagac cccttatatg aagtaatgct aaaatgctgg    3960
caccctaaag ccgaaatgcg cccatccttt tctgaactgg tgtcccggat atcagcgatc    4020
ttctctactt tcattgggga gcactatgtc catgtgaacg ctacttatgt gaacgtaaaa    4080
tgtgtcgctc cgtatccttc tctgttgtca tcagaagata cgctgatga tgaggtggac     4140 acacgaccag cctccttctg ggagacatca                                     4170
```

<210> SEQ ID NO 79
<211> LENGTH: 444
<212> TYPE: PRT
<213> ORGANISM: Artificial Sequence
<220> FEATURE:
<223> OTHER INFORMATION: Synthetic (SEMA domain of c-Met)

<400> SEQUENCE: 79

Leu His Glu His His Ile Phe Leu Gly Ala Thr Asn Tyr Ile Tyr Val
1               5                   10                  15

Leu Asn Glu Glu Asp Leu Gln Lys Val Ala Glu Tyr Lys Thr Gly Pro
            20                  25                  30

Val Leu Glu His Pro Asp Cys Phe Pro Cys Gln Asp Cys Ser Ser Lys
        35                  40                  45

Ala Asn Leu Ser Gly Gly Val Trp Lys Asp Asn Ile Asn Met Ala Leu
    50                  55                  60

Val Val Asp Thr Tyr Tyr Asp Asp Gln Leu Ile Ser Cys Gly Ser Val
65              70                  75                  80

Asn Arg Gly Thr Cys Gln Arg His Val Phe Pro His Asn His Thr Ala
            85                  90                  95

Asp Ile Gln Ser Glu Val His Cys Ile Phe Ser Pro Gln Ile Glu Glu
            100                 105                 110

Pro Ser Gln Cys Pro Asp Cys Val Val Ser Ala Leu Gly Ala Lys Val
        115                 120                 125

Leu Ser Ser Val Lys Asp Arg Phe Ile Asn Phe Phe Val Gly Asn Thr
    130                 135                 140

Ile Asn Ser Ser Tyr Phe Pro Asp His Pro Leu His Ser Ile Ser Val
145             150                 155                 160

Arg Arg Leu Lys Glu Thr Lys Asp Gly Phe Met Phe Leu Thr Asp Gln
            165                 170                 175

Ser Tyr Ile Asp Val Leu Pro Glu Phe Arg Asp Ser Tyr Pro Ile Lys
        180                 185                 190

Tyr Val His Ala Phe Glu Ser Asn Asn Phe Ile Tyr Phe Leu Thr Val
    195                 200                 205

Gln Arg Glu Thr Leu Asp Ala Gln Thr Phe His Thr Arg Ile Ile Arg
210             215                 220

Phe Cys Ser Ile Asn Ser Gly Leu His Ser Tyr Met Glu Met Pro Leu
225             230                 235                 240

Glu Cys Ile Leu Thr Glu Lys Arg Lys Lys Arg Ser Thr Lys Lys Glu
            245                 250                 255

Val Phe Asn Ile Leu Gln Ala Ala Tyr Val Ser Lys Pro Gly Ala Gln
        260                 265                 270

Leu Ala Arg Gln Ile Gly Ala Ser Leu Asn Asp Asp Ile Leu Phe Gly
    275                 280                 285

Val Phe Ala Gln Ser Lys Pro Asp Ser Ala Glu Pro Met Asp Arg Ser
    290                 295                 300

Ala Met Cys Ala Phe Pro Ile Lys Tyr Val Asn Asp Phe Phe Asn Lys
305             310                 315                 320

Ile Val Asn Lys Asn Asn Val Arg Cys Leu Gln His Phe Tyr Gly Pro
            325                 330                 335

Asn His Glu His Cys Phe Asn Thr Leu Leu Arg Asn Ser Ser Gly
            340                 345                 350

Cys Glu Ala Arg Arg Asp Glu Tyr Arg Thr Glu Phe Thr Thr Ala Leu
        355                 360                 365

Gln Arg Val Asp Leu Phe Met Gly Gln Phe Ser Glu Val Leu Leu Thr
    370                 375                 380

Ser Ile Ser Thr Phe Ile Lys Gly Asp Leu Thr Ile Ala Asn Leu Gly
385             390                 395                 400

Thr Ser Glu Gly Arg Phe Met Gln Val Val Val Ser Arg Ser Gly Pro

-continued

```
                405                 410                 415

Ser Thr Pro His Val Asn Phe Leu Leu Asp Ser His Pro Val Ser Pro
            420                 425                 430

Glu Val Ile Val Glu His Thr Leu Asn Gln Asn Gly
        435                 440

<210> SEQ ID NO 80
<211> LENGTH: 451
<212> TYPE: PRT
<213> ORGANISM: Artificial Sequence
<220> FEATURE:
<223> OTHER INFORMATION: Synthetic (Synthrt)

<400> SEQUENCE: 80

Tyr Thr Leu Val Ile Thr Gly Lys Lys Ile Thr Lys Ile Pro Leu Asn
1               5                   10                  15

Gly Leu Gly Cys Arg His Phe Gln Ser Cys Ser Gln Cys Leu Ser Ala
            20                  25                  30

Pro Pro Phe Val Gln Cys Gly Trp Cys His Asp Lys Cys Val Arg Ser
        35                  40                  45

Glu Glu Cys Leu Ser Gly Thr Trp Thr Gln Gln Ile Cys Leu Pro Ala
    50                  55                  60

Ile Tyr Lys Val Phe Pro Asn Ser Ala Pro Leu Glu Gly Gly Thr Arg
65                  70                  75                  80

Leu Thr Ile Cys Gly Trp Asp Phe Gly Phe Arg Arg Asn Asn Lys Phe
                85                  90                  95

Asp Leu Lys Lys Thr Arg Val Leu Leu Gly Asn Glu Ser Cys Thr Leu
            100                 105                 110

Thr Leu Ser Glu Ser Thr Met Asn Thr Leu Lys Cys Thr Val Gly Pro
        115                 120                 125

Ala Met Asn Lys His Phe Asn Met Ser Ile Ile Ser Asn Gly His
    130                 135                 140

Gly Thr Thr Gln Tyr Ser Thr Phe Ser Tyr Val Asp Pro Val Ile Thr
145                 150                 155                 160

Ser Ile Ser Pro Lys Tyr Gly Pro Met Ala Gly Gly Thr Leu Leu Thr
                165                 170                 175

Leu Thr Gly Asn Tyr Leu Asn Ser Gly Asn Ser Arg His Ile Ser Ile
            180                 185                 190

Gly Gly Lys Thr Cys Thr Leu Lys Ser Val Ser Asn Ser Ile Leu Glu
        195                 200                 205

Cys Tyr Thr Pro Ala Gln Thr Ile Ser Thr Glu Phe Ala Val Lys Leu
    210                 215                 220

Lys Ile Asp Leu Ala Asn Arg Glu Thr Ser Ile Phe Ser Tyr Arg Glu
225                 230                 235                 240

Asp Pro Ile Val Tyr Glu Ile His Pro Thr Lys Ser Phe Ile Ser Thr
                245                 250                 255

Trp Trp Lys Glu Pro Leu Asn Ile Val Ser Phe Leu Phe Cys Phe Ala
            260                 265                 270

Ser Gly Gly Ser Thr Ile Thr Gly Val Gly Lys Asn Leu Asn Ser Val
        275                 280                 285

Ser Val Pro Arg Met Val Ile Asn Val His Glu Ala Gly Arg Asn Phe
    290                 295                 300

Thr Val Ala Cys Gln His Arg Ser Asn Ser Glu Ile Ile Cys Cys Thr
305                 310                 315                 320

Thr Pro Ser Leu Gln Gln Leu Asn Leu Gln Leu Pro Leu Lys Thr Lys
```

```
                  325                 330                 335
Ala Phe Phe Met Leu Asp Gly Ile Leu Ser Lys Tyr Phe Asp Leu Ile
                340                 345                 350

Tyr Val His Asn Pro Val Phe Lys Pro Phe Glu Lys Pro Val Met Ile
                355                 360                 365

Ser Met Gly Asn Glu Asn Val Leu Glu Ile Lys Gly Asn Asp Ile Asp
                370                 375                 380

Pro Glu Ala Val Lys Gly Glu Val Leu Lys Val Gly Asn Lys Ser Cys
385                 390                 395                 400

Glu Asn Ile His Leu His Ser Glu Ala Val Leu Cys Thr Val Pro Asn
                405                 410                 415

Asp Leu Leu Lys Leu Asn Ser Glu Leu Asn Ile Glu Trp Lys Gln Ala
                420                 425                 430

Ile Ser Ser Thr Val Leu Gly Lys Val Ile Val Gln Pro Asp Gln Asn
                435                 440                 445

Phe Thr Gly
        450

<210> SEQ ID NO 81
<211> LENGTH: 313
<212> TYPE: PRT
<213> ORGANISM: Artificial Sequence
<220> FEATURE:
<223> OTHER INFORMATION: Synthetic (TyrKc domain of c-Met)

<400> SEQUENCE: 81

Val His Phe Asn Glu Val Ile Gly Arg Gly His Phe Gly Cys Val Tyr
1               5                   10                  15

His Gly Thr Leu Leu Asp Asn Asp Gly Lys Lys Ile His Cys Ala Val
                20                  25                  30

Lys Ser Leu Asn Arg Ile Thr Asp Ile Gly Glu Val Ser Gln Phe Leu
            35                  40                  45

Thr Glu Gly Ile Ile Met Lys Asp Phe Ser His Pro Asn Val Leu Ser
        50                  55                  60

Leu Leu Gly Ile Cys Leu Arg Ser Glu Gly Ser Pro Leu Val Val Leu
65                  70                  75                  80

Pro Tyr Met Lys His Gly Asp Leu Arg Asn Phe Ile Arg Asn Glu Thr
                85                  90                  95

His Asn Pro Thr Val Lys Asp Leu Ile Gly Phe Gly Leu Gln Val Ala
                100                 105                 110

Lys Gly Met Lys Tyr Leu Ala Ser Lys Lys Phe Val His Arg Asp Leu
            115                 120                 125

Ala Ala Arg Asn Cys Met Leu Asp Glu Lys Phe Thr Val Lys Val Ala
        130                 135                 140

Asp Phe Gly Leu Ala Arg Asp Met Tyr Asp Lys Glu Tyr Tyr Ser Val
145                 150                 155                 160

His Asn Lys Thr Gly Ala Lys Leu Pro Val Lys Trp Met Ala Leu Glu
                165                 170                 175

Ser Leu Gln Thr Gln Lys Phe Thr Thr Lys Ser Asp Val Trp Ser Phe
                180                 185                 190

Gly Val Leu Leu Trp Glu Leu Met Thr Arg Gly Ala Pro Pro Tyr Pro
            195                 200                 205

Asp Val Asn Thr Phe Asp Ile Thr Val Tyr Leu Leu Gln Gly Arg Arg
        210                 215                 220

Leu Leu Gln Pro Glu Tyr Cys Pro Asp Pro Leu Tyr Glu Val Met Leu
```

```
                225                 230                 235                 240
Lys Cys Trp His Pro Lys Ala Glu Met Arg Pro Ser Phe Ser Glu Leu
                245                 250                 255

Val Ser Arg Ile Ser Ala Ile Phe Ser Thr Phe Ile Gly Glu His Tyr
                260                 265                 270

Val His Val Asn Ala Thr Tyr Val Asn Val Lys Cys Val Ala Pro Tyr
                275                 280                 285

Pro Ser Leu Leu Ser Ser Glu Asp Asn Ala Asp Asp Glu Val Asp Thr
                290                 295                 300

Arg Pro Ala Ser Phe Trp Glu Thr Ser
305                 310

<210> SEQ ID NO 82
<211> LENGTH: 1332
<212> TYPE: DNA
<213> ORGANISM: Artificial Sequence
<220> FEATURE:
<223> OTHER INFORMATION: Synthetic (polynucleotide encoding SEMA domain
      of c-Met)

<400> SEQUENCE: 82
ctacatgagc atcacatttt ccttggtgcc actaactaca tttatgtttt aaatgaggaa      60
gaccttcaga aggttgctga gtacaagact gggcctgtgc tggaacaccc agattgtttc     120
ccatgtcagg actgcagcag caaagccaat ttatcaggag tgtttggaa agataacatc      180 aacatggctc tagttgtcga cacctactat gatgatcaac tcattagctg tggcagcgtc     240
aacagaggga cctgccagcg acatgtcttt ccccacaatc atactgctga catacagtcg     300
gaggttcact gcatattctc cccacagata aagagcccca gccagtgtcc tgactgtgtg     360
gtgagcgccc tgggagccaa agtccttca tctgtaaagg accggttcat caacttcttt     420
gtaggcaata ccataaattc ttcttatttc ccagatcatc cattgcattc gatatcagtg     480
agaaggctaa aggaaacgaa agatggtttt atgtttttga cggaccagtc ctacattgat     540
gttttacctg agttcagaga ttcttacccc attaagtatg tccatgcctt tgaaagcaac      600 aatttttattt acttcttgac ggtccaaagg gaaactctag atgctcagac ttttcacaca     660
agaataatca ggttctgttc cataaactct ggattgcatt cctacatgga aatgcctctg      720
gagtgtattc tcacagaaaa gagaaaaaag agatccacaa agaaggaagt gtttaatata     780
cttcaggctg cgtatgtcag caagcctggg gcccagcttg ctagacaaat aggagccagc     840
ctgaatgatg acattctttt cggggtgttc gcacaaagca agccagattc tgccgaacca     900
atggatcgat ctgccatgtg tgcattccct atcaaatatg tcaacgactt cttcaacaag      960
atcgtcaaca aaaacaatgt gagatgtctc cagcattttt acggacccaa tcatgagcac     1020
tgctttaata ggacacttct gagaaattca tcaggctgtg aagcgcgccg tgatgaatat     1080
cgaacagagt ttaccacagc tttgcagcgc gttgacttat tcatgggtca attcagcgaa     1140
gtcctcttaa catctatatc caccttcatt aaaggagacc tcaccatagc taatcttggg     1200
acatcagagg gtcgcttcat gcaggttgtg gtttctcgat caggaccatc aaccctcat      1260 gtgaattttc tcctggactc ccatccagtg tctccagaag tgattgtgga gcatacatta     1320
aaccaaaatg gc                                                         1332

<210> SEQ ID NO 83
<211> LENGTH: 1299
<212> TYPE: DNA
<213> ORGANISM: Artificial Sequence
```

```
<220> FEATURE:
<223> OTHER INFORMATION: Synthetic (polynucleotide encoding PSI-IPT
      domain of c-Met)

<400> SEQUENCE: 83
tacacactgg ttatcactgg gaagaagatc acgaagatcc cattgaatgg cttgggctgc     60
agacatttcc agtcctgcag tcaatgcctc tctgccccac cctttgttca gtgtggctgg    120
tgccacgaca aatgtgtgcg atcggaggaa tgcctgagcg ggacatggac tcaacagatc    180
tgtctgcctg caatctacaa ggttttccca aatagtgcac cccttgaagg agggacaagg    240
ctgaccatat gtggctggga ctttggattt cggaggaata taaatttga tttaaagaaa     300 actagagttc tccttggaaa tgagagctgc accttgactt taagtgagag cacgatgaat    360
acattgaaat gcacagttgg tcctgccatg aataagcatt tcaatatgtc cataattatt    420
tcaaatggcc acgggacaac acaatacagt acattctcct atgtggatcc tgtaataaca    480
agtatttcgc cgaaatacgg tcctatggct ggtggcactt tacttacttt aactggaaat    540
tacctaaaca gtgggaattc tagacacatt tcaattggtg aaaaacatg tactttaaaa     600 agtgtgtcaa acagtattct tgaatgttat accccagccc aaaccatttc aactgagttt    660
gctgttaaat tgaaaattga cttagccaac cgagagacaa gcatcttcag ttaccgtgaa    720
gatcccattg tctatgaaat tcatccaacc aaatctttta ttagtggtgg gagcacaata    780
acaggtgttg ggaaaaacct gaattcagtt agtgtcccga gaatggtcat aaatgtgcat    840
gaagcaggaa ggaactttac agtggcatgt caacatcgct ctaattcaga gataatctgt    900
tgtaccactc cttccctgca acagctgaat ctgcaactcc ccctgaaaac caagcctt    960 ttcatgttag atgggatcct ttccaaatac tttgatctca tttatgtaca taatcctgtg   1020
tttaagcctt ttgaaaagcc agtgatgatc tcaatgggca atgaaaatgt actggaaatt   1080
aagggaaatg atattgaccc tgaagcagtt aaaggtgaag tgttaaaagt tggaaataag   1140
agctgtgaga atatacactt acattctgaa gccgttttat gcacggtccc caatgacctg   1200
ctgaaattga acagcgagct aaatatagag tggaagcaag caatttcttc aacgtccctt   1260
ggaaaagtaa tagttcaacc agatcagaat ttcacagga                          1299

<210> SEQ ID NO 84
<211> LENGTH: 939
<212> TYPE: DNA
<213> ORGANISM: Artificial Sequence
<220> FEATURE:
<223> OTHER INFORMATION: Synthetic (polynucleotide encoding TyrKc domain
      of c-Met)

<400> SEQUENCE: 84
gtgcatttca atgaagtcat aggaagaggg cattttggtt gtgtatatca tgggactttg     60
ttggacaatg atggcaagaa aattcactgt gctgtgaaat ccttgaacag aatcactgac    120
ataggagaag tttcccaatt tctgaccgag ggaatcatca tgaaagattt tagtcatccc    180
aatgtcctct cgctcctggg aatctgcctg cgaagtgaag ggtctccgct ggtggtccta    240
ccatacatga acatggagag tcttcgaaat ttcattcgaa atgagactca taatccaact    300
gtaaaagatc ttattggctt tggtcttcaa gtagccaaag catgaaata tcttgcaagc    360 aaaaagtttg tccacagaga cttggctgca agaaactgta tgctggatga aaaattcaca    420
gtcaaggttg ctgattttgg tcttgccaga gacatgtatg ataaagaata ctatagtgta    480
cacaacaaaa caggtgcaaa gctgccagtg aagtggatgg ctttggaaag tctgcaaact    540
```

```
caaaagttta ccaccaagtc agatgtgtgg tcctttggcg tgctcctctg ggagctgatg      600
acaagaggag ccccacctta tcctgacgta aacacctttg atataactgt ttacttgttg      660
caagggagaa gactcctaca acccgaatac tgcccagacc ccttatatga agtaatgcta      720
aaatgctggc accctaaagc cgaaatgcgc ccatccttt  ctgaactggt gtcccggata       780
tcagcgatct tctctacttt cattggggag cactatgtcc atgtgaacgc tacttatgtg      840
aacgtaaaat gtgtcgctcc gtatccttct ctgttgtcat cagaagataa cgctgatgat      900
gaggtggaca cacgaccagc ctccttctgg gagacatca                              939
```

<210> SEQ ID NO 85
<211> LENGTH: 13
<212> TYPE: PRT
<213> ORGANISM: Artificial Sequence
<220> FEATURE:
<223> OTHER INFORMATION: Synthetic (heavy chain CDR3 of anti-c-Met antibody)

<400> SEQUENCE: 85

Asp Asn Trp Phe Ala Tyr Trp Gly Gln Gly Thr Leu Val
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Synthetic (light chain CDR3 of anti-c-Met antibody)

<400> SEQUENCE: 86

Leu Thr Phe Gly Ala Gly Thr Lys Leu Glu
1               5                   10

<210> SEQ ID NO 87
<211> LENGTH: 117
<212> TYPE: PRT
<213> ORGANISM: Artificial Sequence
<220> FEATURE:
<223> OTHER INFORMATION: Synthetic (heavy chain variable region of monoclonal antibody AbF46)

<400> SEQUENCE: 87

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asp Thr Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ala
        115

<210> SEQ ID NO 88

```
<211> LENGTH: 114
<212> TYPE: PRT
<213> ORGANISM: Artificial Sequence
<220> FEATURE:
<223> OTHER INFORMATION: Synthetic (light chain variable region of
      anti-c-Met antibody)

<400> SEQUENCE: 88

Asp Ile Leu Met Thr Gln Ser Pro Ser Ser Leu Thr Val Ser Ala Gly
1               5                   10                  15

Glu Lys Val Thr Met Ser Cys Lys Ser Ser Gln Ser Leu Leu Ala Ser
            20                  25                  30

Gly Asn Gln Asn Asn Tyr Leu Ala Trp His Gln Gln Lys Pro Gly Arg
        35                  40                  45

Ser Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Asn Ser Val Gln Ala Glu Asp Leu Ala Val Tyr Tyr Cys Gln Gln
                85                  90                  95

Ser Tyr Ser Ala Pro Leu Thr Phe Gly Ala Gly Thr Lys Leu Glu Leu
            100                 105                 110

Lys Arg

<210> SEQ ID NO 89
<211> LENGTH: 17
<212> TYPE: PRT
<213> ORGANISM: Artificial Sequence
<220> FEATURE:
<223> OTHER INFORMATION: Synthetic (light chain CDR3 of anti-c-Met
      antibody)

<400> SEQUENCE: 89

Gln Gln Ser Tyr Ser Ala Pro Leu Thr Phe Gly Ala Gly Thr Lys Leu
1               5                   10                  15

Glu

<210> SEQ ID NO 90
<211> LENGTH: 117
<212> TYPE: PRT
<213> ORGANISM: Artificial Sequence
<220> FEATURE:
<223> OTHER INFORMATION: Synthetic (heavy chain variable region of
      AT-VH1)

<400> SEQUENCE: 90

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110
```

Val Thr Val Ser Ser
        115

<210> SEQ ID NO 91
<211> LENGTH: 117
<212> TYPE: PRT
<213> ORGANISM: Artificial Sequence
<220> FEATURE:
<223> OTHER INFORMATION: Synthetic (heavy chain variable region of
      AT-VH2)

<400> SEQUENCE: 91

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 92
<211> LENGTH: 117
<212> TYPE: PRT
<213> ORGANISM: Artificial Sequence
<220> FEATURE:
<223> OTHER INFORMATION: Synthetic (heavy chain variable region of
      AT-VH3)

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 93
<211> LENGTH: 117
<212> TYPE: PRT
<213> ORGANISM: Artificial Sequence

```
<220> FEATURE:
<223> OTHER INFORMATION: Synthetic (heavy chain variable region of
      AT-VH4)

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gly Thr Leu
            100                 105                 110

Val Thr Val Ser Ser
        115

<210> SEQ ID NO 94
<211> LENGTH: 117
<212> TYPE: PRT
<213> ORGANISM: Artificial Sequence
<220> FEATURE:
<223> OTHER INFORMATION: Synthetic (heavy chain variable region of
      AT-VH5)

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 95
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

<400> SEQUENCE: 95

Asp Ile Gln Met Thr Gln Ser Pro Ser Ser Leu Ser Ala Ser Val Gly
1               5                   10                  15
```

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Lys Pro Gly Lys
        35                  40                  45

Ala Pro Lys Met Leu Ile Ile Trp Ala Ser Thr Arg Val Ser Gly Val
50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg

<210> SEQ ID NO 96
<211> LENGTH: 113
<212> TYPE: PRT
<213> ORGANISM: Artificial Sequence
<220> FEATURE:
<223> OTHER INFORMATION: Synthetic (light chain variable region of
      AT-Vk1)

<400> SEQUENCE: 96

Asp Ile Leu Met Thr Gln Ser Pro Ser Ser Leu Thr Ala Ser Val Gly
1               5                   10                  15

Asp Arg Val Thr Met Thr Cys Lys Ser Ser Gln Ser Leu Leu Ala Ser
            20                  25                  30

Gly Asn Gln Asn Asn Tyr Leu Ala Trp His Gln Lys Pro Gly Lys
        35                  40                  45

Ala Pro Lys Met Leu Ile Ile Trp Ala Ser Thr Arg Val Ser Gly Val
50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 97
<211> LENGTH: 113
<212> TYPE: PRT
<213> ORGANISM: Artificial Sequence
<220> FEATURE:
<223> OTHER INFORMATION: Synthetic (light chain variable region of
      AT-Vk2)

<400> SEQUENCE: 97

Asp Ile Leu Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Lys Pro Gly Lys
        35                  40                  45

Ala Pro Lys Met Leu Ile Ile Trp Ala Ser Thr Arg Val Ser Gly Val
50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 98
<211> LENGTH: 113
<212> TYPE: PRT
<213> ORGANISM: Artificial Sequence
<220> FEATURE:
<223> OTHER INFORMATION: Synthetic (light chain variable region of
      AT-Vk3)

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 99
<211> LENGTH: 113
<212> TYPE: PRT
<213> ORGANISM: Artificial Sequence
<220> FEATURE:
<223> OTHER INFORMATION: Synthetic (light chain variable region of
      AT-Vk4)

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 100

```
<211> LENGTH: 13
<212> TYPE: PRT
<213> ORGANISM: Artificial Sequence
<220> FEATURE:
<223> OTHER INFORMATION: Synthetic (modified hinge region(U7-HC6))

<400> SEQUENCE: 100

Glu Pro Ser Cys Asp Lys His Cys Cys Pro Pro Cys Pro
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Synthetic (modified hinge region(U6-HC7))

<400> SEQUENCE: 101

Glu Pro Lys Ser Cys Asp Cys His Cys Pro Pro Cys Pro
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Synthetic (modified hinge region(U3-HC9))

<400> SEQUENCE: 102

Glu Arg Lys Cys Cys Val Glu Cys Pro Pro Cys Pro
1               5                   10

<210> SEQ ID NO 103
<211> LENGTH: 14
<212> TYPE: PRT
<213> ORGANISM: Artificial Sequence
<220> FEATURE:
<223> OTHER INFORMATION: Synthetic (modified hinge region(U6-HC8))

<400> SEQUENCE: 103

Glu Pro Arg Asp Cys Gly Cys Lys Pro Cys Pro Pro Cys Pro
1               5                   10

<210> SEQ ID NO 104
<211> LENGTH: 13
<212> TYPE: PRT
<213> ORGANISM: Artificial Sequence
<220> FEATURE:
<223> OTHER INFORMATION: Synthetic (modified hinge region(U8-HC5))

<400> SEQUENCE: 104

Glu Lys Cys Asp Lys Thr His Thr Cys Pro Pro Cys Pro
1               5                   10

<210> SEQ ID NO 105
<211> LENGTH: 15
<212> TYPE: PRT
<213> ORGANISM: Artificial Sequence
<220> FEATURE:
<223> OTHER INFORMATION: Synthetic (human hinge region)

<400> SEQUENCE: 105

Glu Pro Lys Ser Cys Asp Lys Thr His Thr Cys Pro Pro Cys Pro
1               5                   10                  15

<210> SEQ ID NO 106
<211> LENGTH: 17
```

```
<212> TYPE: PRT
<213> ORGANISM: Artificial Sequence
<220> FEATURE:
<223> OTHER INFORMATION: Synthetic (CDR-L1 of antibody L3-11Y)

<400> SEQUENCE: 106

Lys Ser Ser Gln Ser Leu Leu Ala Trp Gly Asn Gln Asn Asn Tyr Leu
1               5                   10                  15

Ala

<210> SEQ ID NO 107
<211> LENGTH: 114
<212> TYPE: PRT
<213> ORGANISM: Artificial Sequence
<220> FEATURE:
<223> OTHER INFORMATION: Synthetic (amino acid sequence of light chain
      variable region of antibody L3-11Y)

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Trp
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg

<210> SEQ ID NO 108
<211> LENGTH: 220
<212> TYPE: PRT
<213> ORGANISM: Artificial Sequence
<220> FEATURE:
<223> OTHER INFORMATION: Synthetic (amino acid sequence of light chain
      of antibody L3-11Y)

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Trp
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
```

```
            115                 120                 125
Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 109
<211> LENGTH: 120
<212> TYPE: PRT
<213> ORGANISM: Artificial Sequence
<220> FEATURE:
<223> OTHER INFORMATION: Synthetic (heavy chain variable region of
      anti-Her2 antibody)

<400> SEQUENCE: 109

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 110
<211> LENGTH: 360
<212> TYPE: DNA
<213> ORGANISM: Artificial Sequence
<220> FEATURE:
<223> OTHER INFORMATION: Synthetic (DNA encoding heavy chain variable
      region of anti-Her2 antibody)

<400> SEQUENCE: 110
gaagttcagc tggtggagtc tggcggtggc ctggtgcagc caggggggctc actccgtttg      60 tcctgtgcag cttctggctt caacattaaa gacacctata tactgggt gcgtcaggcc       120 ccgggtaagg gcctggaatg ggttgcaagg atttatccta cgaatggtta tactagatat     180
gccgatagcg tcaagggccg tttcactata agcgcagaca catccaaaaa cacagcctac    240
ctgcagatga acagcctgcg tgctgaggac actgccgtct attattgttc tagatgggga    300
ggggacggct ctatgctat ggactactgg ggtcaaggaa ccctggtcac cgtctcctcg      360
```

```
<210> SEQ ID NO 111
<211> LENGTH: 108
<212> TYPE: PRT
<213> ORGANISM: Artificial Sequence
<220> FEATURE:
<223> OTHER INFORMATION: Synthetic (light chain variable region of
      anti-Her2 antibody)

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg
            100                 105

<210> SEQ ID NO 112
<211> LENGTH: 324
<212> TYPE: DNA
<213> ORGANISM: Artificial Sequence
<220> FEATURE:
<223> OTHER INFORMATION: Synthetic (DNA encoding light chain variable
      region of anti-Her2 antibody)

<400> SEQUENCE: 112
gatatccaga tgacccagtc cccgagctcc ctgtccgcct ctgtgggcga tagggtcacc      60
atcacctgcc gtgccagtca ggatgtgaat actgctgtag cctggtatca acagaaacca    120
ggaaaagctc cgaaactact gatttactcg gcatccttcc tctactctgg agtcccttct    180
cgcttctctg gttccagatc tgggacggat tcactctga ccatcagcag tctgcagccg      240
gaagacttcg caacttatta ctgtcagcaa cattatacta ctcctcccac gttcggacag    300
ggtaccaagg tggagatcaa acga                                            324

<210> SEQ ID NO 113
<211> LENGTH: 10
<212> TYPE: PRT
<213> ORGANISM: Artificial Sequence
<220> FEATURE:
<223> OTHER INFORMATION: Synthetic (peptide linker)

<400> SEQUENCE: 113

Gly Gly Gly Gly Ser Gly Gly Gly Gly Ser
1               5                   10

<210> SEQ ID NO 114
<211> LENGTH: 114
<212> TYPE: PRT
<213> ORGANISM: Artificial Sequence
<220> FEATURE:
<223> OTHER INFORMATION: Synthetic (light chain variable region of anti
      c-Met antibody)

<400> SEQUENCE: 114

Asp Ile Gln Met Thr Gln Ser Pro Ser Ser Leu Ser Ala Ser Val Gly
```

```
                1               5                   10                  15
Asp Arg Val Thr Ile Thr Cys Lys Ser Ser Gln Ser Leu Leu Ala Ser
                20                  25                  30

Gly Asn Gln Asn Asn Tyr Leu Ala Trp Tyr Gln Gln Lys Pro Gly Lys
            35                  40                  45

Ala Pro Lys Met Leu Ile Ile Trp Ala Ser Thr Arg Val Ser Gly Val
50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
                100                 105                 110

Lys Arg

<210> SEQ ID NO 115
<211> LENGTH: 50
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: may be present or absent
<220> FEATURE:
<221> NAME/KEY: misc_feature
<222> LOCATION: (11)..(15)
<223> OTHER INFORMATION: may be present or absent
<220> FEATURE:
<221> NAME/KEY: misc_feature
<222> LOCATION: (16)..(20)
<223> OTHER INFORMATION: may be present or absent
<220> FEATURE:
<221> NAME/KEY: misc_feature
<222> LOCATION: (21)..(25)
<223> OTHER INFORMATION: may be present or absent
<220> FEATURE:
<221> NAME/KEY: misc_feature
<222> LOCATION: (26)..(30)
<223> OTHER INFORMATION: may be present or absent
<220> FEATURE:
<221> NAME/KEY: misc_feature
<222> LOCATION: (31)..(35)
<223> OTHER INFORMATION: may be present or absent
<220> FEATURE:
<221> NAME/KEY: misc_feature
<222> LOCATION: (36)..(40)
<223> OTHER INFORMATION: may be present or absent
<220> FEATURE:
<221> NAME/KEY: misc_feature
<222> LOCATION: (41)..(45)
<223> OTHER INFORMATION: may be present or absent
<220> FEATURE:
<221> NAME/KEY: misc_feature
<222> LOCATION: (46)..(50)
<223> OTHER INFORMATION: may be present or absent

<400> SEQUENCE: 115

Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser
            20                  25                  30

Gly Gly Gly Gly Ser Gly Gly Gly Gly Ser Gly Gly Gly Gly Ser
        35                  40                  45

Gly Gly Gly Gly Ser
    50
```

```
<210> SEQ ID NO 116
<211> LENGTH: 15
<212> TYPE: PRT
<213> ORGANISM: Artificial Sequence
<220> FEATURE:
<223> OTHER INFORMATION: Synthetic

<400> SEQUENCE: 116

Gly Gly Gly Gly Ser Gly Gly Gly Gly Ser Gly Gly Gly Gly Ser
1               5                   10                  15

<210> SEQ ID NO 117
<211> LENGTH: 5
<212> TYPE: PRT
<213> ORGANISM: Artificial Sequence
<220> FEATURE:
<223> OTHER INFORMATION: Synthetic

<400> SEQUENCE: 117

Gly Gly Gly Gly Ser
1               5
```